(12) United States Patent
Salmon et al.

(10) Patent No.: US 11,607,345 B2
(45) Date of Patent: Mar. 21, 2023

(54) CHITOSAN MATERIALS WITH ENTRAPPED ENZYME AND BIOCATALYTIC TEXTILES AND OTHER BIOCATALYTIC MATERIALS COMPRISING SAME

(71) Applicant: North Carolina State University, Raleigh, NC (US)

(72) Inventors: Sonja Salmon, Raleigh, NC (US); Yue Yuan, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 171 days.

(21) Appl. No.: 16/805,107

(22) Filed: Feb. 28, 2020

(65) Prior Publication Data
US 2020/0276057 A1  Sep. 3, 2020

Related U.S. Application Data

(60) Provisional application No. 62/811,802, filed on Feb. 28, 2019.

(51) Int. Cl.
*A61F 13/00* (2006.01)
*C08L 5/08* (2006.01)
(Continued)

(52) U.S. Cl.
CPC .. *A61F 13/00995* (2013.01); *A61F 13/00012* (2013.01); *C08L 5/08* (2013.01);
(Continued)

(58) Field of Classification Search
None
See application file for complete search history.

(56) References Cited

U.S. PATENT DOCUMENTS 4,089,746 A * 5/1978 Masri ............... C12N 11/10
435/178
2008/0020036 A1 1/2008 Jolly
(Continued)

FOREIGN PATENT DOCUMENTS

WO   WO 2008/157318   12/2008

OTHER PUBLICATIONS

Krajewska, "Application of chitin- and chitosan-based materials for enzyme immobilizations: a review." Enzyme and Microbial Technology, vol. 35, pp. 126-139 (2004).
(Continued)

*Primary Examiner* — Dominic Lazaro
(74) *Attorney, Agent, or Firm* — Jenkins, Wilson, Taylor & Hunt, P.A.

(57) ABSTRACT

Methods of entrapping enzymes in chitosan matrices using mild conditions, such as methods that are compatible with the entrapment of acid-sensitive and/or heat sensitive enzymes, are described. The methods can provide biocatalytic materials with high chitosan to enzyme mass ratios where one or more enzymes can remain active and stably entrapped in the chitosan matrix for many months and/or after repeated washings. Also described are materials including a solid chitosan matrix having at least one enzyme stably entrapped therein, including fabrics, textiles and other flexible materials at least partially coated with one or more layer of the solid chitosan matrix having at least one enzyme stably entrapped therein and the use of the materials as biocatalyst systems, for example in biogas upgrading and other applications.

8 Claims, 3 Drawing Sheets

(51) Int. Cl.
*D06M 16/00* (2006.01)
*A61L 15/28* (2006.01)

(52) U.S. Cl.
CPC . *D06M 16/003* (2013.01); *A61F 2013/00931* (2013.01); *A61L 15/28* (2013.01)

(56) References Cited

U.S. PATENT DOCUMENTS

| 2009/0010983 A1 | 1/2009 | Melvik et al. |
| 2009/0162439 A1 | 6/2009 | Gobin |
| 2012/0197295 A1 | 8/2012 | Yoshikawa et al. |
| 2015/0099289 A1 | 4/2015 | Bucholz et al. |

OTHER PUBLICATIONS

Huang et al., "Electrochemistry and electrocatalysis with heme proteins in chitosan biopolymer films." Analytical Biochemistry, vol. 308, pp. 141-151 (2002).
Cetinus et al., "Immobilization of catalase on chitosan film." Enzyme and Microbial Technology, vol. 26, pp. 497-501 (2000).
Bilal et al., "Enhanced bio-catalytic performance and dye degradation potential of chitosan-encapsulated horseradish peroxidase in a packed bed reactor system." Science of the Total Environment, vol. 575, pp. 1352-1360 (2017).
Pandey et al., "Chitosan immobilized novel peroxidase from Azadirachta indica: Characterization and application." International Journal of Biological Macromolecules, vol. 104, pp. 1713-1720 (2017).
Wei et al., "Coupling the lactate oxidase to electrodes by inontropic gelation of biopolymer." Anal. Chem., vol. 75, pp. 2060-2064 (2003).
Edwards et al., "Covalent attachment of lysozyme to cotton/cellulose materials: protein versus solid support activation." Cellulose, vol. 18, pp. 1239-1249 (2011).
Lou, "Process technology and properties evaluation of a chitosan-coated Tencel/cotton nonwoven fabric as a wound dressing." Fibers and Polymers, vol. 9(3), pp. 286-292 (2008).
Matatov-Meytal et al., "Review: Catalytic fibers and cloths." Applied Catalysis A: General, vol. 231, pp. 1-16 (2002).
Rathke et al., "Review of Chitin and Chitosan as Fiber and Film Formers." J. Macromol. Sci., Part C, vol. 34(3), pp. 375-437 (1994).
Crini et al. "Application of Chitosan, a Natural Aminopolysaccharide, for Dye Removal from Aqueous Solutions by Adsorption Processes Using Batch Studies: A Review of Recent Literature." Prog. Polym. Sci., vol.33, pp. 399-447 (2008).
Mahapatra "Textile Dyes," WPI Publishing, Boca Raton, FL (2016).

\* cited by examiner

CHITOSAN MATERIALS WITH ENTRAPPED ENZYME AND BIOCATALYTIC TEXTILES AND OTHER BIOCATALYTIC MATERIALS COMPRISING SAME

RELATED APPLICATIONS

This application is based on and claims the benefit of U.S. Provisional Patent Application Ser. No. 62/811,802, filed Feb. 28, 2019, the disclosure of which is incorporated herein by reference in its entirety.

TECHNICAL FIELD

The presently disclosed subject matter relates to methods of stably entrapping enzymes in chitosan matrices using mild conditions; as well as to materials prepared according to the methods, such as flexible substrates coated with a chitosan coating layer comprising at least one enzyme stably entrapped therein. The presently disclosed subject matter further relates to methods of using the materials as biocatalytically-active functional materials, for example, as carbon dioxide filters.

Abbreviations

° C.=degrees Celsius
µL=microliters
µM=micromolar
aq.=aqueous
BCA=bicinchoninic
bCA=bovine carbonic anhydrase
bCAT=bovine catalase
CA=carbonic anhydrase
CAT=catalase
Chi=chitosan
cm=centimeters
Cot=cotton
g=grams
HAc=acetic acid
$H_2O_2$=hydrogen peroxide
kDa=kiloDaltons
L=liter
M=molar
mCA=microbial carbonic anhydrase
mg=milligram
min=minute(s)
mL=milliliter
mM=millimolar
NaAc=sodium acetate
nm=nanometer
nmol=nanomoles
$O_2$=oxygen
PBS=phosphate buffered saline
PC or $K_2CO_3$=potassium carbonate
PH or KOH=potassium hydroxide
pNP=4-nitrophenol
pNPA=4-nitrophenyl acetate
ProK=Proteinase K
PTFE=polytetrafluoroethylene
s=seconds
Tris=tris(hydroxymethyl)amino-methane
v/v=volume by volume
w/w=weight by weight

BACKGROUND

Chitosan is a polymer made from the de-acetylation of chitin, a structural component in the exoskeleton of crustaceans and insects and of the cell walls of fungi. Chitosan has been used in the development of nanomaterials, bioadhesives, and edible coatings. Chitosan has many advantageous properties for use in functional materials, including, but not limited to, biocompatibility, biodegradability to harmless products, nontoxicity, wound-healing properties, antimicrobial properties, and an ability to chelate heavy metal ions. See Kraiewska et al. (Enzyme and Microbial Technology, 35: 126-139 (2004)).

Incorporating enzymes into a chitosan-based matrix can provide a material that adopts the catalytic activity of the enzyme. Prior chitosan-based materials involving immobilized enzymes have generally used highly acidic conditions for solution-based polymer processing that are not compatible with most enzymes. Accordingly, to date, chitosan-based materials comprising immobilized enzymes have largely been limited to those involving post-adsorption of enzymes to a neutralized chitosan surface, or, when a polymer entrapment method is used, the use of enzymes that are tolerant to extreme pH conditions. Prior immobilization methods have also generally relied on the use of an aldehyde-based cross-linking agent (e.g., glutaraldehyde) or another covalent cross-linking agent and/or the use of added polyanions to provide ionotropic gelation.

Accordingly, there is an ongoing need for additional methods of incorporating enzymes into chitosan, particularly those that can be used with acid sensitive enzymes. There is also a need for additional biocatalytically active functional materials comprising chitosan matrices.

SUMMARY

In some embodiments, the presently disclosed subject matter provides a method of preparing a chitosan matrix material comprising an entrapped enzyme, the method comprising: providing an aqueous solution comprising dissolved chitosan, said aqueous solution having a pH of between about 2.5 and about 5.5; adding at least one enzyme to the aqueous solution to provide a chitosan/enzyme solution, wherein the chitosan/enzyme solution comprises a mass ratio of chitosan to enzyme (on a dry basis) of greater than about 0.5; and solidifying the chitosan to provide a solid chitosan matrix, wherein the at least one enzyme is stably entrapped within the chitosan matrix. In some embodiments, providing the aqueous solution comprising dissolved chitosan comprises: (i) dissolving a protonated chitosan salt in a solution having a pH of between about 2.5 and 5.5; or (ii) dissolving a solid chitosan in an aqueous solution comprising an organic acid and having a pH of between about 2.0 and about 4.5; and (ii-a) adjusting the pH of the solution to between about 2.5 and about 5.5; or (ii-b) drying the solution comprising the organic acid to provide a dry protonated chitosan and redissolving the dry protonated chitosan in a solution having a pH of between about 2.5 and about 5.5.

In some embodiments, solidifying the chitosan comprises applying the chitosan/enzyme solution onto a solid support or substrate, wherein the applying comprises pouring, spreading, dipping, painting, rolling, padding, pressing, squeezing, extruding, spraying or printing; and drying the chitosan/enzyme solution to form a film or coating comprising a solid chitosan matrix. In some embodiments, solidifying the chitosan comprises applying the chitosan/enzyme solution to at least one portion of a surface of a textile substrate, and drying the chitosan/enzyme solution to form a film or coating comprising a solid chitosan matrix on the at least one portion of the surface of the substrate. In some embodiments, solidifying the chitosan comprises contacting the chitosan/enzyme solution with a coagulation solution thereby forming a solid chitosan matrix, wherein the at least one enzyme is stably entrapped within the solid chitosan matrix.

In some embodiments, the method is free of: (i) the use of a covalent cross-linking agent reacted with the chitosan prior to, during, or both prior to and during the formation of the solid chitosan/enzyme matrix; and (ii) the addition of an additional polyanion to the chitosan/enzyme mixture, optionally wherein the method is further free of the use of collagen and/or wherein the at least one enzyme is an acid-sensitive and/or a heat sensitive enzyme. In some embodiments, the at least one enzyme remains active and stably entrapped within the chitosan matrix after repeated washings with water or a solution comprising water. In some embodiments, the at least one enzyme is selected from the group comprising an oxidoreductase, a transferase, a hydrolase, a lyase, an isomerase, and a ligase.

In some embodiments, the presently disclosed subject matter provides a coated flexible substrate comprising: (a) a flexible substrate selected from the group comprising a paper, a fiber, a yarn, a ribbon, a fabric and a textile of a natural or synthetic polymer; and (b) a coating layer, wherein the coating layer comprises a solid chitosan matrix material, wherein the solid chitosan matrix material comprises an active enzyme, wherein the active enzyme is stably entrapped within the chitosan matrix material. In some embodiments, the matrix material comprises a mass ratio of chitosan to enzyme (on a dry basis) of greater than about 0.5. In some embodiments, the coating layer further comprises solid, optionally inert, particles.

In some embodiments, the flexible substrate comprises one of the group comprising cotton, rayon, lyocell, jute, linen, hemp, ramie, wool, silk, soy, collagen, fibroin, a product derived from protein, polyester, nylon, polyether ether ketone (PEEK), glass fiber, polyethylene terephthalate, polyurethane, silicone, acrylic, modacrylic, cellulose, man-made cellulosics, cellulose acetate, microbial cellulose, chitosan, chitosan acetate, chitin, wood, a product derived from wood, and combinations thereof. In some embodiments, the active enzyme is selected from the group comprising an oxidoreductase, a transferase, a hydrolase, a lyase, an isomerase, and a ligase.

In some embodiments, the presently disclosed subject matter provides a method of catalyzing a reaction, wherein the method comprises placing a biocatalyst system into contact with a solution or gas comprising an enzyme substrate, wherein said biocatalyst system comprises a flexible, wettable substrate, wherein said flexible wettable substrate is coated with one or more layer of a solid chitosan matrix material, wherein the solid chitosan matrix material further comprises an active enzyme entrapped therein. In some embodiments, the solution comprising the enzyme substrate or a solution comprising enzyme-catalyzed reaction products is transferred from one portion of the biocatalyst system to another via transport in or through the flexible wettable substrate of the biocatalyst system. In some embodiments, placing the biocatalyst system into contact with the solution or gas comprising an enzyme substrate comprises: (a) contacting the flexible wettable substrate of the catalyst system with the solution or gas comprising an enzyme substrate in a first process zone to absorb the enzyme substrate into the flexible wettable substrate and catalyze a reaction to convert the enzyme substrate into a product; (b) transferring the flexible wettable substrate to a second process zone; and (c) releasing a solution or gas comprising the product from the flexible wettable substrate; wherein catalyzing the reaction promotes a desirable chemical transformation.

In some embodiments, the biocatalyst system provides enhanced containment of the solution in the flexible wettable substrate compared to the same flexible wettable substrate in the absence of the one or more layer of solid chitosan matrix material. In some embodiments, the flexible, wettable substrate comprises one of the group comprising cotton, linen, rayon, lyocell, silk, wool, polyamide, polyester and combinations thereof.

In some embodiments, the active enzyme is a carbonic anhydrase, wherein the biocatalyst system is free of a covalent cross-linkage based on glutaraldehyde or another aldehyde, and wherein the method comprises placing the biocatalyst system in contact with a solution or gas comprising carbon dioxide. In some embodiments, the biocatalyst system is a component of a gas scrubber, a component of a biogas upgrading apparatus, a rebreathing apparatus, or an air conditioning apparatus.

Thus, it is an object of the presently disclosed subject matter to provide a method of preparing a chitosan matrix material comprising at least one stably entrapped enzyme, as well as to provide materials comprising (e.g., coated with) a chitosan entrapped enzyme and methods of using the materials to catalyze reactions.

An object of the presently disclosed subject matter having been stated hereinabove, and which is achieved in whole or in part by the compositions and methods disclosed herein, other objects will become evident as the description proceeds when taken in connection with the accompanying Figures as best described herein below.

BRIEF DESCRIPTION OF THE FIGURES

Having thus described the present disclosure in general terms, reference will now be made to the accompanying drawings, which are not necessarily drawn to scale.

Figure 1:
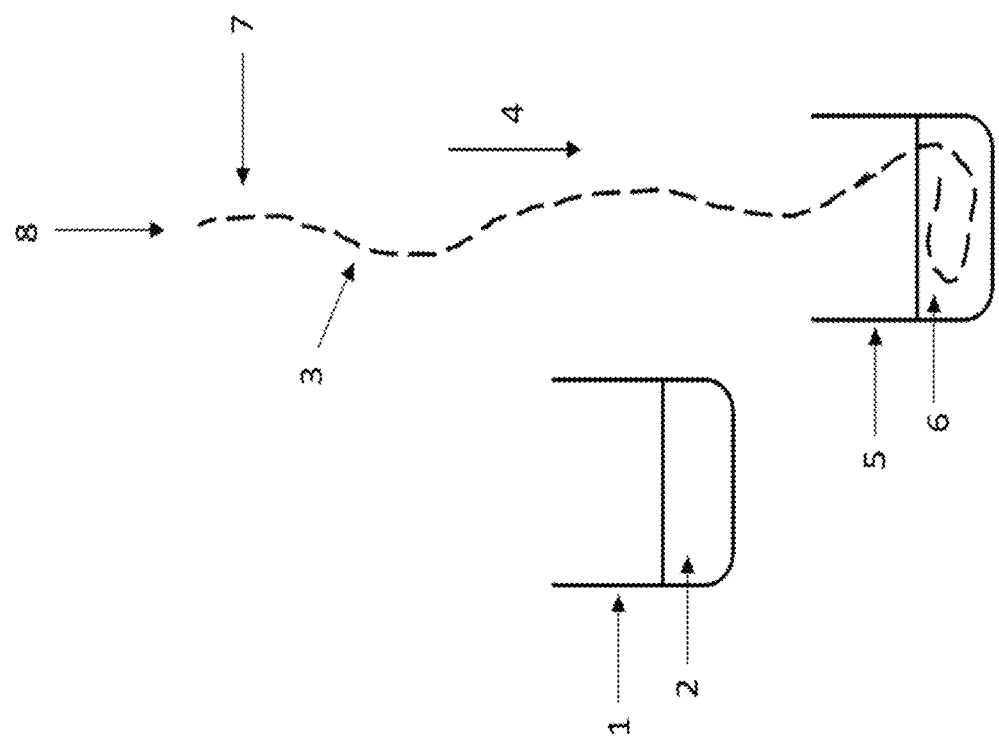

FIG. 1 is a schematic drawing of a wicking test used to study the catalytic effects of materials of the presently disclosed subject matter according to the examples described herein.

Figure 2:
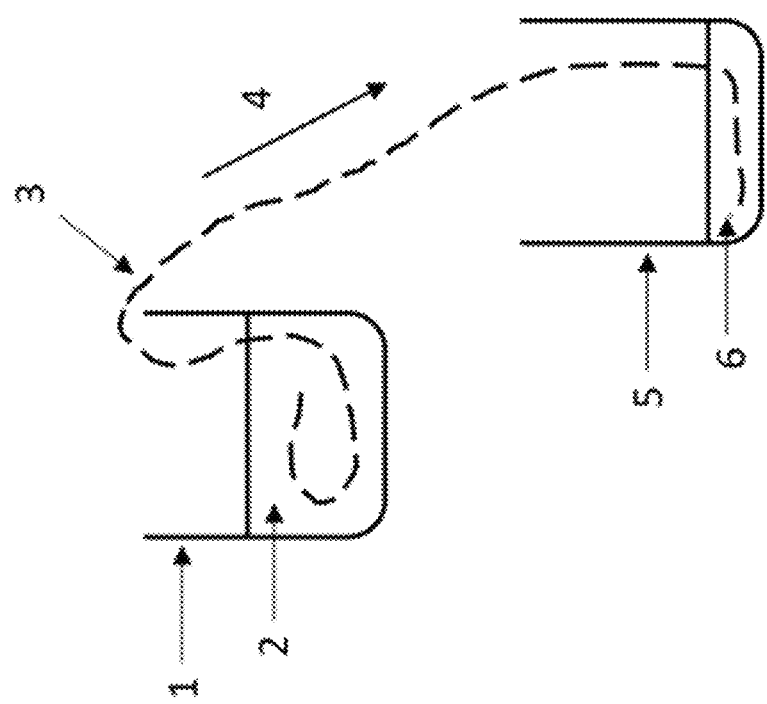

FIG. 2 is a schematic drawing of a flow test used to study the catalytic effects of materials of the presently disclosed subject matter according to the examples described herein.

Figure 3A:
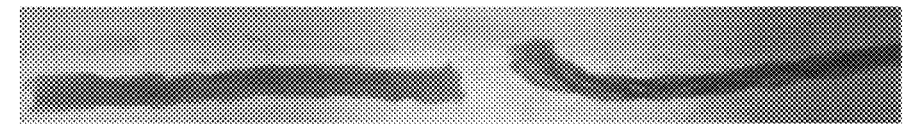
Figure 3A:
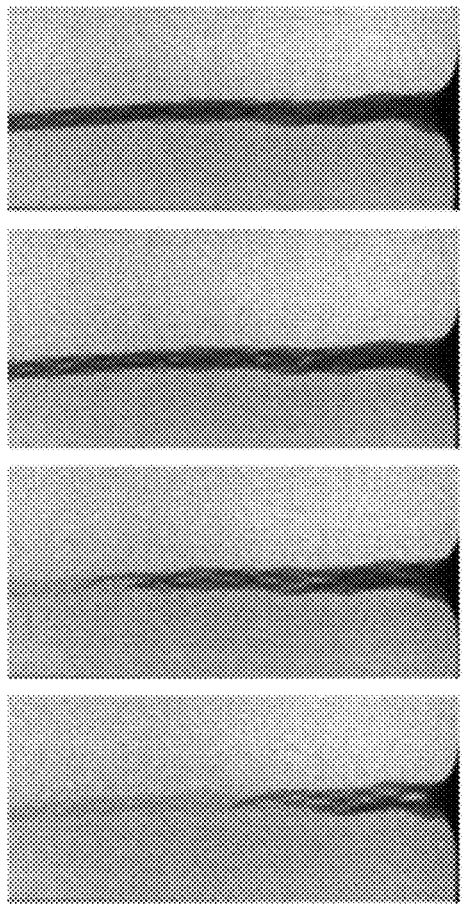

FIG. 3A is a series of neutron tomography images of water wicking in a 4-ply cotton yarn. The length of time the bottom of the yarn is exposed to a reservoir of water increases from the image farthest to the left (0 seconds of exposure) to the image farthest to the right (6 seconds of exposure).

Figure 3B:
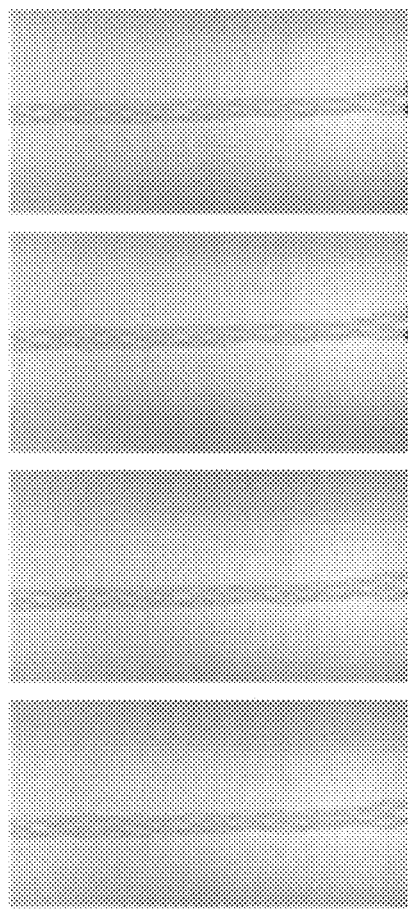

FIG. 3B is a series of neutron tomography images of water wicking in a 4-ply cotton yarn coated with a chitosan matrix material comprising stably entrapped catalase. The length of time the bottom of the yarn is exposed to a reservoir of water increases from the image farthest to the left (0 seconds of exposure) to the image farthest to the right (6 seconds of exposure).

FIG. 3C is a neutron tomography image of (top) the cotton yarn from FIG. 3A after one hour of water wicking; and (bottom) the cotton yarn coated with a chitosan matrix material comprising stably entrapped catalase from FIG. 3B after one hour of water wicking.

Figure 4:
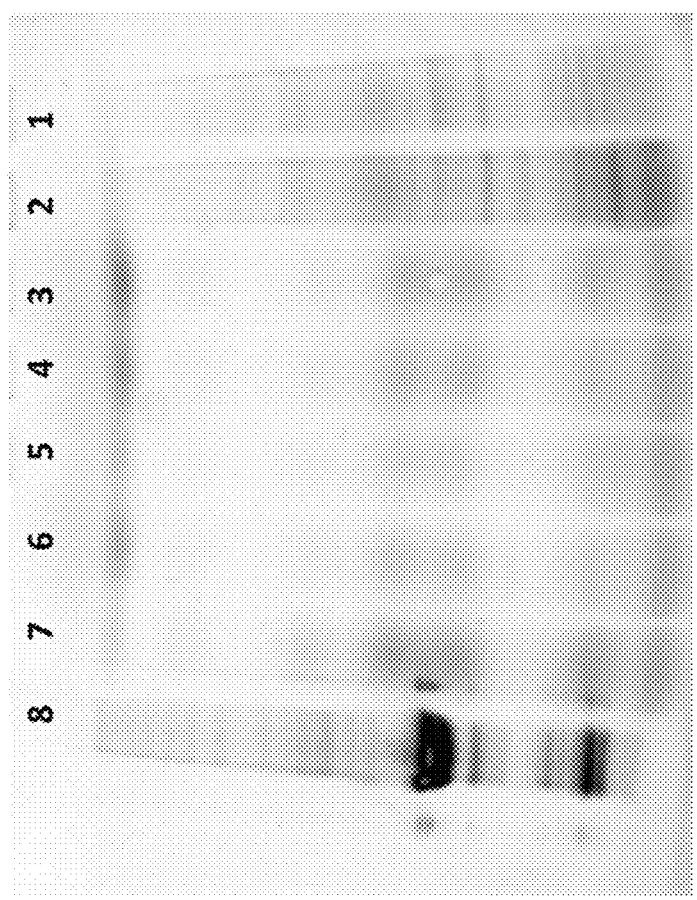

FIG. 4 is a radiograph of a gel electrophoresis study of the results of a degradation assay of casein with: Lane 1, a chitosan film prepared from a solution comprising acetic acid (Chi(HAc)); Lane 2, a chitosan film prepared from a solution comprising sodium acetate and the redissolved film from Lane 1 (Chi-(NaAc)); Lane 3, the chitosan film prepared in the same way as the film in Lane 1 but also including entrapped Proteinase K (Chi-ProK(HAc)); Lane 4, the chitosan film prepared in the same way as the film in Lane 2 but also including entrapped Proteinase K (Chi-ProK (NaAc)); Lane 5, dissolved Proteinase K (8 milligrams (mg)) as a positive control; Lane 6, the Chi(HAc) film with 8 mg dissolved Proteinase K; Lane 7, the Chi(NaAc) film with 8 mg dissolved Proteinase K; and Lane 8, negative control (casein substrate only).

DETAILED DESCRIPTION

The presently disclosed subject matter provides, in some embodiments, a method of preparing a chitosan matrix material comprising at least one enzyme stably entrapped therein wherein the method involves the use of mild conditions, e.g., without the use of strong acids and/or elevated temperatures. For instance, the presently disclosed method can comprise dissolving chitosan polymer (e.g., a protonated chitosan polymer) under relatively mild conditions (e.g., using aqueous solutions comprising organic acids and having a pH between about 2.5 and about 5.5, optionally in the absence of strong acids, ultrasonication and/or heating); adding enzyme, and re-solidifying the chitosan polymer (e.g., again under mild conditions and/or using non-hazardous reagents) where the enzyme becomes stably entrapped inside the chitosan polymeric matrix. In some embodiments, the presently disclosed subject matter provides a chitosan matrix material comprising one or more stably entrapped enzymes prepared according to such a method. In some embodiments, the presently disclosed subject matter provides a coated object comprising a flexible substrate and a coating layer comprising a solid chitosan matrix material comprising one or more enzymes stably entrapped within the chitosan matrix.

In some embodiments, the presently disclosed subject matter provides a biocatalyst system comprising a flexible, wettable substrate wherein the substrate comprises or is coated with one or more layer of solid chitosan matrix material wherein the solid chitosan matrix material further comprises an active enzyme stably entrapped therein. In some embodiments, the presently disclosed subject matter provides a method of catalyzing a reaction using said biocatalyst system.

The presently disclosed subject matter now will be described more fully hereinafter. The presently disclosed subject matter may, however, be embodied in many different forms and should not be construed as limited to the embodiments set forth herein; rather, these embodiments are provided so that this disclosure will be thorough and complete, and will fully convey the scope of the presently disclosed subject matter to those skilled in the art.

I. Definitions

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Definitions of specific chemical functional groups and chemical terms are those that would be understood by one of ordinary skill in the art. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Thomas N. Sorrell (2006) *Organic Chemistry, $2^{nd}$ Edition*, University Science Books, South Orange, N.J.; Smith & March (2001) *March's Advanced Organic Chemistry*, 5th Edition, John Wiley & Sons, Inc., New York; Larock (1989) *Comprehensive Organic Transformations*, VCH Publishers, Inc., New York; and Carruthers (1987) *Some Modern Methods of Organic Synthesis, $3^{rd}$ Edition*, Cambridge University Press, Cambridge; the entire contents of each of which are incorporated herein by reference.

As used herein and in the appended claims, the singular forms "a," "an," and "the" include plural referents unless the context clearly dictates otherwise. For example, "an enzyme" can refer to one or more enzymes. As such, the terms "a", "an", "one or more" and "at least one" can be used interchangeably. Similarly, the terms "comprising", "including" and "having" can be used interchangeably. It is further noted that the claims can be drafted to exclude any optional element. As such, this statement is intended to serve as antecedent basis for use of such exclusive terminology as "solely," "only" and the like, in connection with the recitation of claim elements, or use of a "negative" limitation.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

Unless otherwise indicated, all numbers expressing quantities of concentration, volume, weight, length, width, diameter, thickness, temperature, enzymatic activity, pH, time, mass ratio, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4).

The terms "optional" and "optionally" as used herein indicate that the subsequently described event, circumstance, element, and/or method step may or may not occur and/or be present, and that the description includes instances where said event, circumstance, element, or method step occurs and/or is present as well as instances where it does not.

The term "particle" as used herein can refer to structures that are approximately spherical. However, in addition to spherical shapes, particles can also be other shapes, e.g., disc-shaped, oblong, polyhedral, rod-shaped, cubic, or irregularly-shaped. In some embodiments, the term "bead" is used herein to refer more particularly to particles that are spherical in shape.

The term "nano" (e.g. as in "nanoparticle") refers to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is less than about 10 nm.

The term "micro" (e.g., in "microscale") as used herein refers to a structure having at least one region with a dimension of less than about 1,000 microns (μm). In some embodiments, the term "micro" refers to a structure having a dimension between about 1 micron and about 1,000 microns.

The term "diameter" is used herein to refer to either the physical diameter or the hydrodynamic diameter of a particle. More particularly, the diameter of an essentially spherical particle can refer to the physical or hydrodynamic diameter. The diameter of a non-spherical particle can refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering. The term "diameter" as used herein can also refer to the width of a fiber.

The terms "polymer" and "polymeric" refer to chemical structures that have repeating units (i.e., multiple copies of a given chemical substructure). As used herein, polymers can, in some embodiments, refer to structures having more than 3, 4, 5, 6, 7, 8, 9, or 10 repeating units and/or to structures wherein the repeating unit is other than methylene. Polymers can be formed from polymerizable monomers. A polymerizable monomer is a molecule that comprises one or more reactive moieties {e.g., siloxy ethers, hydroxyls, amines, thiols, vinylic groups (i.e., carbon-carbon double bonds), halides (i.e., Cl, Br, F, and I), esters, carboxylic acids, activated esters, anhydrides, aldehydes, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as acetals, anhydrides, carbonates, urethanes, ureas, ethers, esters or amides, such that they can degrade over time under biological and/or environmental conditions.

The term "copolymer" refers to a polymer prepared from at least two different polymerizable monomers.

The term "chitosan" refers to a polysaccharide comprising 13-(1-4)-linked D-glucosamine and N-acetyl-D-glucosamine. Chitosan can be produced by the partial deacylation of chitin, also referred to as poly-N-acetylglucosamine, a polymeric structural component of the exoskeletons of crustaceans, such as lobsters, crabs, and shrimp, and insects, and the cell walls of fungi. Thus, chitosan can be animal derived or non-animal derived (e.g., fungal chitosan). In some cases, homopolymeric 100% N-acetylated chitin, also referred to as "chitan", can be found in nature, e.g., in certain highly crystalline marine diatom spines. However, most natural chitin contains a number of glucosamine residues in the polymer chain through natural deacetylation processes. The extent of removal of acetyl groups from N-acetyl-D-glucosamine residues in the polymer chain is commonly referred to as the "degree of deacetylation" and is used to describe the amount of glucosamine residues in chitin and chitosan co-polymeric materials. In some embodiments, the degree of deacetylation of the chitosan is between about 50% and about 99%. Typically, compared to chitin, chitosan has a degree of deacetylation of about 70% to about 85%, or to about 95%, or more. In some embodiments, the chitosan has a degree of deacetylation of about 100% and is said to be "fully deacetylated."

The typical molecular weight of chitosan can vary from about 50 kiloDaltons (kDa) to up to around 2000 kDa, depending upon the source, preparation, and measurement method. Lower molecular weight chitosan can be produced by hydrolyzing acetal linkages in higher molecular weight chitosan to obtain "low molecular weight chitosan" with molecular weight in the range of about 5 kDa to about 50 kDa. Chitosan has free amino and hydroxyl groups. The amino groups can be protonated in acidic solutions having a pH of about 6.5 or below, rendering chitosan soluble in such solutions when sufficient protonation is achieved. The presence of protonated amino groups also makes chitosan a cationic polyelectrolyte with a high charge density.

Chitin and its derivatives, including O- and/or N-acetylated chitin, acylated chitin, carboxylated chitin, phosphorylated chitin, chitosan, O- and/or N-acetylated chitosan, acylated chitosan, and carboxylated chitosan, are generally highly biocompatible (e.g., non-antigenic and non-toxic), renewable, and biodegradable. Chemical derivatization is one way to alter the solubility of the chitin and chitosan. Conversion of these materials to soluble derivatives can provide for the use of solution processing techniques to convert these materials from their natural form to different shapes, sizes, and physio-chemical properties. Subsequent chemical derivatization can be used to further alter the material properties, such as chemical derivatization that decreases the solubility of the solution processed material to preserve it in the solidified form. Chemical derivatization can be accomplished by direct chemical reaction between the reagents, or can be catalyzed by organic, inorganic, or enzyme catalysts. Chitin and its derivatives can also provide beneficial biological effects, including but not limited to, wound healing effects (e.g., pro-coagulant effects), antitumor effects, antimicrobial effects, and fungistatic effects.

The term "protonated chitosan" refers to chitosan where some or all of the amino groups are protonated.

The term "protonated chitosan salt" refers to a solid chitosan salt comprising an approximately 1:1 stoichiometry of protonated chitosan amine groups and counterions. In some embodiments, the term is used to distinguish the protonated chitosan salt from a chitosan that was dissolved in an acidic solution comprising an organic acid and which can have a stoichiometric excess of the acid (e.g., at least about 1.25:1 excess of the acid, at least about 1.5:1 excess of the acid; or at least 2:1 excess of the acid).

The term "cellulose" refers to a polysaccharide of β-D-glucose (i.e., β-1,4-glucan) comprising β-(1-4) glycosidic bonds. The term "cellulosic" refers to a composition comprising cellulose.

The term "fiber" as used herein refers to a material that is significantly longer than it is wide, such as at least about 100 times longer than it is wide. The material can be synthetic, semi-synthetic, or natural. Natural fibers (e.g., fibers from plants or animals, including cellulosic, lignocellulosic, chitin, chitosan, and protein-based fibers) typically have a width in the range of about 0.01 to 200 micrometers (μm) and a length that is at least about 100 times the width. Synthetic fibers (e.g., fibers based on synthetic polymers, such as, but not limited to polyamides (including aromatic polyamides), polyacrylonitriles, polyurethanes, polyesters, and polyolefins) can be produced with essentially any length and with widths similar to natural fibers, although larger diameter fibers can also be manufactured. Individual fibers can be continuous filaments (e.g., of essentially infinite length) or cut into shorter lengths or "staple" fibers.

The term "yarn" as used herein refers to a length of interlocked fibers. Yarns can have a very fine width (e.g., in the 1 to 200 μm range) or be much thicker (e.g., 0.5 to 5 millimeter (mm) wide or more).

The term "rope" as used herein refers to a group of yarns and/or fibers that are twisted or braided together. Very thick "rope" structures can also be produced from fibers and yarns. Ropes typically can have widths of 1 mm to 10 cm or more.

The term "fabric" as used herein refers to a flexible network of fibers. In some embodiments, the fabric can be prepared by weaving, knitting, entangling, crocheting or bonding. The term "fabric" as used herein can also refer to flexible materials comprising interlaced fibers, e.g., prepared via weaving, knitting, crocheting, knotting, entangling (such as hydroentangling or needle-punching), felting, or braiding. The term "fabric" as used herein can also refer to a finished cloth, and to materials prepared therefrom, e.g., garments, ribbons, drapes, sheets, covers, filters, meshes, tubes, bags, containers, bandages, and wipes.

The term "textile" as used herein can refer to any type of fiber, yarn, rope, or fabric, as well as their applications, including, but not limited to, garments, ribbons, carpets, towels, furniture covers, automotive covers, drapes, filters, covers, solid reinforcement, bags, containers, tubes, meshes, bandages, wipes, sutures, and threads.

The term "biocatalytic textile" as used herein refers to a textile material partially or completely comprising or covered with a layer comprising solidified chitosan comprising one or more stably entrapped enzyme. The textile material and the coating can both be flexible. In some embodiments, the term refers to a textile material wherein at least one side (e.g., the top or bottom surface) of the textile material is coated with a layer comprising solidified chitosan comprising one or more stably entrapped enzyme. In some embodiments, different sides or faces of the biocatalytic textile can be coated with chitosan layers comprising different enzymes, e.g., so that the different sides can have different biocatalytic activity. Alternatively, in some embodiments, the biocatalytic textile can comprise a textile material prepared from fibers comprising solidified chitosan, wherein the solidified chitosan comprises one or more stably entrapped enzyme.

The term "substrate" as used herein can refer to a solid material (e.g., a flexible solid material, such a material comprising fibers) that can be coated, e.g., with a layer of a solid chitosan matrix material wherein the solid matrix material comprises an enzyme stably entrapped (e.g., non-covalently entrapped) therein. In some embodiments, the term "substrate" can also be used to refer to a molecule that can be converted to another molecule in a reaction catalyzed by an enzyme. In some embodiments, the term "enzyme substrate" can be used to distinguish between molecules that act as the substrate of an enzyme-catalyzed reaction and a solid material "substrate" that can be coated with a layer of solidified chitosan comprising one or more stably entrapped enzyme. In some embodiments, an "enzyme substrate" molecule can be located on or in a solid material "substrate" or can pass through or around a solid material "substrate", such as would happen when the "enzyme substrate" molecule is present in a liquid or gas that is in contact with the solid material "substrate" and/or is flowing through the solid material "substrate."

The term "flexible" when used in reference to a substrate can refer to a material that can be bent (e.g., via manual pressure) without breaking.

The term "wettable" as used herein refers to a material (e.g., a fiber, yarn, rope, ribbon or fabric) that can absorb water or an aqueous solution. Alternatively, in some embodiments, the term "wettable" can refer to a material that can absorb organic liquids when the term is used in association with such liquids, as in "wettable with organic liquids" or "wettable with alkanes."

"Biocompatible" as used herein, generally refers to a material and any metabolites or degradation products thereof that are generally non-toxic (e.g., to a human, animal, and/or plant) and do not cause any significant adverse effects to humans, animals, or plants coming into contact with the material.

"Biodegradable" as used herein, generally refers to a material that will degrade or erode under physiologic conditions, environmental conditions, composting conditions, anaerobic digestion conditions, and/or enzymatically catalyzed conditions, to smaller units or chemical species that are capable of being metabolized, eliminated, or excreted by a living organism. In some embodiments, the degradation time is a function of a material's composition and morphology. In some embodiments, degradation times are from minutes to hours, from hours to days, or from days to months. For example, in some embodiments, the polymer can degrade over a time period from about 15 minutes to about two hours, from about two hours to 48 hours, from about two days to about seven days, or from about seven days to about 24 weeks, optionally from about seven days to about 12 weeks, from about seven days to about six weeks, or from about seven days to about three weeks. In some embodiments, degradation time is longer, e.g., at least a year or more.

The term "alkaline" as used herein can refer to a solution having a pH of greater than 7. In some embodiments, "alkaline" is used to refer to a solution having a pH greater than about 7.5, greater than about 8, greater than about 8.5, or greater than about 9.

The term "acidic" as used herein can refer to a solution having a pH of less than 7. In some embodiments, the term "acidic" refers to a solution having a pH of less than about 6.5, less than about 6, less than about 5.5, or less than about 5.0.

The term "strong acid" as used herein refers to an acid that is completely dissociated or ionized in aqueous solution. Examples of strong acids include, but are not limited to, hydrochloric acid, sulfuric acid, nitric acid, hydrobromic acid, perchloric acid, hydroiodic acid, p-toluenesulfonic acid, and methanesulfonic acid.

The term "organic acid" refers to an organic compound (i.e., a compound comprising one or more carbon atoms covalently linked to atoms of other elements, such as hydrogen, oxygen, or nitrogen) that comprises acidic properties (e.g., the ability to donate a proton and/or to dissociate or partially dissociate in aqueous solutions). Organic acids can include functional groups such as carboxylic acids, sulfonic acids, alcohols (e.g., phenols), thiols, and enols. In some embodiments, the organic acid is an organic compound that includes a carboxylic acid or sulfonic acid group. In some embodiments the organic acid includes a carboxylic acid. In some embodiments, the organic acid is not a strong acid. Examples of organic acids include, but are not limited to, lactic acid, acetic acid, formic acid, citric acid, oxalic acid, tartaric acid, and uric acid. The term "volatile organic acid" refers to an organic acid having a boiling point below about 125° C., such as, acetic acid or formic acid.

The terms "covalent cross-linking reagent" and "covalent cross-linking agent" as used herein can refer to a compound that includes at least two chemical functional groups (or groups that can be deblocked or deprotected to provide the two chemical functional groups) that can react to form covalent bonds with functional groups or moieties on another compound (e.g., a polymer, protein, nucleic acid, or other entity). The two chemical functional groups can be the same or different. In some embodiments, the two functional groups can have different chemical reactivity (e.g., the two functional groups can form covalent bonds with different types of functional groups on other molecules or one of the two functional groups can react more quickly with a particular functional group on another molecule than the other functional group). Thus, a covalent cross-linking reagent can be used to link two other entities, or two groups in the same entity, to form a cross-linked network comprising covalent bonds formed between the covalent cross-linking agent and functional groups on the entity or entities being cross-linked. In particular, the term "covalent cross-linking reagent" as used herein can refer to cross-linking agents that can cross-link chitosan (e.g., different parts on the same chitosan molecule and/or different individual chitosan molecules) by forming covalent bonds with amino or hydroxyl groups on the chitosan. The term "covalent cross-linking agent" is not intended to include the at least one enzyme component of a chitosan/enzyme solution or solidified chitosan material of the presently disclosed subject matter.

A variety of covalent cross-linking agents for use in cross-linking molecules, polymers, and/or proteins are known in the art and/or are commercially available. In some embodiments, the covalent cross-linking agent comprises or is derived from glutaraldehyde, formaldehyde, succinaldehyde, or another aldehyde (or dialdehyde) molecule, which can react with one or more amino or hydroxyl groups on a material being cross-linked. In some embodiments, the covalent cross-linking agent comprises a poly(carboxylic acid) molecule, such as 1,2,3,4-butanetetracarboxylic acid (BTCA), a poly(acrylic acid), citric acid, maleic acid, poly(itaconic acid) or carboxylated polyvinylamine, which can react with one or more amino or hydroxyl groups on a material being cross-linked. In some embodiments, the covalent cross-linking agent comprises a system including the covalent cross-linking agent and a catalyst and/or other auxiliary compounds that improve the cross-linking efficiency and/or performance of the covalent cross-linking agent. In some embodiments, the covalent cross-linking system can include a compound with two functional groups (e.g., a diamine, such as hexamethylenediamine or ethylenediamine) that can react with a functional group on another cross-linking agent in the cross-linking system to serve as a linker or spacer between two other cross-linking agents that are each singly attached to an entity being cross-linked. In some embodiments, the covalent cross-linking agent comprises a poly(carboxylic acid) molecule and a catalyst, such as sodium hypophosphite. Other covalent cross-linking agents include, but are not limited to, glyoxal, 2,5-dimethoxytetrahydrofuran, tris(hydroxymethyl)phosphine, carbodiimides (e.g., DCC and EDC), epichlorohydrin, cyanuric chloride, urea, 1,1,4,4-tetramethoxybutane, 1,1,5,5-tetramethoxypentane, dimethylol ethylene urea (DMEU), dimethylol dihydroxyethyleneurea (DMDHEU), multifunctional vinyl sulfones, multifunctional sulfonyl halides, multifunctional acid halides, N-hydroxysuccinimde (NHS), disuccinimidyl suberate (DSS), bissulfosuccinimidyl suberate (BS3), and homofunctional or heterofunctional derivatives or combinations of these. Other cross-linking agents include, but are not limited to, compounds disclosed in the "Thermo Scientific Crosslinking Technical Handbook" (2012, Thermo Fisher Scientific, Inc.; available at assets.thermofisher.com), herein incorporated by reference. In some embodiments, the covalent cross-linking agent is cyanogen bromide or chemical analogs of cyanogen bromide. In some embodiments, the covalent cross-linking agent is a catalyst that promotes covalent chemical reaction between neighboring functional groups, such as a chemical or enzymatic catalyst, such as carbonyldiimidazole (CDI), glycosyltransferase, tyrosinase, ligase, lyase or esterase.

The term "polyanion" (which can also be referred to as an "anionic polyelectrolyte") as used herein refers to a molecule, polymer, or protein having more than one negative charge. Polyanions can be used to cross-link cations via ionic bonding. For example, protonated chitosan can be ionically crosslinked using a polyanion in a process also referred to in the art as "ionotropic gelation." In some embodiments, the polyanion has 2, 3, 4, 5, 6, 7, 8, 9, 10, 15, 20, 15, 25, 50 or more negative charges. In some embodiments, the polyanion comprises at least 4 or at least 5 negative charges. Thus, for example, in some embodiments, the term "polyanion" refers to polyanions other than dyestuffs. Polyanions include, but are not limited to alginate, carrageenan, xanthan, hyaluronan, polyphosphates (e.g., tripolyphosphate (TPP)), carboxymethyl cellulose, carboxymethylchitin, carboxymethylchitosan, organic sulfates (e.g. heparin, dextran sulfate), poly(aspartic acid), poly (glutamic acid), certain proteins, certain enzymes, and synthetic polymer polyanions, such as, but not limited to poly(acrylic acid) and poly(methacrylic acid). Depending on the isoelectric pH (pI), certain proteins and enzymes can behave as polyanions when the pH of the surrounding medium is above the pI of the protein or enzyme. The pI of proteins and enzymes can be altered using biochemical (e.g., protein engineering) or chemical (e.g., treatment with succinic anhydride) methods to change the number of acidic or basic chemical groups present in the molecule. Since enzymes can often be regarded as polyanions, the term "additional polyanion" as used herein with regard to the presently disclosed chitosan matrix materials comprising one or more stably entrapped enzyme refers to a polyanion other than the one or more enzyme stably entrapped within the chitosan matrix material. Thus, an "additional polyanion" is a polyanion separately added to a solution or mixture comprising chitosan, the one or more enzyme to be entrapped therein, or both, prior to the solidification of the chitosan and the entrapment of the enzyme. In some embodiments, a polyanion can be added to a material of the presently disclosed subject matter after the chitosan is solidified with at least one enzyme stably entrapped therein. In some embodiments, a protein, such as fibronectin (pI 5.5-6), can be added to the material of the presently disclosed subject matter.

The term "solid, optionally inert, particles" refers to particles or powders that can be added to a coating layer, e.g., to increase the surface area or otherwise change the physical properties of the coating layer upon drying, but which typically do not themselves catalyze a reaction of interest. In some embodiments, the solid, optionally inert, particles are porous (e.g., microporous) particles. In some embodiments, the solid, optionally inert, particles are microparticles, nanoparticles, nanofibers, microfibers, or mixtures thereof. The particles can comprise any suitable material, e.g., a polymer (e.g., cellulose, chitin, chitosan, starch, dextran, nylon, polyester, or polymethyl methacrylate), carbon (e.g., carbon nanotubes, carbon fibers, carbon particles, or activated carbon), magnetite ($Fe_3O_4$), maghemite ($Fe_2O_3$), alumina ($Al_2O_3$), glass, silica, metal, clay, bentonite, sepiolite, etc. Additional materials for the particles include, but are not limited to, crushed bone, crushed shells, and hemp hurd. In some embodiments, the solid particles can have an apparent specific surface area of at least about 100 $m^2/g$ or at least about 1000 $m^2/g$. In some embodiments, the solid particles are activated carbon particles or fibers, e.g., which can have an apparent specific surface area in the range of 1500-3000 $m^2/g$. In some embodiments, the particles comprise silicone-based particles, such as xerogels, as described for example in U.S. Patent Application Publication No. 2015/0099289A1 to Bucholz, incorporated herein by reference in its entirety. In some embodiments, the solid particles can comprise microcrystalline or nanocrystalline polymer (e.g., microcrystalline cellulose, microcrystalline chitosan, or microcrystalline chitin), silica powder, magnetite particles, magnetic silica nanospheres, inorganic catalyst particles, organometallic catalyst particles, activated carbon particles, or activated carbon fiber. In some embodiments, one or more enzyme can be adsorbed onto or into the surface, pores, or structure of the particles or powder. In some embodiments, one or more enzyme can be adsorbed onto or into the surface of particles or powders of cellulose, chitin, or chitosan and the particles or powders with adsorbed enzymes can be mixed with a chitosan matrix of the presently disclosed subject matter and the resulting mixture can be dried or solidified to form biocatalytic materials wherein the particles or powders comprising enzymes are entrapped in the chitosan matrix. In some embodiments, the particles can be particles of a chitosan matrix material comprising at least one enzyme stably entrapped therein, such as prepared by a method of the presently disclosed subject matter.

The term "porogen" refers to a material that can be mixed with a polymer solution, and then can be leached out of the polymer structure after the polymer is solidified to create pores in the polymer structure. Porogens that are commonly used to create porous structures include salts, such as, but not limited to sodium chloride, sugars, paraffin, and gelatin. Pore size and extent of porosity can be controlled by the type, size, and concentration of porogens. The use of porogens can be optionally combined with lyophilization to create highly porous polymer structures. In some embodiments, the porosity of a chitosan matrix material can be controlled by the use of porogens.

The terms "pretreat", "pretreatment" and "pretreated" and the like generally refer to chemical, microbial, or mechanical treatments for a substrate, such as a fibrous substrate (e.g., a cotton fabric or other type of fabric) designed to increase the ability of the substrate to interact (e.g., via covalent bonding or electrostatic interactions) with a chitosan coating layer. In some embodiments, the pretreatment comprises a chemical pretreatment used to clean the substrate, alter the hydrophilicity of the substrate, or change the chemistry of the substrate, such as by causing a chemical reaction between a compound and a reactive group (e.g. hydroxyl, amine, carboxylic acid) on the substrate surface. In some embodiments, the pretreatment comprises an enzymatic pretreatment used to clean the substrate (e.g., by degrading an unwanted substance), alter the hydrophilicity of the substrate, or change the chemistry of the substrate, such as by catalyzing a chemical reaction between a compound and a reactive group (e.g. hydroxyl, amine, carboxylic acid) on the substrate surface. In some embodiments, the pretreatment comprises oxidation, irradiation or ozonation of the substrate prior to coating with the coating layer, optionally wherein the irradiation is performed with ultraviolet, gamma, plasma, laser, microwave, electron beam, or ion beam irradiation.

The term "enzyme" refers to a protein (e.g., a globular protein or protein complex) that can catalyze the conversion of one molecule into another. Since enzymes can be produced by living organisms, they can also be referred to as "biocatalysts." The molecule being converted by the enzyme can be referred to as the "substrate" of the enzyme (or the "enzyme substrate") and the molecule produced by the conversion can be referred to as the "product" (or "enzyme product"). Some enzymes can catalyze reactions of multiple different particular substrate molecules. In some embodiments, the different particular substrates are converted into different particular products. Often, enzymes have an overall negative charge.

General classes of enzymes can be referred to based on the type of reaction the enzyme catalyzes. General classes of enzymes include oxidoreductases (Enzyme Commission number (EC) 1), which catalyze oxidation/reduction reactions; transferases (EC 2), which catalyze the transfer of a chemical functional group, such as a methyl group, a glycosyl group, or a phosphate group; hydrolases (EC 3), which catalyze different types of hydrolysis reactions; lyases (EC 4), which catalyze bond cleavages by mechanisms other than hydrolysis or oxidation; isomerases (EC 5), which catalyze isomerizations; and ligases (EC 6), which catalyze the formation of covalent bonds between molecules. Within these general classes of enzymes, enzymes can be referred to more specifically based on the reactions they catalyze and are systematically categorized by the Nomenclature Committee of the International Union of Biochemistry and Molecular Biology (NC-IUBMB).

Examples of oxidoreductases include, but are not limited to, alanine dehydrogenase, alcohol dehydrogenase, alcohol oxidase, bromoperoxidase, carbon monoxide dehydrogenase, catalase, chloroperoxidase, cholesterol oxidase, choline oxidase, dehydrogenase, dioxygenase, galactose oxidase, glucose oxidase, glucose-6-phosphate dehydrogenase, glutamate dehydrogenase, glutamate oxidase, hexose oxidase, kinase monooxygenase, laccase, lactate dehydrogenase, lactate oxidase, leucine dehydrogenase, lipoxygenase, luciferase, lytic polysaccharide monooxygenase (LPMO), monooxygenase, nicotine dehydrogenase, octopine dehydrogenase, oxalate oxidase, peroxidase, peroxygenase, phenol oxidase, polyphenol oxidase, putrescine oxidase, pyruvate dehydrogenase, reductase, sulfite oxidase, thioester reductase, tyrosinase, urate oxidase, uricase, vanadium haloperoxidase, and xanthine oxidase. Examples of transferases include, but are not limited to, am inotransferase, cyclodextrin glycosyltransferase, DNA polymerase, glucosamine acetylase, glucosamine transferase, glycosyltransferase, limonoid glucosyltransferase, nucleoside phosphorylase, phosphotransferase, pyruvate kinase, RNA polymerase, sulfotransferase, transglutaminase, and xyloglucan endotransglycosylase. Hydrolases include, but are not limited to, acetylcholinesterase, alkaline phosphatase, alpha-glucosidase, alpha-L-arabinofuranosidase, alpha-L-rhamnopyranosidase, am idase, am inoacylase, amylase, amyloglucosidase, arginase, arylesterase, asparaginase, beta-galactosidase, beta-glucosidase, beta-xylolidase, bromelain, *Candida antarctica* lipase A (CALA), *Candida antarctica* lipase B (CALB), carboxypeptidase, cellulase, chitinase, chitin deacetylase, chitosanase, chymosin, chymotrypsin, CoA hydrolase, collagenase, creatinine deaminase, cutinase, cysteine protease, deoxyribonuclease, dextranase, endoglucanase, endonuclease, endopeptidase, esterase, endoglucanase, exonuclease, exopeptidase, ficin, galactosidase, glucosidase, glycosidase, hydantoinase, invertase, isoamylase, lactase, lipase, lysozyme, mannanase, mannosidase, metalloprotease, nitrilase, nucleotidase, organophosphate hydrolase, papain, pectinase, pectinesterase, pectin methylesterase, penicillin amidase, penicillinase, pepsin, peptidase, phosphatase, phosphodiesterase, phosphohydrolase, phospholipase, phosphorylase, phosphotriesterase, phytase, plasmin, protease, Proteinase K, pullulanase, raffinase, renin, ribonuclease, serine endopeptidase, serine protease, subtilisin, sulfatase, sulfide hydrolase, sulfide quinone oxidoreductase, tannase, thermolysin, thrombin, trypsin, urease, venombin, and xylanase. Lyases include, but are not limited to, alliinase, anhydrase, aspartate ammonia-lyase, beta-tyrosinase, carbonic anhydrase, decarboxylase, DNA lyase, heparinase, nitrile hydratase, pectate lyase, pectin lyase, phenylalanine ammonia lyase, ribulose-bisphosphate carboxylase (rubisco), RNA lyase, synthase, and tryptophanase. Isomerases include, but are not limited to, epimerase, glucose isomerase, ribose isomerase, and xylose isomerase. Ligases include, but are not limited to, acyl-CoA ligase, acyl-protein synthetase, amide synthase, DNA ligase, pyruvate isomerase, RNA ligase, and synthetase.

Accordingly, examples of more specific enzymes or categories of enzymes include, but are not limited to, aminopeptidase, amylase, anhydrase, carbonic anhydrase, carbohydrase, carboxypeptidase, catalase, cellulase, chitinase, chitosanase, cutinase, glycosylase, glycosyltransferase, cyclodextrin glycosyltransferase, decarboxylase, deoxyribonuclease, glycosyl hydrolase, esterase, alpha-galactosidase, beta-glucosidase, haloperoxidase, invertase, laccase, lipase, lysozyme, mannosidase, kinase monooxygenase, luciferase, lytic polysaccharide monooxygenase (LPMO), nitrilase, oxidase, sulfotransferase, pectinolytic enzyme, peptidoglutaminase, peroxidase, peroxygenase, phytase, phosphorylase, polyphenoloxidase, proteolytic enzyme, protease (e.g., a serine protease (e.g., Proteinase K), a cysteine protease, an aspartyl protease, or a metalloprotease), phosphodiesterase, endonuclease, ribonuclease, transglutaminase, sulfatase, synthase, synthetase, xylanase, and xyloglucan endotransglycosylase.

The enzymes of the presently disclosed subject matter can occur naturally in the environment, be components of a crude extract or preparation, occur in or be obtained from a cell or cell culture, occur in a cell culture broth or medium, or can be purified. The composition of the enzyme can be natural, mutated, or engineered. The composition of the enzyme can be derived from or constructed based on metagenomics analysis or homology-based sequence alignment. The composition of the enzyme can be modified chemically or by incorporation of non-natural amino acids. Enzymes can be mixed or formulated with other enzymes or ingredients intended to improve their performance, such as to improve reaction efficiency and/or extend storage stability.

The term "chitosan-degrading enzyme" as used herein refers to an enzyme that can degrade chitosan. In some embodiments, the chitosan-degrading enzyme is a chitosanase or an exo-β-D-glucosaminidase (GlcNase), such as a GlcNase from *Trichoderma reesei*. In some embodiments, depending on the degree of deacetylation, molecular weight, polymer morphology or other factors, chitosan can be degraded by other enzymes, such as, endo- or exo-chitinase, lysozyme, β-N-acetylhexosaminidase, β-glucosidase or cellulase. In some embodiments, the chitosan-degrading enzyme is a heat-resistant chitinase from *Pyrococcus furiosus*. In some embodiments, depending on the degree of deacetylation, N-acetyl groups in chitosan can be hydrolyzed by chitin deacetylase or chitin oligosaccharide deacetylase. The term "chitosan-degrading enzyme" can also include any enzyme that causes degradation of the chitosan molecular weight. In some embodiments, more than one enzyme participates in the degradation of chitosan, and these enzymes can optionally be contacted to the chitosan sequentially or in a mixture. In some embodiments, the chitosan-degrading enzyme is an enzyme that degrades un-derivatized chitosan. In some embodiments, chemical derivatization of chitosan renders it more degradable by certain enzymes, and these enzymes are referred to herein as "derivatized-chitosan-degrading enzymes."

The extent of chitosan hydrolysis by one or more enzymes can depend on the hydrolysis conditions, such that an enzyme that does not exhibit chitosan hydrolytic activity at one condition can exhibit chitosan hydrolytic activity when the conditions are changed. For example, the changed conditions can be the conditions of the reaction environment, such as temperature, pH, time, and level of mixing, or the changed conditions can be the morphology of the chitosan material, such as level of crystalline or amorphous content, which can be altered by exposure to solvent. The changed conditions can be the chemical composition of the chitosan material, such as degree of acetylation or deacetylation.

The term "heat-resistant enzyme" as used herein refers to an enzyme that maintains activity when exposed for at least 15 minutes to a temperature above about 45° C. or more. In some embodiments, the heat-resistant enzyme maintains activity at a temperature of about 60° C. or more. In some embodiments, the heat-resistant enzyme maintains activity at a temperature of about 70° C. or more. In some embodiments, the heat-resistant enzyme maintains activity at a temperature of about 80° C. or more. In some embodiments, the heat-resistant enzyme maintains activity at a temperature of about 90° C. or more. In some embodiments, the heat-resistant enzyme is also a chitosan-degrading enzyme.

The term "heat-sensitive enzyme" as used herein refers to an enzyme that exhibits about 75% or less or about 50% or less of its catalytic activity, relative to the catalytic activity exhibited at 25° C., when exposed for 15 minutes to temperatures greater than about 45° C. In some embodiments, heat-sensitive enzymes include enzymes found in plants and animals, including luciferase and alkaline phosphatase.

The term "acid-sensitive enzyme" as used herein refers to an enzyme that becomes deactivated or denatured at a pH of about 5.5 or less. In some embodiments, the enzyme becomes deactivated or denatured at a pH of about 4.5 or less, about 4.0 or less, or about 3.5 or less. In some embodiments, acid-sensitive enzymes include many enzymes that function optimally at neutral or alkaline pH, including certain catalases, carbonic anhydrases, alkaline amylases, trypsin, and alkaline phosphatases.

II. General Considerations

The presently disclosed subject matter relates, in some embodiments, to biocatalytically-functional materials comprising enzymes and chitosan, as well as to methods and applications for producing and using these materials. The presently disclosed biocatalytic materials can be used in diverse applications, including, but not limited to, industrial gas separation, biocatalytic reactors, water treatment, wearable sensors, decontamination, reactive packaging, medical and/or veterinary applications, agricultural applications, targeted delivery systems, biocatalyst product formulation, and analytical or diagnostic tests. For example, the presently disclosed biocatalytically functional materials can comprise a chitosan matrix surrounding one or more enzymes, entrapping (e.g., non-covalently entrapping) the one or more enzymes in the matrix. Enzyme substrates, particularly smaller enzyme substrates, can diffuse into the chitosan matrix to reach the entrapped enzyme or enzymes, which can be too large to diffuse out of the matrix, and undergo a reaction catalyzed by the enzyme or enzymes. Typically, the product of the reaction(s) can then diffuse out of the matrix.

Alternatively, in some embodiments, the catalyzed reaction involves a reaction of the enzyme substrate and the chitosan matrix material and the product of the reaction is derivatized chitosan. In some embodiments, an enzyme substrate or cofactor (e.g., hydrogen peroxide ($H_2O_2$) and a reductant) can diffuse into the chitosan matrix and trigger an enzyme (e.g., LPMO) to catalyze a reaction that cleaves or leads to the cleavage of one or more bond in the chitosan matrix material, which can, in some embodiments, make it easier to further degrade or dissolve the polymer (i.e., the chitosan) by adding additional enzymes and/or chemicals and/or via the use of heat or agitation.

In one aspect, the presently disclosed subject matter solves challenges associated with using strongly acidic conditions for dissolving chitosan when chitosan is used as an enzyme entrapping material. For example, the low pH acidic conditions typically used to dissolve chitosan for solution-based polymer processing are not compatible with most enzymes. Therefore, previous studies involving chitosan-based enzyme immobilization have been largely limited to post-adsorption of enzymes on neutralized chitosan surfaces, or, when a polymer entrapment method is used, have been limited to enzymes that can tolerate low pH conditions.

The methods of the presently disclosed methods involve, in some embodiments, dissolving chitosan polymer at mild pH conditions, adding enzyme, and re-solidifying the chitosan polymer under mild conditions using non-hazardous ingredients where the enzyme becomes entrapped inside the chitosan polymeric matrix. These materials and methods are advantageous because they are safe to handle and use, versatile, biobased, biocompatible, and biodegradable. In addition, the biocatalytic materials can be re-dissolved or degraded after use, such as by exposure to low pH, to biological materials (such as enzymes or microorganisms) that can degrade chitosan, or to chemical agents (such as oxidizers), allowing further use of the materials. More particularly, the use of mild pH conditions in the presently disclosed methods minimizes enzyme damage during the fabrication process resulting in highly active biocatalytic solid materials in which a wide variety of enzymes can be incorporated. In addition, the chitosan/enzyme solution can be formed into different shapes prior to (or during) solidification, to generate a broad variety of solid shapes, including, but not limited to, fibers, films, particles, membranes, foams, coatings, gels, blocks, cylinders, and the like, all in a variety of sizes or thicknesses.

In addition, more than one chitosan/enzyme solution can be prepared and used to form alternating layers, plugs, zones and other complex geometries that can control the position of one type of enzyme relative to another type of enzyme and can provide different catalytic performance based on this spatial positioning. The spatial positioning can also provide for cascade reactions to occur as a molecule (e.g. molecule A) passes through the chitosan matrix and is catalytically converted to another molecule (e.g. molecule B) upon encountering one type of enzyme (e.g. enzyme X), and this new molecule (molecule B) is catalytically converted to a third molecule (e.g. molecule C) upon encountering a second type of enzyme (e.g. enzyme Y). In addition, the spatial positioning of chitosan matrix comprising different enzymes can be used to selectively detect the presence of or control the reaction rate of a particular enzyme substrate molecule as it passes through the chitosan matrix.

In some embodiments, the chitosan matrix comprising the at least one enzyme (i.e., the "chitosan/enzyme matrix") can be used as a sensor to detect the presence of an enzyme substrate molecule as it comes in contact with the matrix. In some embodiments, the chitosan matrix comprising at least one enzyme can be used to generate electrical energy, optionally as part of an enzymatic fuel cell or biobattery system, further optionally comprising a conductive polymer, wire or ink.

In some embodiments, at least one molecule exposed to the chitosan/enzyme matrix is an enzyme inhibitor, optionally wherein the binding of the inhibitor to the enzyme results in a decrease in the concentration of the inhibitor in the surrounding medium. In some embodiments, the extent of enzyme inhibition can be monitored, optionally wherein the monitoring can serve as an indicator of the presence in and/or removal of the inhibitor molecule from the medium surrounding the chitosan/enzyme matrix. In some embodiments, the chitosan/enzyme matrix catalyzes the conversion of an enzyme substrate molecule into a product molecule in the presence of an enzyme inhibitor molecule, wherein the chitosan/enzyme matrix can be removed, disposed, and replaced when the catalytic performance of the chitosan/ enzyme matrix falls below a certain threshold due to the presence of enzyme inhibitor molecule.

The presently disclosed biocatalytic materials can provide extended enzyme performance longevity and storage stability, which can be augmented by the inherent pH buffering and antimicrobial properties of chitosan. The materials are durable during use and, as noted above, can be degraded after use, e.g., to provide recovery and reuse of the enzymes or to provide sustainable disposal of the spent biocatalyst.

The presently disclosed biocatalytic materials can extend the performance or appearance of the chitosan matrix or a solid supporting substrate when the enzyme in the chitosan/enzyme matrix catalyzes the chemical conversion of a harmful compound to less harmful compounds, such as to prevent degradation or bleaching of the chitosan matrix, a solid supporting substrate or molecules associated with the chitosan matrix/supporting substrate, such as dyes. For example, catalase entrapped in chitosan can degrade hydrogen peroxide into water and oxygen. When the chitosan/catalase matrix is dyed with a dyestuff that is susceptible to peroxide bleaching, the presence of catalase in the matrix can prevent the bleaching of dye in the matrix by degrading peroxide. In such a system, if bleaching of the dye occurs after repeated exposure to peroxide, detecting the bleaching effect can indicate that the catalase activity has diminished, which can be useful as an indicator for process control.

Further, the presently disclosed methods can provide a liquid-based delivery of a biocatalyst-containing solution to target locations with subsequent immobilization in place by drying and/or raising the pH; and the process can be repeated to replenish spent enzyme or to add additional layers comprising the same or a different enzyme. If desired, the amine and hydroxyl functionalities of chitosan can be used to chemically adjust the material properties for specific applications. Also, if desired, the present materials can provide high enzyme loadings per unit of biocatalyst material. In addition, the mild materials and methods of the presently disclosed subject matter can be used to entrap catalytic cofactors or other non-biological or biological catalysts, such as microorganisms, in addition to, or as an alternative to, one or more enzymes.

In some embodiments, the presently disclosed subject matter relates to the use of the presently disclosed biocatalytically-active materials as a flexible, durable and degradable coating material. Thus, in some embodiments, the presently disclosed subject matter provides a coated object comprising a substrate partially or completely coated with a layer comprising a chitosan matrix material further comprising a chitosan-entrapped enzyme or enzymes. Because the coating materials can be applied to the substrate in liquid form and then solidified, the presently disclosed coated objects can be conformally coated with the biocatalytically-active chitosan-based coating, even in the case where the substrate has a complex surface geometry, e.g., having a rough and/or curved surface or a surface with micro- or nano-sized features (e.g., channels or other depressions, small protrusions, etc.). In some embodiments, the substrate being coated can be any substrate, made of any material (e.g., metal, stone, brick, ceramic, plastic, a composite material, a synthetic or natural fiber, a woven or non-woven textile, a fabric, a yarn, a rope, wood, paper, etc.). In some embodiments, the substrate is not an electrode and/or is not a glass or metal substrate. In some embodiments, the substrate is a flexible substrate, such as a fibrous substrate (e.g., paper or a textile or fabric).

For example, when a fiber or fiber-based material, such as a fabric or textile, is used as the substrate, "biocatalytic textiles" can be produced that integrate the diverse biocatalytic functionality of enzymes with desirable chemo-physical properties of textiles, such as strength, flexibility, high surface area, light weight, chemical functionality, and controllable hydrophilicity, porosity, geometry, and dimensions. Biocatalytic textiles can be used to fabricate multifunctional filters, sensors, wound-dressings, implantable medical devices (e.g., implantable sensors or implantable filters), wipes, packaging, garments and reactor designs. According to the presently disclosed subject matter a wide variety of different kinds of enzymes can be incorporated with low risk of inactivation; and the chitosan polymeric matrix can provide excellent adhesion to both the enzyme and the substrate, providing durability and longevity, including the ability to preserve biocatalytic functionality after washing. Moreover, the biocatalytic coatings can be applied to various substrates, such as textiles, papers, particles and other materials using conventional coating and printing techniques. In some embodiments, the amine and hydroxyl functionalities of the chitosan can be used to modify the chemical and/or physical coating properties for specific applications.

Fibers of chitosan, chitin, and cellulose can be made by methods known in the art. See Rathke and Hudson (*J. Macromol. Sci., Part C,* 34(3), pp. 375-437 (1994)). These fibers can be used as substrates for the chitosan matrix coatings comprising an entrapped enzyme of the present disclosure. In some embodiments, ionic liquids, such as 1-butyl-3-methylimidazolium chloride or 1-ethyl-3-methyl-imidazolium acetate, can be used as a solvent or co-solvent to dissolve chitosan, chitin, cellulose, or derivatives of chitosan, chitin, or cellulose for the purpose of carrying out fiber formation processes. The fibrous materials produced by these methods can be used as substrates for coatings comprising the chitosan matrix comprising an entrapped enzyme. In some embodiments, ionic liquids can be used to prepare a chitosan solution comprising at least one enzyme, and this solution can subsequently be used to form a fiber comprising chitosan and an enzyme or can be used as a coating on substrates of the present disclosure.

Furthermore, chitosan has high affinity for many classes of dyes (also called "dyestuffs"), including acid (anionic), direct, reactive, mordant, vat, and azoic (naphthol) dyes. See Crini and Badot (Prog. Polym. Sci. 33 (2008) pp. 399-447). In some embodiments, chitosan can be chemically modified to acquire a negative charge; and chitosan having a negative charge has affinity for basic (cationic) dyes. In some embodiments, the presently disclosed subject matter relates to treating a chitosan substrate or chitosan matrix material comprising an entrapped enzyme with one or more dyestuffs or pigments. Dyes and pigments can be applied to the materials of the present disclosure according to methods known in the art. See Mahapatra ("Textile Dyes," WPI Publishing, Boca Raton, Fla. (2016)). In some embodiments, the presence of the dyestuff together with the biocatalytic material improves one or more performance properties of the biocatalytic material, such as by decreasing the solubility of the material. Decreasing the solubility of the biocatalytic material can extend its durability to washing. In some embodiments, the presence of dyestuff can be used to track the presence or position of the biocatalytic material, such as when the biocatalytic material is used in a blend or composite with other materials, such as in a fiber blend comprising at least one biocatalytic material or a fabric constructed from different types of yarns, wherein at least one yarn comprises at least one biocatalytic material. In some embodiments, the presence of dyestuff can be used to label or otherwise embellish or alter the appearance of the biocatalytic material. In some embodiments, different dyestuffs can be used to label biocatalytic materials comprising different enzymes. In some embodiments, the presence of the dyestuff can call attention to the presence of the biocatalytic material. In some embodiments, the presence of the dyestuff can be used to reveal the presence of the biocatalytic matrix on a substrate, such as a partially coated substrate, such as a substrate that comprises a printed design of the chitosan matrix comprising an entrapped enzyme. In some embodiments, the presence of the dyestuff can be used to conceal the presence of the biocatalytic material or make the presence of the biocatalytic material indistinguishable from adjacent materials. In some embodiments, the enzyme entrapped in the biocatalytic material can catalyze a reaction with the dyestuff, such as an oxidation or reduction reaction that can enhance or diminish the color of the dyestuff. In some embodiments, the enzyme entrapped in the biocatalytic material can catalyze a reaction between dyestuff precursors, i.e. chemical compounds that react with each other to form colored dyestuffs, to form dyes, optionally dyes that have affinity for the chitosan matrix. In some embodiments, the dyes have color in the visible spectrum or in the infrared spectrum or in the ultraviolet spectrum of light. In some embodiments, the dyes are fluorescent or luminescent dyes. In some embodiments, the biocatalytic materials of the present disclosure can perform both catalytic and dye binding functions, such as in a wastewater treatment application.

III. Methods of Preparing Biocatalytic Chitosan Matrix Materials

Turning now more particularly to the presently disclosed methods of preparing biocatalytically active materials, in some embodiments, the presently disclosed subject matter provides a method of preparing a solid chitosan matrix material comprising an entrapped enzyme. By "entrapped" is meant that the enzyme is physically positioned within, and surrounded by, a matrix of chitosan, and not merely attached to or associated with a surface of the chitosan material. In some embodiments, "entrapped" refers to the enzyme being non-covalently entrapped in the chitosan matrix material, e.g., such that the enzyme is not covalently attached to the chitosan or to any chemical linkage also attached to the chitosan.

In some embodiments, the method comprises providing an acidic solution comprising dissolved chitosan (e.g., dissolved protonated chitosan) and adding at least one enzyme to provide a chitosan/enzyme solution or mixture and then solidifying the chitosan to provide a solid chitosan matrix, wherein the at least one enzyme is stably entrapped (e.g., non-covalently entrapped) within the chitosan matrix. The chitosan can be of animal or non-animal origin. For example, in some embodiments, the chitosan can be derived from shrimp shells. In some embodiments, the chitosan can be of fungal origin (i.e., fungal chitosan), such as a chitosan extracted from the cell walls of a fungus. In some embodiments, the chitosan can be chitosan extracted from *Rhizopus oryzae*.

In some embodiments, the acidic solution comprising the dissolved chitosan has a pH of between about 2.5 and about 5.5 (e.g., about 2.5, 3.0, 3.5, 4.0, 4.5, 5.0, or about 5.5). In some embodiments, the pH is between about 3.6 and about 5.5 or between about 4.0 and about 5.5. In some embodiments, the mass ratio of chitosan to enzyme (on a dry basis) in the chitosan/enzyme solution and/or the solid chitosan matrix comprising the at least one stably entrapped enzyme is about 0.5 or greater (e.g., about 0.50, 0.55, 0.60, 0.65, 0.70, 0.75, 0.80, 0.85, 0.90, 0.95, 1.0, 1.1, 1.2, 1.3, 1.4, 1.5, 1.6, 1.7, 1.8, or about 1.9 or greater), optionally about 2 or greater (e.g., about 2.0, 2.25, 2.50, 2.75, 3.0, 3.25, 3.50, 3.75, 4.0, 4.25, 4.50, 4.75 or greater), optionally about 5 or greater (e.g., about 5, 6, 7, 8, 9, or 10 or greater), optionally about 10 or greater (e.g., about 10, 15, 20, 25, 50, 100, 500, 1000).

In some embodiments, providing the acidic solution comprising the dissolved chitosan comprises dissolving a solid protonated chitosan material (e.g., a protonated chitosan salt) in the acidic solution. The protonated chitosan material can be, for example, a commercially available product (e.g., chitosan lactate or chitosan acetate sold under the tradename CHITOVAN™ (Dungeness Environmental Solutions, Inc., Everett, Wash., United States of America).

Alternatively, in some embodiments, providing the acidic solution comprising the dissolved chitosan comprises dissolving a chitosan material in an acidic solution (e.g., having a pH of between about 2.0 and about 4.5 or between about 2.0 and about 3.5) to protonate the chitosan; adjusting the pH, if necessary, to between about 2.5 and about 5.5; and then adding the at least one enzyme. In some embodiments, the dissolving is free of ultrasonication or heating. In some embodiments, any chemicals used to adjust the pH and/or the enzyme can be added to the acidic solution dry, as opposed to being in dissolved form.

In some embodiments, providing the acidic solution comprising the dissolved chitosan comprises first dissolving solid chitosan in an acidic solution (e.g., having a pH of between about 2.0 and about 4.5 (e.g., between about 2.0 and about 3.5) and comprising an organic acid, optionally a volatile organic acid) to protonate the chitosan and then removing the liquid to provide a dry protonated chitosan which can then be redissolved.

Thus, in some embodiments, providing the aqueous solution comprising dissolved chitosan comprises: (i) dissolving a protonated chitosan salt in a solution having a pH of between about 2.5 and 5.5; or (ii) dissolving a solid chitosan in an aqueous solution comprising an organic acid (e.g., a volatile organic acid) and having a pH of between about 2.0 and about 4.5, and optionally: (ii-a) adjusting the pH of the solution to between about 2.5 and about 5.5 (e.g., by adding a dry chemical to the solution) or (ii-b) drying the solution comprising the organic acid to provide a dry protonated chitosan and redissolving the dry protonated chitosan in a solution having a pH of between about 2.5 and about 5.5.

In some embodiments, the method of preparing a chitosan matrix material comprising an entrapped enzyme comprises: (a) dissolving solid chitosan in a first aqueous solution, wherein the first aqueous solution comprises an organic acid (e.g., a volatile organic acid, such as, but not limited to acetic acid, formic acid or lactic acid), and has a pH between about 2.0 and about 4.5 (e.g., between about 2.0 and about 3.5, or between about 2.5 and about 3.0), to prepare a first chitosan solution; (b) drying the first chitosan solution to provide a protonated chitosan solid; (c) dissolving the protonated chitosan solid in a second aqueous solution, optionally wherein the second aqueous solution has a pH between about 2.5 and about 5.5 (e.g., between about 3.6 and about 5.5 or between about 4.0 and about 5.5), thereby providing a second chitosan solution; (d) adding at least one enzyme to the second chitosan solution; thereby providing a chitosan/enzyme solution; and (e) solidifying the chitosan in the chitosan/enzyme solution to form a solid chitosan matrix, wherein the at least one enzyme is stably entrapped (e.g., non-covalently entrapped) within the solid chitosan matrix. In some embodiments, excess organic acid is removed by evaporation during step (b).

Thus, in some embodiments, the method comprises dissolving a solid chitosan in a first aqueous solution under mildly acidic conditions to provide a solution comprising protonated chitosan. In some embodiments, the first aqueous solution comprises an organic acid and has a pH of between about 2.0 and about 4.5 (e.g., about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, or about 4.5). In some embodiments, the pH of the first aqueous solution is between about 2.0 and about 3.5. In some embodiments, the pH is between about 2.5 and about 3.0. In some embodiments, the organic acid is a volatile organic acid, such as acetic acid, formic acid or lactic acid, which can be easily evaporated from the solution after the chitosan is dissolved.

In some embodiments, the solution is dried to provide a protonated chitosan solid. The protonated chitosan solid can then be redissolved in a second aqueous solution. The second aqueous solution can be water or a buffered solution. In some embodiments, the second aqueous solution has a pH between about 2.5 and about 5.5 (e.g., about 2.0, 2.5, 3.0, 3.5, 4.0, 4.5, 5.0, or about 5.5). In some embodiments, the second aqueous solution has a pH between about 3.6 and about 5.5. In some embodiments, the second aqueous solution has a pH between about 4.0 and about 5.5. In some embodiments, the second aqueous solution (or any solution comprising dissolved chitosan and having a pH of between about 2.5 and about 5.5) comprises a dissolved buffering agent or agents. Suitable buffering agents include, but are not limited to, acidic buffering agents known in the art, such as those based on acetate salts, formate salts, citrate salts, lactate salts, and mixtures thereof. For example, the buffering system can comprise sodium acetate, sodium lactate, or sodium formate.

Alternatively, instead of drying the protonated chitosan to provide a protonated chitosan solid and then redissolving the protonated chitosan solid in a second solution, the organic acid can optionally be volatilized and, if desired, the pH of the first solution can be adjusted e.g., to between about 4.0 and about 5.5, without fully drying the solution. However, fully drying the protonated chitosan can be advantageous in that it can provide for more control of the chitosan concentration when the protonated chitosan is redissolved in the second aqueous solution, as well as providing for second aqueous solutions and chitosan/enzyme solutions of higher chitosan concentration.

One or more enzyme is then added to the second aqueous solution comprising the dissolved or redissolved protonated chitosan, thereby providing a homogeneous chitosan/enzyme solution or a heterogenous chitosan/enzyme mixture. In some embodiments, the chitosan/enzyme solution or mixture comprises at least about 1 mg/mL of chitosan or at least about 5 mg/mL of chitosan. In some embodiments, the chitosan/enzyme solution or mixture comprises at least about 10 mg/mL of chitosan (e.g., about 10, 15, 20, 25, 30, 35, 40, 45, 50, 55, 60, or 70 mg/mL of chitosan). In some embodiments, the chitosan/enzyme solution or mixture has a mass ratio of chitosan to enzyme (on a dry basis) of about 0.5 or greater (e.g., about 0.50, 0.55, 0.60, 0.65, 0.70, 0.75, 0.80, 0.85, 0.90, 0.95, 1.0, 1.1, 1.2, 1.3, 1.4, 1.5, 1.6, 1.7, 1.8, or about 1.9 or greater), optionally about 2 or greater (e.g., about 2.0, 2.25, 2.50, 2.75, 3.0, 3.25, 3.50, 3.75, 4.0, 4.25, 4.50, 4.75 or greater), optionally about 5 or greater (e.g., about 5, 6, 7, 8, 9, or 10 or greater), optionally about 10 or greater (e.g., about 10, 15, 20, 25, 50, 100, 500, 1000).

Then, the chitosan/enzyme solution or mixture is solidified to form a solid chitosan matrix, wherein the enzyme is stably entrapped within the solid chitosan matrix. The solidification can be performed in a variety of different ways. For example, the chitosan/enzyme solution or mixture can be delivered to a particular location while still in liquid form and then solidified in situ by raising the pH (e.g., to above about 6.5, above about 7.0, or above about 8.0) or by drying the material so that the liquid portion of the solution or mixture evaporates (e.g., under ambient conditions (i.e., room temperature and humidity), via the application of a stream of a dry gas, such as, but not limited to dehumidified air, nitrogen, or argon, or via the application of heat (optionally in combination with the application of a stream of dry gas)). In some embodiments, drying the chitosan/enzyme solution comprises contacting the solution with a "coagulation solution", e.g., a solution having a pH of about 6.5 or more. Additional details regarding suitable coagulation solutions are described hereinbelow. The term "coagulation solution" can also be referred to as a "neutralization solution" or a "deprotonation solution." In some embodiments, the chitosan/enzyme solution can be dried by air drying or another drying technique where the chitosan remains in its protonated state, but is then neutralized, e.g., by being contacted with a neutralization solution, as the chitosan matrix can be more stable (e.g., less soluble in aqueous solutions) in the neutralized form.

Typically, the addition of the at least one enzyme is performed at a temperature below the denaturation temperature of the at least one enzyme. In some embodiments, the addition is performed at a temperature below about 40° C. In some embodiments, the addition is performed at about room temperature (i.e. between about 18° C. and about 30° C. or between about 18° C. and about 25° C.). In some embodiments, one or more additional steps of the method or all of the steps of the method are performed at a temperature below about 40° C. In some embodiments, one or more additional steps or all of the steps are performed at room temperature.

In some embodiments, the chitosan/enzyme solution or mixture can be applied to a solid support or substrate and dried to form a film or coating comprising a solid chitosan matrix wherein at least one enzyme is stably entrapped within the solid chitosan matrix. Suitable application techniques include, but are not limited to, pouring, spreading, dipping, painting, rolling, padding, pressing, squeezing extruding, spraying or printing. For instance, when the solid support is flat, the solution or mixture can form a layer of any desirable thickness and solidified to form a film or sheet comprising a solid chitosan matrix material comprising a stably entrapped enzyme. If desired, the film or other coating can be removed from the solid support to provide an unsupported chitosan-based solid. In some embodiments, the solid support can be a mold comprising one or more indentations that can be filled with the chitosan/enzyme solution or mixture. When solidified and removed from the mold, various three-dimensional shapes comprising the solid chitosan matrix material comprising the stably entrapped enzyme can be provided.

In some embodiments, solidifying the chitosan comprises applying the chitosan/enzyme solution to at least one portion of a surface of a textile substrate (e.g., via controlled spraying, spreading, padding, printing or painting), and drying the chitosan/enzyme solution to form a film or coating comprising a solid chitosan matrix on the at least one portion of the surface of the substrate. In some embodiments, the at least one portion of the surface of the substrate is one face (i.e., the top or bottom face) or a part of one face of the textile substrate. In some embodiments, the method further comprises applying one or more additional chitosan/enzyme solution comprising one or more different enzymes to the same portion of the surface of the textile substrate or to a different portion of the surface of the textile substrate; and drying the one or more additional chitosan/enzyme solutions to form a film or coating comprising a solid chitosan matrix. Thus, the textile substrate can have coatings comprising different enzymes located at different sites on the surface of the textile. In some embodiments, the different portion of the surface of the textile substrate is an adjacent surface or an opposite surface of the substrate. In some embodiments, an entire face or all surfaces of the substrate are coated with the same chitosan/enzyme solution, thereby providing, when solidified, a fully coated substrate.

In some embodiments, the drying is performed under ambient conditions. In some embodiments, the drying comprises applying heat and/or a dry gas stream. In some embodiments, the dry gas stream comprises dehumidified air.

In some embodiments, the chitosan/enzyme solution can be poured or otherwise applied to a substrate (e.g., a flexible substrate, such as a fabric) and solidified to provide a coated substrate (e.g., a coated flexible substrate) comprising a coating layer comprising a solid chitosan matrix material comprising a stably entrapped enzyme. Alternatively, a flexible substrate (e.g., a fiber, yarn or fabric) can be submerged into the chitosan/enzyme solution or mixture, removed from the solution or mixture, and dried to provide a coated substrate. Thus, for example, a substrate can be dip-coated in the chitosan/enzyme solution or mixture. In some embodiments, the substrate has a net negative surface charge or a more negative surface charge than the chitosan/enzyme solution. Solidification of the coating layer on the substrate can be performed using any suitable technique, e.g., by drying in air, by exposing the coating to a complexing agent that causes chitosan to solidify, by raising the pH of the coating solution, or by any combination of these techniques. In some embodiments, multiple layers of the coating can be applied sequentially to the surface of a substrate. Such multiple coatings can be durable due to the adhesion possible between an existing solidified chitosan/enzyme layer and the next deposited layer. Without being bound by any one theory, this adhesion can arise from slight solubilization of the solidified layer when the next layer of mildly acidic chitosan-enzyme solution is applied, resulting in some physical entanglement or adhesion between the chitosan polymer chains in the two layers.

In some embodiments, the coating layer can conformally or substantially conformally coat at least a portion of the surface of the substrate (e.g., the flexible substrate). By "conformally" is meant that the coating layer follows the surface profile of the substrate without a loss of detail. By "substantially conformally" is meant that at least 75% or more of the details of the surface of the substrate are still observed in the coating layer and/or that some loss of proportion, e.g., the height of a protrusion or the depth of a channel can occur. In some embodiments, one side or face of the substrate is coated. In some embodiments, all sides or faces of the substrate are coated. In some embodiments, the coating layer can be applied to less than an entire side or face of a substrate. For example, the coating can be applied in a fine line, dot, or detailed pattern of regular or irregular shapes to one or more faces of the substrate.

In some embodiments, the ability of the coating to bind tightly to the fiber surface contours does not substantially impair the flexibility of a fiber-based substrate, because the coating can be thin and can bend and flex with the motion of the fiber. This property can be of use in applications where the ability to bend, fold, and drape the fibers of the fiber-based substrates enhances the features and/or performance of the biocatalytically coated substrate.

The substrate can be any suitable material of any suitable shape, e.g., a fiber, yarn, fabric, ribbon, rope, paper, films, particle, membrane, porous foam, non-porous foam, solid surface, block, ball, cylinder, irregular shape, etc., in any desired size. In some embodiments, the substrate is a textile, a garment, paper, a diaper, a wound dressing, a filter, packaging, or a container. In some embodiments, the substrate can comprise cotton, rayon, modal, lyocell, jute, linen, hemp, ramie, wood, cellulose acetate, or another cellulose-based fiber, yarn or fabric, silk, wool, soy, fibroin, keratin, collagen, or another protein-based fiber, yarn or fabric, or chitin-based or chitosan-based fiber, yarn, or fabric. In some embodiments, the substrate can comprise regenerated cellulose, chitin or chitosan or mixtures or blends of these. In some embodiments, the substrate can comprise an aliphatic polyester, such as polylactic acid (PLA), polyhydroxyalkanoate (PHA), polyhydroxybutyrate (PHB), polypentadecalactone (PPDL), polycaprolactone (PCL) or a related material. In some embodiments, the substrate is a polyester based on furan dicarboxylic acid (FDCA). In some embodiments, the substrate can comprise a petrochemical-based material, such as, but not limited to, polyethylene, polypropylene, polystyrene, polyethylene naphthalate (PEN), polyethylene terephthalate (PET), nylon, acrylic, modacrylic, spandex, and polyurethane. In some embodiments, all or a portion of these materials are biobased materials. In some embodiments, the substrate can comprise a blend or mixture of materials. In some embodiments, the substrate is biodegradable, thus providing a coated object that is completely biodegradable. In some embodiments, the substrate can comprise a material that has a pre-existing affinity for chitosan, such as a cellulose-based substrate (e.g., a cellulose-based paper or textile substrate), a chitin-based substrate, a chitosan-based substrate, or another substrate comprising a material with hydroxyl and/or amine groups. In some embodiments, the chemical composition or surface of the substrate can be modified to improve the affinity or interaction between chitosan and the material surface. In some embodiments, the mild conditions used to prepare the coating can provide for the use of delicate substrates that would degrade under extreme acidic conditions.

In some embodiments, solidifying the chitosan comprises: submerging a substrate, such as a fiber, yarn, fabric, or textile (e.g., a cellulose-based fiber, yarn, fabric or textile) into a chitosan/enzyme solution for a period of time; removing the substrate from the solution; and drying the substrate, thereby forming a coated substrate, wherein the substrate is conformally coated with a coating layer comprising a solid chitosan matrix, wherein at least one enzyme is stably entrapped within the solid chitosan matrix. In some embodiments, excess solution can be removed from the substrate prior to drying. In some embodiments, the drying is performed under ambient conditions.

In some embodiments, the coated substrates of the presently disclosed subject matter can be prepared in the absence of any substrate pretreatment particularly designed or performed to increase the adherence of the chitosan matrix material, such as a treatment to increase the number of anions on the surface of the substrate or a treatment to add a group that can covalently bond to a group on the chitosan. Thus, for example, in some embodiments, the coated substrate is non-covalently coated with one or more layers of a solid chitosan matrix material. In some embodiments, the substrate material already includes groups that can interact (covalently or non-covalently (e.g., electrostatically)) with the amino or hydroxyl groups of the chitosan. Thus, in some embodiments, the chitosan has a dual role in providing an attractive interaction with the substrate surface and an attractive interaction for entrapping the enzyme. Alternatively, in some embodiments, the substrate can be pretreated, e.g., physically or chemically modified, to enhance the affinity and binding of chitosan to the substrate. In some embodiments, the substrate can be treated with a covalent linking agent (e.g., hydroxydichloro-1,3,5-triazine sodium salt (Na-HDCT)) to increase the adherence of the chitosan and to provide a coated object comprising a layer of covalently attached chitosan.

In some embodiments, the chitosan/enzyme solution or mixture can be introduced into a coagulation solution or bath to solidify the chitosan and entrap the enzyme therein, thereby forming a solid chitosan matrix, wherein at least one enzyme is stably entrapped within the solid chitosan matrix. In some embodiments, the coagulation solution has a pH of at least about 6.5 (e.g., between about 6.5 and about 14). In some embodiments, the coagulation solution is an alkaline coagulation solution. In some embodiments, the coagulation solution or bath comprises an alkaline alcoholic solution (e.g., a solution comprising sodium methoxide in methanol) or an alkaline aqueous solution, e.g., having a pH of about 8 or more (e.g., between about 8 and about 14, or between about 9 and about 12). Suitable buffering systems for the coagulation solutions are known in the art. For instance, suitable coagulation solutions for use according to the presently disclosed methods can include buffering systems, including, but not limited to, those comprising carbonate salts (e.g., potassium, sodium, or lithium salts), phosphate salts, TRIS, DEEA, MDEA, amino acids, or MEA, as well as pH buffered solutions of hydroxide salts (e.g., NaOH, KOH, LiOH). Thus, in some embodiments, the coagulation solution comprises one or more of a carbonate salt, a bicarbonate salt, a borate salt, a phosphate salt, an organic amine, and a pH-buffered hydroxide salt. In some embodiments, the coagulation solution comprises an alkaline aqueous solution comprising a salt or salts selected from potassium carbonate, sodium carbonate, potassium bicarbonate, and sodium bicarbonate. In some embodiments, the coagulation solution is a concentrated salt solution, a solution comprising a surface-active agent (e.g., a surfactant), or a solution comprising a polyanion. In some embodiments, the concentrated salt solution can comprise one or more multivalent ions. In some embodiments, the concentrated salt solution can comprise tripolyphosphate (TPP), magnesium gluconate, a sulfate salt, and/or calcium, magnesium, or manganese ions. Suitable surfactants include, but are not limited to, sodium dodecyl sulfate, 1-butyl-methylimidazolium octyl sulfate, and sodium taurodeoxycholate. Suitable polyanions include, but are not limited to, carboxymethylcellulose (CMC), carboxymethylchitosan, alginate, hyaluronan, heparin, chondroitin sulfate, polyacrylate, and poly (styrene sulfonate).

The chitosan/enzyme solution or mixture can be introduced into the coagulation solution (e.g. via extrusion, pipette, or dropper) as droplets, e.g., thereby forming particles, flakes, or beads comprising solid chitosan matrix material comprising a stably entrapped enzyme. After solidification, the particles or beads can be removed from the solution for use in various catalytic applications. In some embodiments, a stream of the chitosan/enzyme solution or mixture can be introduced into the alkaline coagulation solution (e.g., via injection using a syringe or via extrusion through a spinneret) and solidified to form a fiber, wherein the body of the fiber comprises solid chitosan matrix material having an enzyme stably entrapped therein.

In some embodiments, a surface of the chitosan/enzyme solution (e.g., the surface of a chitosan/enzyme solution coated on a flexible substrate) can be contacted with the coagulation solution, thereby forming a film comprising the solid chitosan matrix, wherein the at least one enzyme is stably entrapped within the solid chitosan matrix. For instance, the coagulation solution can submerge or flow over the chitosan/enzyme solution. In some embodiments, the chitosan/enzyme solution can be absorbed onto or within a fiber containing substrate, such as a textile, fiber or yarn, when contacted with the coagulation solution.

In some embodiments, the chitosan/enzyme solution or mixture can be exposed to low humidity air or a low humidity gas environment to solidify the chitosan and entrap the enzyme therein by drying the material so that the liquid portion of the solution or mixture evaporates. In some embodiments, a stream of the chitosan/enzyme solution or mixture can be introduced into the low humidity environment (e.g., via injection using a syringe or via extrusion through a spinneret) and solidified to form a fiber, wherein the body of the fiber comprises solid chitosan matrix material having an enzyme stably entrapped therein. In some embodiments, the low humidity environment comprises a dry gas, such as, but not limited to dehumidified air, nitrogen, or argon (optionally where the dry gas flows around or through the stream of chitosan/enzyme solution). In some embodiments, the low humidity environment is achieved via the application of heat, to promote evaporation of solvent from the chitosan/enzyme solution (optionally in combination with the application of a stream of dry gas). In some embodiments, the solidified chitosan matrix can be neutralized after initial solidification, e.g., by contact with an alkaline coagulation solution.

In some embodiments, the chitosan/enzyme solution or mixture can be solidified through the process of electrospinning, during which the liquid portion of the solution or mixture evaporates, resulting in a solid chitosan matrix material having an enzyme stably entrapped therein.

By "stably entrapped" as used herein refers to an enzyme that (1) exhibits enzyme activity while entrapped in the chitosan matrix and/or (2) exhibits enzyme activity when released from the matrix (e.g., after swelling of the chitosan matrix that can result in release of enzyme or after degradation of the chitosan matrix using a chitosanase). In some embodiments, the entrapped enzyme exhibits at least about 25% (or at least about 30%, 35%, 40%, 45% or more) or the enzymatic activity expected based on the amount of enzyme incorporated into the matrix. In some embodiments, the entrapped enzyme exhibits at last about 50% (or at least about 55%, 60%, 65%, 70%, or more) or the enzymatic activity expected based on the amount of enzyme incorporated into the matrix. In some embodiments, the entrapped enzyme exhibits at least about 75% (or at least about 80%, 85% 90%, 95% or more) of the enzymatic activity expected based on the amount of enzyme incorporated into the matrix. In some embodiments, "stably entrapped" refers to the ability of the enzyme to remain entrapped without significant leaching from the chitosan matrix material. For instance, a material without significant leaching is a material that loses less than about 20%, less than about 15%, less than about 10%, or less then about 5% of the entrapped enzyme after repeated washing with water or with soap and water and/or after contact with surfactants, optionally with the use of mechanical agitation (e.g., stirring or shaking). In some embodiments, "stably entrapped" refers to a material wherein the entrapped enzyme retains at least about 50%, at least about 60%, at least about 70%, or at least about 80% of its original activity after dry storage of the biocatalytically active material for at least one month, at least two months, at least about three months, at least about 6 months, at least about 9 months, or at least about 1 year. In some embodiments, a solid chitosan/enzyme material with a relatively low initial activity (e.g., about 25%) compared to the initial activity (e.g., 100%) of the corresponding non-entrapped enzyme can provide improved catalytic efficiency in that the performance longevity of the chitosan/enzyme material (e.g., 10 days) can exceed that of the corresponding non-entrapped enzyme (e.g., about 1 day).

In some embodiments, the solid chitosan matrix material comprising the stably entrapped enzyme exhibits detectable enzyme activity. For example, the solid material can be placed into a solution or under an atmosphere comprising a substrate of the entrapped enzyme and a product of the enzymatic reaction can be detected. In some embodiments, the product is detected directly, e.g., via detection of the product via chromatography (e.g. liquid chromatography (e.g., HPLC or TLC), gas chromatography, etc.), via an antibody-based method (e.g., ELISA), or via collection of a precipitated product. In some embodiments, the product of the enzyme or the enzymatic activity is detected indirectly, e.g., via a change in pH of the solution, a color change, fluorescence, luminescence, a change in temperature, or the evolution of a gas.

In some embodiments, the solid chitosan matrix material comprising the stably entrapped enzyme exhibits detectable enzyme activity after performing the catalytic function for a period of time. In some embodiments, when the biocatalyst functions for a time period that is about 5 times longer, about 10 times longer, about 20 times longer, about 50 times longer, or about 100 times longer or more, than an initially evaluated operational time period, the residual detectable catalytic activity is more than about 95%, more than about 90%, more than about 80%, more than about 70%, or more than about 50%, relative to the catalytic activity measured after the initial operational time period. For example, in some embodiments, the residual detectable catalytic activity is more than about 90% after 10 hours of performance compared to the catalytic activity detected after about 1 hour of performance. In another example, in some embodiments, the residual detectable catalytic activity is more than about 80% after 30 days of performance compared to the catalytic activity detected after about 1 day of performance. In another example, in some embodiments, the residual detectable catalytic activity is more than about 50% after 50 weeks of performance compared to the catalytic activity detected after about 1 week of performance.

In some embodiments, the at least one enzyme remains active and stably entrapped within the chitosan matrix after washing with water (e.g., alkaline water) or a mixture of water and a surfactant or soap. In some embodiments, the at least one enzyme remains active and stably entrapped within the chitosan matrix material after repeated washings (e.g., 2, 3, 4, 5, 6, 7, 8, 9, 10, 15, 20, 25, 50, or more washings). In some embodiments, the at least one enzyme remains active and stably entrapped within the chitosan matrix for at least about 2 months when the chitosan matrix material is dried and stored at room temperature. In some embodiments, the chitosan matrix material remains active and stably entrapped within the chitosan matrix for at least 3, 4, 5, 6, 7, 8, 9, 10, 11, or 12 months when dried and stored at room temperature. In some embodiments, the chitosan matrix material remains active and stably entrapped within the chitosan matrix for 1 year or more when the matrix is dried and stored at room temperature.

Any suitable enzyme or mixture of enzymes can be used as the at least one enzyme. The enzymes can include one or more oxidoreductase, one or more transferase, one or more hydrolase, one or more lyase, one or more isomerase, one or more ligase, or combinations thereof. Particular enzymes suitable for use according to the presently disclosed subject matter include, but are not limited to, aminopeptidase, amylase, glucoamylase, isoamylase, dextranase, glycogenase, pullulanase, beta-lactamase, anhydrase, carbonic anhydrase, carbohydrase, carboxypeptidase, catalase, cellulase, chitinase, chitosanase, heparinase, cutinase, glycosylase, pectinase, arabinofuranosidase, rhamnopyranosidase, glycosyltransferase, cyclodextrin glycosyltransferase, carboxylase, decarboxylase, ribulose-1,5-bisphosphate carboxylase/oxygenase (RuBisCO), hydrogenase, dehydrogenase, glucose-6-phosphate dehydrogenase, glutamate dehydrogenase, leucine dehydrogenase, pyruvate dehydrogenase, lactate dehydrogenase, alcohol dehydrogenase, deoxyribonuclease, glycosyl hydrolase, transglutaminase, glucose isomerase, esterase, tannase, acetylcholineesterase, acetyl hydrolase, polyesterase, alpha-galactosidase, beta-glucosidase, haloperoxidase, invertase, raffinase, lactase, beta-galactosidase, asparaginase, acylase, aminoacylase, pectin lyase, pectate lyase, alliinase, ammonia lyase, aspartate ammonia lyase, phenylalanine ammonia lyase, aspartase, penicillin amidase, nitrile hydratase, aminoacylase, laccase, lipase, *Candida antarctica* lipase A (CALA), *Candida antarctica* lipase B (CALB), phospholipase, lysozyme, mannosidase, hydratase, fumarase, tryptophanase, monooxygenase, kinase monooxygenase, luciferase, lytic polysaccharide monooxygenase (LPMO), nitrilase, oxidase, glucose oxidase, tyrosinase, urate oxidase, glutamate oxidase, lactate oxidase, choline oxidase, xanthine oxidase, cholesterol oxidase, sulfite oxidase, putrescine oxidase, oxygenase, nitrogenase, reductase, nitrate reductase, sulfotransferase, pectinolytic enzyme, peptidoglutaminase, peroxidase, peroxygenase, cytochrome oxidase, hydrogenase, phytase, phosphorylase, phosphatase, polyphenoloxidase, proteolytic enzyme, protease (e.g., a serine protease (e.g., Proteinase K), a cysteine protease, an aspartyl protease, or a metalloprotease), thermolysin, trypsin, chymotrypsin, pepsin, papain, bromelain, subtilisin A, creatine deaminase, ficain, hydantoinase, urease, arginase, phosphodiesterase, phosphotriesterase, nuclease, endonuclease, ribonuclease, transglutaminase, sulfatase, hexokinase, polymerase, synthase, synthetase, xylanase, xylosidase, and xyloglucan endotransglycosylase. In some embodiments, the enzyme has a molecular weight above about 15 kDa, above about 20 kDa, above about 30 kDa, above about 40 kDa, above about 50 kDa, above about 60 kDa, above about 70 kDa, above about 80 kDa, above about 90 kDa or above 100 kDa. In some embodiments, the enzyme is acid-sensitive and/or heat sensitive. In some embodiments, the enzyme is not a heat-resistant chitosan-degrading enzyme. In some embodiments, the enzyme is not a chitosan-degrading enzyme. In some embodiments, the enzyme is not a biofilm-degrading enzyme. In some embodiments, the enzyme is selected from catalase, carbonic anhydrase, luciferase, protease, trypsin, alpha-chymotrypsin, bromelain, penicillin amidase, amino-acylase, lactase, esterase, lipase, laccase, glucose oxidase, glucose isomerase, peroxidase, peroxygenase, glycosyl hydrolase, asparaginase, phosphodiesterase, phosphotriesterase, or beta-glucosidase. In some embodiments, cofactors or coenzymes are added, such as metal ions, vitamins, heme, pyridoxal phosphate, adenine nucleotides (e.g. ATP, ADP, AMP), nicotinamide or flavin adenine dinucleotides (e.g. NAD+, NADH, NADP+, NADPH, FAD, $FADH_2$), and coenzyme A. In some embodiments, prosthetic groups are added, such as porphyrin, optionally with a metal ion, optionally heme. In some embodiments, metal ions are added, such as ions of iron, magnesium, manganese, zinc, copper, nickel, vanadium, cadmium, calcium, potassium and sodium.

In some embodiments, whole cells comprising enzymes are entrapped in the compositions and by the methods of the present disclosure. In some embodiments, the entrapped whole cells are viable. In some embodiments, the whole cells are dormant, such as in the form of spores. In some embodiments the entrapped whole cells are not viable. In some embodiments, the non-viable cells have a compromised cell wall and/or cell membrane, optionally wherein the permeability of the compromised cell wall and/or cell membrane allows entry and/or exit of enzyme substrates and/or enzyme catalyzed reaction products, further optionally wherein the enzyme(s) remain entrapped in the solid matrix of the present disclosure. Without being bound by any particular theory or mechanism, entrapping whole cells and/or compromised whole cells by the embodiments of the present disclosure provides for intracellular and/or membrane bound enzymes to be used without carrying out isolation or purification steps and/or provides for intracellular and/or membrane bound enzymes to operate in their natural cellular environment. Furthermore, entrapping whole cells and/or compromised whole cells by the embodiments of the present disclosure provides for the cells to be exposed to and used at different conditions than those encountered in the natural environment, such as exposure elevated levels of one or more particular compounds and/or exposure to high or low temperatures and/or exposure to liquids comprising solvents, such as liquids comprising organic solvents.

In some embodiments, the presently disclosed materials can be prepared using mild conditions (e.g., without the use of pH conditions below about 2 or above about 12.5, without the use of a temperature above about 60° C., without the use of a strong acid, and/or without the use of a strong base (e.g., an alkali metal hydroxide)). In some embodiments, the method can include the use of an alkali metal hydroxide or an alkali metal alkoxide (e.g., in a coagulation solution). In some embodiments, the presently disclosed method can be free of the use of ultrasonication.

In some embodiments, the materials can be prepared without the use of glutaraldehyde as a covalent cross-linking agent. In some embodiments, the materials can be prepared without the use of glutaraldehyde or another aldehyde-containing covalent cross-linking agent (e.g., formaldehyde, succinaldehyde, or another aldehyde or dialdehyde). In some embodiments, the materials can be prepared without the use of a poly(carboxylic acid) cross-linking agent. In some embodiments, the materials can be prepared without the use of a covalent cross-linking agent selected from glyoxal, tris(hydroxymethyl)phosphine, a carbodiimide, epichlorohydrin, and/or NHS. In some embodiments, the materials can be prepared without the use of glutaraldehyde together with hexamethylenediamine or ethylenediamine (or another diamine). In some embodiments, the materials can be prepared without the use of a covalent cross-linking agent of any type. In some embodiments, the cross-linking free method is further free of the use of collagen and/or is a method wherein the at least one enzyme is an acid-sensitive and/or a heat-sensitive enzyme.

In some embodiments, the methods provided herein are free of the use of a covalent cross-linking agent reacted with the chitosan prior to, during or both prior to and during the formation of the solid chitosan/enzyme matrix. In some embodiments, the solid chitosan/enzyme matrix can be contacted with a covalent cross-linking agent after formation of the solid chitosan/enzyme matrix, e.g., to cross-link the chitosan to form a more stable matrix. In some embodiments, the chitosan/enzyme matrix can be contacted with a reactive group or covalent cross-linking agent that is covalently bound to a solid support, such as a textile material, e.g., to covalently bind the chitosan/enzyme matrix to the solid support.

In some embodiments, the materials can be prepared without the use of an additional polyanion selected from alginate, carrageenan, or xanthan. In some embodiments, the materials can be prepared without the use of a polyphosphate or organic sulfate polyanion. In some embodiments, the materials can be prepared without the use of an additional polyanion (i.e., a polyanion other than the enzyme or enzymes being entrapped within the chitosan matrix). In some embodiments, the materials can be prepared with the use of an anionic dyestuff, but without the use of any other polyanion. In some embodiments, the additional polyanion free method is further free of the use of collagen and/or is a method wherein the at least one enzyme is an acid-sensitive and/or a heat-sensitive enzyme.

In some embodiments, the presently disclosed materials can be made in the presence of an additional cationic component, i.e., a cationic molecule or polymer other than the protonated chitosan, such as, but not limited to, polyethyleneimine. In some embodiments, a covalent cross-linking agent can be added to the chitosan/enzyme solution. In some embodiments, the covalent cross-linking agent is selected from a triazine (e.g., trichlorotriazine or dichlorotriazine) and dimethylol dihydroxy ethylene urea (DMDHEU) or an analog thereof.

In some embodiments, the presently disclosed materials can be prepared in the presence of an additional polyanion, e.g., carboxymethyl cellulose, carboxymethylchitosan, hyaluronan, heparin, poly(aspartic acid), poly(glutamic acid), poly(acrylic acid), or poly(methacrylic acid), which in some embodiments, can be added after solidification of the chitosan in the chitosan/enzyme solution.

In some embodiments, the solid chitosan matrix material comprising the at least one stably entrapped enzyme can be further treated or derivatized to alter one or more material properties. For example, the material can be treated to enhance or add one or more of the group including, but not limited to, hydrophilicity, hydrophobicity, antifouling activity, antibiotic activity, adhesiveness, flame retarding properties, and color. For instance, in some embodiments, the further treatment comprises adding color to the solid chitosan matrix material, e.g., by adding a dye, pigment, or other coloring agent to the chitosan/enzyme solution or treating a solid chitosan matrix material comprising at least one stably entrapped enzyme with a solution comprising a dye, pigment, or other coloring agent, such as by coating the solid chitosan matrix material with the solution comprising the coloring agent or submersing the solid chitosan matrix material in the solution comprising the coloring agent. In some embodiments, the further treatment comprises adding a flame retardant or antibiotic agent to the chitosan/enzyme solution or treating the solid chitosan matrix material with a solution comprising a flame retardant or antibiotic agent. In some embodiments, the hydrophilicity or hydrophobicity of the solid chitosan matrix material can be modified by derivatization of groups on the surface of the solid chitosan matrix material.

In some embodiments, the presently disclosed methods provide for the recovery and reuse or sustainable disposal of the enzymes. In some embodiments, the chitosan matrix material comprising the stably entrapped enzyme can be redissolved or degraded at a later point in time, such as by exposure to low pH, to biological materials (such as enzymes or microorganisms that can degrade the chitosan) or to chemical agents (e.g., oxidizers). This feature can, for example, provide for applications wherein the chitosan-enzyme coating is (1) delivered to a particular location while in liquid form, (2) solidified onto the substrate in that location by raising the pH or evaporating the water from the coating material, (3) utilized as a biocatalytic coating while in the solidified form, and (4) removed by lowering the pH to dissolve and wash away the biocatalytic coating after a period of time, for example, after a period of time when the biocatalytic performance has diminished due to inactivation, contamination, or another factor. In this way, the biocatalytic coating can be reloaded (or renewed) using a sequence of alternating acidic and alkaline liquid treatments. The biocatalytic coating can also be delivered to locations that are most easily accessible by or that are exclusively accessible via liquid flow. For example, the sequence of treatment can be used to coat the internal surfaces of a complex packing material, to give the packing material biocatalytic functionality that can be easily regenerated. In some embodiments, the chitosan matrix comprises derivatized chitosan, and the derivatized chitosan is optionally degraded by exposure to a derivatized-chitosan-degrading enzyme.

IV. Compositions

In some embodiments, the presently disclosed subject matter provides a chitosan matrix material prepared according to a method as described herein, wherein said chitosan matrix material comprises a solid chitosan matrix wherein at least one enzyme is stably entrapped (e.g., non-covalently entrapped) within the solid chitosan matrix. In some embodiments, the at least one enzyme is not a chitosan degrading enzyme. In view of the mild conditions employed by the presently disclosed methods, in some embodiments, the at least one enzyme is not a heat resistant enzyme. In some embodiments, the material is free of collagen. In some embodiments, the material is free of a covalent cross-linking agent or a group derived therefrom and/or an additional polyanion (i.e., a polyanion other than the at least one enzyme). In some embodiments, the at least one enzyme is an acid- and/or a heat-sensitive enzyme. In some embodiments, the matrix material has a mass ratio of chitosan to enzyme (on a dry basis) of more than about 0.5 (e.g., more than about 0.5, 1, 1.5, 2, 2.5, 3, 3.5, 4, 4.5, 5, 7.5, 10, 15, or more than about 20). In some embodiments, the mass ratio of chitosan to enzyme is more than about 2. In some embodiments, the mass ratio of chitosan to enzyme is more than about 5 (e.g., about 6, 7, 8, 9, 10, 15, 20, 25, 50, 75, 100, 250, 500, or 1000).

The at least one enzyme can be any suitable enzyme or mixture of enzymes. The enzymes can include, for instance, one or more oxidoreductase, one or more transferase, one or more hydrolase, one or more lyase, one or more isomerase, one or more ligase, or combinations thereof. In some embodiments, the at least one enzyme is selected from the group including, but not limited to, catalase, carbonic anhydrase, peroxidase, glucose oxidase, LPMO, glucose isomerase, beta-glucosidase, phosphotriesterase, phosphodiesterase, urease, nitrile hydratase, luciferase, laccase, lipase, CALA, CALB, cutinase, protease, bromelain, subtilisin A, chymotrypsin, and trypsin.

In some embodiments, the solid chitosan matrix can also comprise one or more other additives, such as, but not limited to, one or more coloring agents (e.g., one or more dye, pigment, or other coloring agent), a flame retardant, an antibiotic, and an antifouling agent. In some embodiments, for example, the solid chitosan matrix material can comprise at least two different coloring agents, which are present at two different locations in the matrix material, and which can indicate the presence of two different enzymes or enzyme mixtures at the two different locations.

In some embodiments, the chitosan matrix material is provided in the form of a fiber. Accordingly, in some embodiments, the presently disclosed subject matter provides a fiber comprising a solid chitosan matrix material, wherein the solid chitosan matrix material further comprises at least one enzyme stably entrapped within the solid chitosan matrix material. In some embodiments, the at least one enzyme is not a heat-resistant chitosan-degrading enzyme. In some embodiments, the at least one enzyme is not a chitosan-degrading enzyme. In some embodiments, the matrix material is free of collagen.

In some embodiments, the fiber is free of one or more of a covalent cross-linking agent, alginate, and an added polyanion. In some embodiments, the matrix material of the fiber comprises a mass ratio of enzyme to chitosan (on a dry basis) or less than about 1. In some embodiments, the mass ratio of enzyme to chitosan is less than about 0.5. In some embodiments, the mass ratio of enzyme to chitosan is less than about 0.25. In some embodiments, the chitosan matrix material comprises a mass ratio of chitosan to enzyme (on a dry basis) of greater than about 0.5. In some embodiments, the mass ratio of chitosan to enzyme is greater than about 2 or greater than about 5.

In some embodiments, the at least one enzyme remains active and stably entrapped within the chitosan matrix after repeated washings (e.g., 2, 3, 4, 5, 6, 7, 8, 9, 10, 15, 20, 15, 50 or more washings) of the composition with water (e.g., alkaline water) or with soap and water. In some embodiments, the repeated washings further comprise mechanical agitation. Thus, for example, the at least one enzyme remains active after repeated washings of the presently disclosed fibers or materials comprising said fibers in a washing machine (e.g., a front- or top-loading washing machine intended for residential or commercial use). In some embodiments, the at least one enzyme remains active and stably entrapped within the chitosan matrix for a period of at least about 2 months (e.g., at least about 2, 3, 4, 5, 6, 7, 8, 9, 10, 11, or about 12 months) when the fiber is dried and stored at room temperature.

The at least one enzyme can be any suitable enzyme or enzyme mixture as described hereinabove. The enzymes can include, for instance, one or more oxidoreductase, one or more transferase, one or more hydrolase, one or more lyase, one or more isomerase, one or more ligase, or combinations thereof. In some embodiments, the at least one enzyme is selected from the group including, but not limited to, catalase, carbonic anhydrase, peroxidase, glucose oxidase, LPMO, glucose isomerase, beta-glucosidase, phosphotriesterase, phosphodiesterase, urease, nitrile hydratase, luciferase, laccase, lipase, CALA, CALB, cutinase, protease, bromelain, subtilisin A, chymotrypsin, and trypsin. In some embodiments, the at least one enzyme is protease, catalase, or carbonic anhydrase.

In some embodiments, the presently disclosed subject matter provides a coated object comprising a substrate and a coating layer, wherein the coating layer comprises a solid chitosan matrix material, wherein the solid chitosan matrix material comprises at least one active enzyme, wherein the at least one active enzyme is stably entrapped (e.g., non-covalently entrapped) within the chitosan matrix material. Thus, the coated object comprises a substrate and a biocatalytic coating comprising the solid chitosan matrix material. The use of inexpensive substrates for the biocatalytic coating is desirable for economic reasons. The use of inexpensive substrates that can be constructed, shaped and bent in different forms and sizes is also desirable for some applications. Textile materials, such as fibers, yarns, and fabrics, are some examples of such materials. Various coating technologies are well known in the art of textile processing and can be adapted for use according to the presently disclosed subject matter.

In some embodiments, the substrate of the coated object is a flexible substrate, such as, but not limited to, a paper, a fiber, a yarn, a ribbon, a rope, a fabric, or a textile. Thus, in some embodiments, the presently disclosed subject matter provides a coated flexible substrate wherein the flexible substrate is partially or completely coated with a coating layer comprising a solid chitosan matrix material, wherein the solid chitosan matrix material comprises at least one active enzyme, wherein the at least one active enzyme is stably entrapped within the chitosan matrix material. The flexible substrates can comprise natural or synthetic polymers. In some embodiments, the flexible substrate can be selected from a woven fabric, a non-woven fabric, a knitted fabric, or any combination of such fabrics. In some embodiments, the coating layer is free of one or more of an aldehyde-containing cross-linking agent and an additional polyanion. In some embodiments, the flexible substrate is free of a separate treatment to increase the interaction of the chitosan and the substrate. In some embodiments, the coating layer is free of any type of covalent cross-linking agent.

In some embodiments, the chitosan matrix material comprises a mass ratio of chitosan to enzyme (on a dry basis) of greater than about 0.5. In some embodiments, the mass ratio of chitosan to enzyme is greater than about 2 or greater than about 5.

In some embodiments, the coating layer can further comprise solid, optionally inert, particles, e.g., to increase the surface area of the coating layer. In some embodiments, the solid, optionally inert, particles are microporous particles. Suitable solid, optionally inert particles include, but are not limited to microparticles, nanoparticles, nanofibers, microfibers, or combinations thereof. In some embodiments, the solid, optionally inert, particles are selected from microcrystalline polymers, microcrystalline cellulose, microcrystalline chitosan, microcrystalline chitin, silica powder, diatomaceous earth, magnetite, activated carbon particles, and activated carbon fibers. In some embodiments, the particles can comprise xerogel biocatalyst particles, e.g., prepared from a chitosan/enzyme solution. Additional particles for use herein include powders and/or particles of chitin and chitosan, crushed bone, crushed shells, and hemp hurd. In some embodiments, particles can be prepared by spraying a dry enzyme solution with a porous powder, and then the porous powder-enzyme can be entrapped in a chitosan matrix coating layer.

In some embodiments, the flexible substrate comprises one of the group comprising cotton, rayon, lyocell, jute, linen, hemp, ramie, wool, silk, soy, collagen, fibroin, a product derived from protein, polyester, nylon, polyether ether ketone (PEEK), glass fiber, polyethylene terephthalate, polyurethane, acrylic, modacrylic, silicone, cellulose, man-made cellulosics, cellulose acetate, microbial cellulose, chitosan, chitosan acetate, chitin, wood, a product derived from wood, and combinations thereof. In some embodiments, the flexible substrate is biodegradable. In some embodiments, the flexible substrate comprises cellulose. For example, the flexible cellulose substrate can comprise paper, a cotton fiber, a cotton yarn, a cotton fabric, rayon, lyocell, modal, man-made cellulosics, or a microbial cellulose. In some embodiments, the flexible substrate comprises chitosan, chitin, chitan, a derivative of chitosan, chitin or chitan, or a combination thereof. In some embodiments, the chitosan is a non-animal derived chitosan. In some embodiments, the chitosan is a fungal chitosan. In some embodiments, the fungal chitosan is *R. oryzae* chitosan.

In some embodiments, wherein the flexible substrate is a pretreated flexible substrate. For instance, in some embodiments, wherein the flexible substrate is pretreated with oxidation, irradiation, or ozonation prior to coating with the coating layer. In some embodiments, the irradiation is performed with ultraviolet, gamma, plasma, laser, microwave, electron beam or ion beam irradiation.

In some embodiments, the flexible substrate comprises plastic or a composite material. In some embodiments, the flexible substrate has a complex three-dimensional shape and the coating layer coats at least a portion of a surface of the substrate. In some embodiments, the coating layer conformally or substantially conformally coats the at least one portion of the surface of the substrate. In some embodiments, the coating layer coats a surface comprising one face or side of the substrate. In some embodiments, the coating layer coats both the top and bottom face and/or all faces/surfaces of the substrate.

The coating layer can include any suitable enzyme or mixture of enzymes. The enzymes can include, for instance, one or more oxidoreductase, one or more transferase, one or more hydrolase, one or more lyase, one or more isomerase, one or more ligase, or combinations thereof. In some embodiments, the at least one active enzyme is catalase or carbonic anhydrase. In some embodiments, the at least one active enzyme is selected from the group including, but not limited to, peroxidase, glucose oxidase, LPMO, glucose isomerase, beta-glucosidase, phosphotriesterase, phosphodiesterase, urease, nitrile hydratase, luciferase, laccase, lipase, CALA, CALB, cutinase, catalase, carbonic anhydrase, protease, bromelain, subtilisin A, chymotrypsin, and trypsin.

V. Applications

In some embodiments, the presently disclosed subject matter provides a biocatalytic material comprising a chitosan matrix material and one or more active enzyme stably entrapped (e.g., non-covalently entrapped) therein, e.g., using a method as described herein. The biocatalytic materials of the presently disclosed subject matter can be used in a wide variety of applications, including, but not limited to industrial gas separation, controlled gas production, chemical conversion, agriculture, waste treatment, water treatment, decontamination, reactive packaging, medical or veterinary applications, and analytical or diagnostic test kits. Industrial gas separation, for example, can include removal of carbon dioxide from a gas mixture by selective reaction of carbon dioxide with water to form bicarbonate in the presence of carbonic anhydrase. Controlled gas production can include generation of oxygen gas from hydrogen peroxide in the presence of catalase, and can include the generation of carbon dioxide and ammonia gas from urea in the presence of urease. Chemical conversion can include stereospecific resolution of enantiomers, such as use of alpha-chymotrypsin for selective hydrolysis of ester enantiomers. Agriculture, waste treatment, water treatment or decontamination applications can include conversion of pesticides, chemical warfare agents, or other toxic compounds to less harmful compounds, such as use of phosphotriesterase to degrade organophosphonates, such as sarin, cyclosarin, soman, and nerve agents VX and VR. Without being bound by any particular mechanism, enzyme catalyzed decontamination reactions can occur by oxidation, hydrolysis or nucleophilic substitution of the harmful compounds directly, and/or can facilitate these reactions by catalyzing the decomposition of binders or thickening agents associated with the harmful compounds, and/or can facilitate the removal, or 'cleaning,' of the harmful compounds by facilitating the decomposition of binders or thickening agents associated with the harmful compounds. For instance, in some embodiments, the binders or thickening agents comprise polysaccharides capable of being degraded by hydrolytic, lyase or oxidase enzymes. In some embodiments, a fabric comprising the biocatalytic materials of the presently disclosed subject matter, further comprising one or more enzymes capable of converting harmful compounds to less harmful compounds, is placed over an area contaminated with the harmful compounds in a way that causes the harmful compounds to be converted to less harmful compounds, and/or that causes the harmful compounds to be loosened or released from the contaminated area, and the fabric is then optionally contacted, pressed, blotted, wiped and/or moved across the surface in a manner that causes the harmful compounds and/or degraded compounds to be removed from the contaminated area, such as by being absorbed in, adsorbed to, or adhered to the fabric. In some embodiments, the fabric comprising the harmful and/or degraded compounds can then be safely disposed.

The presently disclosed biocatalytic materials, such as the materials comprising coated substrates, can be used in batch reactors, as well as in semi-continuous and continuous flow reactors, wherein the biocatalytic material is held in one zone of the reactor, while reactants flow past in the process of carrying out chemical conversions.

In some embodiments, the presently disclosed subject matter provides a biocatalyst system comprising a flexible, wettable substrate, such as, but not limited to a textile, fiber, ribbon, rope or yarn, wherein said substrate comprises or is coated with one or more layer of a solid chitosan matrix material, wherein the solid chitosan matrix material further comprises an active enzyme entrapped therein. In some embodiments, the solid chitosan matrix material comprises a mass ratio of chitosan to enzyme (on a dry basis) of greater than about 0.5, greater than about 2, or greater than about 5. In some embodiments, the enzyme is not a heat-resistant, chitosan-degrading enzyme. In some embodiments, the enzyme is not a chitosan-degrading enzyme. In some embodiments, the matrix material is free of a covalent cross-linking agent and/or an additional polyanion. In some embodiments, the matrix material is free of collagen and/or the solid chitosan matrix material comprises more than one type of active enzyme entrapped therein.

In some embodiments, the substrate is non-covalently coated with one or more layer of the solid chitosan matrix material. In some embodiments, the flexible, wettable substrate comprises a biodegradable material. In some embodiments, the substrate is a textile, fabric, rope, ribbon, or yarn comprising a material selected from the group comprising cotton, boiled off cotton, scoured cotton, unbleached cotton, bleached cotton, mercerized cotton, unbleached linen, bleached linen, spun silk, manufactured silk, spun viscose, lyocell, wool, worsted wool, and combinations thereof.

In some embodiments, the biocatalyst system is adapted for use in a medical or veterinary application. For example, the biocatalyst system can be adapted for use in wound healing, in an artificial lung, or in blood dialysis. In some embodiments, the biocatalyst system is adapted for use in a pre- or post-harvest agricultural application, such as, but not limited to applications related to geotextiles, ground cover, soil decontamination, soil amendment, seedling containers, seed wrappers, seed containers, plant support systems, and produce packaging. In some embodiments, the biocatalyst system is adapted for use in a water treatment application. In some embodiments, the water treatment application is selected from water purification or water decontamination. In some embodiments, the water being treated is selected from the group including, but not limited to, industrial process water, produced water, agronomy water, horticulture water, water used in livestock production, water used in aquaculture, water used in aquariums, water used in algae production, municipal water, household water, and environmental water.

In some embodiments, the presently disclosed subject matter provides a method of catalyzing a reaction using a biocatalyst system of the presently disclosed subject matter. In some embodiments, the method comprises placing a biocatalyst system into contact with a solution or gas comprising an enzyme substrate, wherein the biocatalyst system comprises a flexible, wettable substrate, wherein said flexible, wettable substrate is coated with one or more layer of a solid chitosan matrix material, and wherein the solid chitosan matrix material further comprises an active enzyme entrapped therein. In some embodiments, the solution comprising the enzyme substrate is an aqueous solution. In some embodiments, e.g., when the enzyme substrate is contacted to the biocatalyst system in a gas, the biocatalyst system can be further contacted with a liquid into which the enzyme substrate and/or a product of an enzyme-catalyzed reaction can dissolve, e.g., to aid in transport of the substrate or product within or through the flexible, wettable substrate of the biocatalyst system. In some embodiments, the flexible, wettable substrate of the biocatalyst system comprises a material such as, but not limited to, cotton, linen, viscose, silk, wool, polyamide, polyester and combinations thereof. In some embodiments, the flexible, wettable substrate comprises cotton yarn or cotton fabric.

In some embodiments, the solution comprising the enzyme substrate or a solution comprising an enzyme-catalyzed reaction product is transferred from one portion of the biocatalyst system to another part of the biocatalyst system via transport in or through the flexible wettable substrate of the biocatalyst system. For instance, the transport can involve wicking, i.e., wherein the flexible wettable substrate has the ability to move the solution via absorption and capillary action. In some embodiments, the wicking can be enhanced by gravity.

In some embodiments, placing the biocatalyst system into contact with the solution or gas comprising the enzyme substrate comprises: (a) placing one end or portion of the flexible, wettable substrate of the biocatalyst system in contact with the solution or gas comprising the enzyme substrate, wherein said solution or gas is in a first container or a first process zone; and (b) placing a second end or portion of the flexible wettable substrate of the biocatalyst system into a second container or a second process zone. The enzyme substrate can be absorbed into the biocatalyst system in the first process zone and transformed into a product by a reaction catalyzed by the at least one active enzyme entrapped therein. In some embodiments, e.g. when the enzyme substrate is provided in a solution, the reaction can be catalyzed as the solution moves from the first container or first process zone to the second container or second process zone through the wettable material of the catalyst system. In some embodiments, catalyzing the reaction promotes a desirable chemical transformation. For example, in some embodiments, catalyzing the reaction decontaminates the solution comprising the enzyme substrate by converting an undesirable and/or toxic compound into a more desirable or less toxic compound.

In some embodiments, the second container or second process zone is present at a location closer to the ground than the first container or first process zone or the solution comprising the enzyme substrate is transported against or approximately perpendicular to gravity by wicking or capillary action. For example, FIG. 1 shows a schematic diagram wherein biocatalyst system (e.g., chitosan-entrapped enzyme yarn) 3 comprising has a first end which is placed in enzyme substrate solution 2 in first/originating container 1. Liquid absorbed from enzyme substrate solution 2 can travel in direction 4 through biocatalyst system (e.g., coated yarn) 3 via gravity assisted wicking to second/receiving container 5, which is positioned lower than first/originating container 1. Transported liquid 6 collecting in second/receiving container 5 can contain the product of an enzymatic reaction. FIG. 2 shows a schematic diagram where first end 7 of biocatalyst system (e.g., coated yarn) 3 is held above second/receiving container 5 and enzyme substrate solution 2 from first/originating container 1 is applied to end 8 of first end 7. Transported liquid 6 that collects in second/receiving container 5 after transport through biocatalyst system (e.g., coated yarn) 3 in direction 4 can comprise an enzyme-catalyzed product.

In some embodiments, placing the catalyst system into contact with the solution or gas comprising the enzyme substrate comprises: (a) contacting the flexible, wettable substrate of the biocatalyst system with a solution or gas comprising the enzyme substrate in a first process zone to absorb the enzyme substrate into the flexible, wettable substrate and to catalyze a reaction to convert the enzyme substrate into a product; (b) transferring the flexible, wettable material to a second process zone; and (c) releasing a solution or gas comprising the product from the flexible, wettable material. Thus, the biocatalyst system can be used both as a catalyst and as a conveyor to transport compounds (e.g., enzyme-catalyzed products) from one location to another. In some embodiments, the releasing is performed by rinsing and/or pressing the wettable material. In some embodiments, the releasing is performed under vacuum or via the application of heat (e.g., to cause a reaction product to evaporate from a liquid wetting the flexible, wettable substrate). In some embodiments, catalyzing the reaction decontaminates the solution or gas comprising the enzyme substrate by converting an undesirable and/or toxic compound into a more desirable or less toxic compound. In some embodiments, the contacting is performed by spraying the solution comprising the enzyme substrate onto the wettable substrate or wherein the contacting is performed by dipping the wettable substrate into the solution comprising the enzyme substrate.

In some embodiments, the wettable substrate of the catalyst system comprises a fabric looped over a series of drive rollers, wherein action of the drive rollers passes the fabric sequentially through the first reaction zone and the second reaction zone. In some embodiments, action of the drive rollers continuously passes the fabric sequentially through the first reaction zone and the second reaction zone.

In some embodiments, the biocatalyst system forms a tandem or cascade reactor. For example, in some embodiments, the biocatalyst system can comprise different enzymes stably entrapped in a chitosan matrix material wherein the different enzymes (e.g., each of the different enzymes or different combinations of enzymes) are positioned at different locations in or along the wettable substrate. In some embodiments then, a first enzyme substrate is converted to a first product by interaction with a first enzyme at a first location along the wettable substrate and the first product is subsequently converted to a second product by interaction with a second enzyme at a second location along the wettable substrate, wherein the first product comes into contact with the second enzyme by flowing in solution or in a gas flow from the first location along the wettable substrate to the second location along the wettable substrate.

In some embodiments, the wettable substrate of the catalyst system is interlaced or stacked with a non-wettable material to confine or direct liquid flow of the enzyme solution. In some embodiments, the interlacing or stacking creates space around the wettable substrate, in which, optionally a flow of gas or establishment of a vacuum can occur. In some embodiments, the flow of gas comprises an enzyme substrate and or a product of a reaction catalyzed by the biocatalyst system.

In some embodiments, the biocatalyst system itself confines or directs the liquid flow of the enzyme solution. For example, in some embodiments, the biocatalyst system provides enhanced containment of the solution in the flexible wettable substrate compared to the same flexible, wettable material in the absence of the one or more layer of solid chitosan matrix material. For instance, the biocatalyst system can exhibit less dripping or other loss of a solution wetting the flexible, wettable substrate than the corresponding, uncoated flexible, wettable substrate. In some embodiments, the solution wetting the flexible, wettable substrate remains more confined within individual fibers of the flexible, wettable substrate than if the solid chitosan coating layer was absent, resulting in less collection or adherence of the solution at the surface of the fibers and/or in areas between individual fibers of the flexible, wettable substrate. Thus, in some embodiments, the coating layer provides increased interfacial area between a liquid absorbed within the flexible, wettable substrate of the biocatalyst system and a surrounding gas. This increased area can provide more efficient molecular mass transfer and improved reaction efficiency for gas-liquid reactions.

In some embodiments, the presently disclosed subject matter can provide an easily replenishable coating for applying enzymes, such as carbonic anhydrase, in carbon dioxide gas separation reactors or devices. In these reactors, the processing conditions typically operate at elevated pH, where the solid chitosan material is stable. During process shutdown, a low pH wash can be used to remove spent chitosan/enzyme biocatalyst from the system and fresh chitosan/enzyme biocatalyst can be applied in solution form to regenerate the coating inside the gas separation reactor. Alternatively, another type of wash treatment (e.g., a chemical (e.g. an oxidizing agent) or an enzyme-catalyzed wash that accelerates the degradation of the chitosan-based coating, e.g., including chitosanase) can be used to remove spent biocatalyst from the reactor. These approaches take advantage of the solubility, stability, and degradability of the chitosan polymer under different controllable conditions and are not limited to use in a gas separation reactor.

Accordingly, in some embodiments, the presently disclosed subject matter provides a carbon dioxide filter, wherein the carbon dioxide filter comprises a chitosan matrix material and an active carbonic anhydrase, wherein the active carbonic anhydrase is stably entrapped (e.g., non-covalently entrapped) in the chitosan matrix material. In some embodiments, the filter is free of a covalent cross-linkage based on glutaraldehyde or another aldehyde. In some embodiments, the filter is free of alginate.

In some embodiments, the chitosan matrix material of the filter is in the form of a fiber, yarn, rope, ribbon, fabric or textile. In some embodiments, the filter further comprises a substrate coated with one or more layer of the chitosan matrix material, wherein the filter is free of a covalent linkage between the substrate and the chitosan matrix material. In some embodiments, the substrate is a biodegradable substrate, such as, but not limited to, a substrate comprising a polysaccharide, cellulose, chitin, chitosan, starch, a polyamide, a protein, a polyester, or a combination thereof. In some embodiments, the biodegradable substrate comprises one or more of a fiber, a yarn, a ribbon, a rope, a fabric, or a textile.

In some embodiments, the chitosan matrix material is removable from the substrate via contact with an aqueous acidic solution having a pH of about 4.5 or less (e.g., a pH of about 3.5 or less, or a pH of about 2 or less), or via contact with a solution comprising an oxidizing agent or a chitosan-degrading enzyme. In some embodiments, the carbon dioxide filter is renewable by (i) application of an aqueous chitosan solution comprising chitosan and carbonic anhydrase to the substrate, and (ii) solidification of the aqueous chitosan solution to form a solid chitosan matrix material, wherein the carbonic anhydrase is stably entrapped in the solid chitosan matrix material. In some embodiments, the aqueous chitosan solution has a pH between about 2.0 and about 5.5 (e.g., a pH between about 2.5 and about 5.5 or a pH between about 3.5 and about 5.5). In some embodiments, the aqueous chitosan solution comprises at least about 1 milligrams (mg) of chitosan per milliliter (mL) of solution (e.g., about 1 mg/mL, 1.5 mg/mL, 2 mg/mL, 2.5 mg/ml, 3 mg/mL, 3.5 mg/ml, 4 mg/mL. 4.5 mg/mL, about 5 mg/mL, about 7.5 mg/mL, about 10 mg/mL, about 12.5 mg/mL, about 15 mg/mL, or about 20 mg/m L). In some embodiments, the aqueous chitosan solution comprises at least about 5 mg of chitosan per mL of solution. In some embodiments, the aqueous chitosan solution comprises at least about 10 mg of chitosan per mL of solution. In some embodiments, the carbon dioxide filter is removable via contact with an aqueous acidic solution (e.g., having a pH of about 4.5 or less, about 3.5 or less or about 2.0 or less) or via contact with a solution comprising an oxidizing agent or a chitosan-degrading enzyme, and the carbon dioxide filter can be renewed by (i) providing an aqueous chitosan solution comprising chitosan and carbonic anhydrase, wherein the aqueous chitosan solution has a pH between about 2.0 and about 5.5 (e.g., wherein the aqueous chitosan solution comprises at least about 1 mg of chitosan per mL of solution); and (ii) solidification of the aqueous chitosan solution to form a solid chitosan matrix material, wherein the carbonic anhydrase is stably entrapped in the solid chitosan matrix material.

In some embodiments, the filter comprises at least about 5 mg of carbonic anhydrase per gram of chitosan (e.g., about 5, 7.5, 10, 12.5, 15, 10, 25, 30, 35, 40, 45, 50, 60, 75, 100, 125, 150, 175, 200, or about 250 mg of carbonic anhydrase per gram of chitosan). In some embodiments, the filter comprises, at least about 10 mg of carbonic anhydrase per gram of chitosan. In some embodiments, the filter comprises at least about 50 mg of carbonic anhydrase per gram of chitosan or at least about 100 mg of carbonic anhydrase per gram of chitosan.

In some embodiments, the filter can be used to selectively remove carbon dioxide from a gas or liquid mixture. In some embodiments, the filter is a component of a gas scrubber, such as a gas scrubber of a coal or natural gas burning power plant. Thus, in some embodiments, the filter can be used to selectively remove carbon dioxide from a combustion gas mixture. In some embodiments, the filter is a component of a biogas upgrading apparatus, a rebreathing apparatus, or an air conditioning apparatus. In some embodiments, the filter can be used to remove carbon dioxide from air in an enclosed environment, such as a submarine, an airplane or a spacecraft. In some embodiments, the filter can be used to remove carbon dioxide from an industrial gas mixture, such as during fertilizer production. In some embodiments, the filter can be used to selectively remove carbon dioxide from blood, such as during blood dialysis, for use in an artificial lung. In some embodiments, the filter can be used to upgrade biogas (i.e., to remove carbon dioxide from biogas so that the remaining methane can be more readily used as a fuel source).

Accordingly, in some embodiments, the presently disclosed subject matter provides a method of upgrading biogas. In some embodiments, the method comprises contacting biogas with a carbon dioxide filter of the presently disclosed subject matter. The biogas can be gas resulting from the anaerobic digestion or fermentation of organic matter, such as agricultural waste/residues, municipal waste, food waste, and/or manure. Typically, biogas comprises mainly methane and carbon dioxide and upgrading it (i.e., to remove carbon dioxide) results in a more desirable fuel source. In some embodiments, the carbon dioxide filter comprises a supporting surface coated with a layer of solid chitosan matrix material, wherein an active carbonic anhydrase is stably entrapped within the solid chitosan matrix material.

In some embodiments, the carbon dioxide filter is renewable after a period of time in use, wherein renewing the carbon dioxide filter comprises: (i) contacting the carbon dioxide filter with an aqueous acidic solution (e.g., having a pH of about 4.5 or less, a pH of about 3.5 or less or a pH of about 2.0 or less) or with a solution comprising an oxidizing agent or a chitosan-degrading enzyme, thereby dissolving or depolymerizing the chitosan matrix material of the carbon dioxide filter; (ii) providing an aqueous acidic solution comprising chitosan and carbonic anhydrase to the substrate, wherein the aqueous acidic solution has a pH between about 2.0 and about 5.5 (e.g., a pH of between about 3.5 and about 5.5) and wherein the aqueous solution comprises at least about 1 milligrams of chitosan per milliliter of solution; and (iii) solidifying the aqueous solution comprising chitosan and carbonic anhydrase to form a solid chitosan matrix material, wherein the carbonic anhydrase is stably entrapped in the solid chitosan matrix material. In some embodiments, the method further comprises washing the substrate after step (i) and prior to step (ii).

In some embodiments, the filter can be used to selectively remove hydrogen peroxide from a liquid mixture, such as for bleach clean-up during textile wet processing, to eliminate excess hydrogen peroxide from industrial cleaning liquids prior to liquid recycling or discharge, or to create a barrier that can prevent hydrogen peroxide egress from a confined treatment area. In some embodiments, the hydrogen peroxide filter comprises a supporting surface coated with a layer of solid chitosan matrix material, wherein an active catalase is stably entrapped within the solid chitosan matrix material. In some embodiments, the hydrogen peroxide filter provides continuous hydrogen peroxide decomposition for water recycling.

In some embodiments, the filter can be used to generate oxygen from the decomposition of hydrogen peroxide catalyzed by catalase that is stably entrapped within the solid chitosan matrix material. In some embodiments, the decomposition of hydrogen peroxide to produce oxygen can increase the dissolved oxygen concentration of a liquid, such as for aerating an oxygen depleted environment.

In some embodiments, the presently disclosed subject matter can be used to incorporate protease enzymes for wound debridement in wound healing (e.g., burn wounds) applications. In such applications, the chitosan matrix material can work synergistically with the entrapped enzyme, due to the bioadhesive properties of chitosan, which can promote blood clotting, and can reduce the level of fibrin during healing to reduce the formation of scar tissue. See e.g., WO 2008/157318, incorporated herein by reference in its entirety. In addition, indigenous enzymes in the body (e.g., lysozyme) can gradually degrade the chitosan polymer, releasing the protease debridement enzyme into the wound area, providing a controlled release aspect. Accordingly, a coating of protease-containing chitosan on a wound dressing substrate (e.g., a bandage or a surgical gauze) can provide multiple benefits, keeping the wound clean and protected, while assisting with wound healing. In some embodiments, lysozyme can be entrapped in the chitosan polymer, and can participate in degrading the chitosan coating of the wound dressing, making it easier to remove the dressing without reopening the wound. The clean and mild pH preparation process of the presently disclosed subject matter provides a dressing that is free of harsh chemical residues that could further damage the wound. In some embodiments, therapeutic, digestive, and/or antimicrobial enzymes can be incorporated into materials for medical and/or veterinary applications.

Accordingly, in some embodiments, the presently disclosed subject matter provides a wound dressing, an implantable medical device, or a cosmetic wipe comprising a solid chitosan matrix material, wherein the solid chitosan matrix material comprises an active enzyme, and wherein the active enzyme is stably entrapped within the solid chitosan matrix material. In some embodiments, the chitosan matrix material is free of a covalent cross-linking agent and/or an additional polyanion. In some embodiments, the enzyme is not a heat-resistant chitosan-degrading enzyme. In some embodiments, the enzyme is not a chitosan-degrading enzyme and the material is free of collagen. In some embodiments, the enzyme is not a biofilm-degrading enzyme.

In some embodiments, the wound dressing, implantable medical device, or cosmetic wipe comprises a fabric or textile coated with one or more layer of the solid chitosan matrix material. In some embodiments, the wound dressing, implantable medical device, or cosmetic wipe comprises fibers of the solid chitosan matrix material. In some embodiments, the fibers of the solid chitosan matrix material are part of a fabric or textile.

In some embodiments, the presently disclosed subject matter provides a method for controlling fluid flow through the chitosan matrix and/or chitosan matrix-coated substrate by controlling the thickness, length, diameter, cross-sectional shape and other structural parameters of the chitosan matrix and/or chitosan matrix-coated substrate. In some embodiments, the presently disclosed subject matter provides a method for controlling fluid flow through the chitosan matrix and/or chitosan matrix-coated substrate by controlling the chemical composition and properties, such as hydrophilicity or hydrophobicity, of the chitosan matrix and/or chitosan matrix-coated substrate. In some embodiments, the presently disclosed subject matter provides a method of controlling the contact time between one or more enzyme-substrate compounds present in the fluid that is in contact with the chitosan matrix and/or chitosan-coated matrix and one or more enzymes entrapped in the chitosan matrix. In some embodiments, the presently disclosed subject matter provides a method for controlling the catalytic efficiency of the system comprising a solid chitosan matrix with one or more active enzymes entrapped (e.g., non-covalently entrapped) therein by controlling the structure, macroscopic morphology, microscopic morphology and/or chemical composition of the substrate.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Chitosan immobilized catalase and carbonic anhydrase
Catalase enzyme was immobilized with chitosan onto a cotton yarn substrate. Catalase rapidly decomposes hydrogen peroxide into molecular oxygen and hydrogen (2 $H_2O_2 \rightarrow O_2 + 2H_2O$), and when the enzyme is exposed to a hydrogen peroxide solution, molecular oxygen bubbles are rapidly generated. After dry storage for greater than two months at room temperature, a biocatalytic textile comprising cotton yarn coated with chitosan with entrapped catalase enzyme was able to degrade hydrogen peroxide when immersed in an aqueous solution containing hydrogen peroxide, as evidenced by clearly visible bubble formation at the surface of the chitosan/catalase coated yarn. An equivalent textile comprising cotton yarn coated with chitosan without catalase did not exhibit bubble formation in this test. The test was repeated several times throughout the storage period. Each time, the same biocatalytic evidence of clearly visible bubble formation occurred for the biocatalytic textile coated with chitosan/catalase. The biocatalytic textile was rinsed in water and dried after each test, then stored dry with no special handling until the next test, illustrating the durability of the material and demonstrating the secure entrapment of enzyme in the chitosan polymer matrix.

Although the presently disclosed subject matter is not limited to chitosan-entrapped catalase, the chitosan-catalase materials can be useful in many different applications, including for hydrogen peroxide elimination in process water, such as could be useful for bleach clean-up; and the generation of oxygen in water by decomposition of hydrogen peroxide, such as could be useful for aeration.

Carbonic anhydrase enzyme was entrapped in a chitosan matrix to form a solid film. Carbonic anhydrase rapidly catalyzes the reaction of carbon dioxide with water to produce biocarbonate anion and a proton ($CO_2$+$H_2O \rightarrow HCO_3^- + H^+$), and when the enzyme is exposed to a solution comprising dissolved carbon dioxide, the pH of the solution decreases due to the production of protons. The pH of the solution can be monitored by adding a colorimetric pH indicator to the solution. The rate at which the pH of the solution decreases is faster in the presence of carbonic anhydrase compared to an equivalent test without carbonic anhydrase. A first chitosan solution was prepared by dissolving solid chitosan flakes in 2 v/v % acetic acid with mixing at room temperature to form a 4 wt/v % chitosan solution. The resulting solution was poured into a polytetrafluoroethylene (PTFE) tray and dried at room temperature for about 24 hours under a ventilated hood. The solid film was cut into pieces and dissolved in 100 mM sodium acetate buffer, pH 5, and stirred at room temperature for about 3 hours to produce an approximate 3.5 wt/v % chitosan solution. Carbonic anhydrase from bovine erythrocytes (lyophilized powder, Product No. C3934, Sigma-Aldrich, St. Louis, Mo., United States of America) was dissolved in 100 mM sodium acetate buffer, pH 5, and combined with a portion of the 3.5 wt/v % chitosan solution to produce a chitosan/enzyme solution with a mass ratio of chitosan to enzyme of 14:1. The chitosan/enzyme solution was spread on a glass plate to form a thin film and dried at room temperature for about 24 hours under a ventilated hood. After the chitosan/enzyme film was prepared, the dry film was stored in a sealed container at room temperature for at least one week prior to testing. When exposed to a solution comprising carbon dioxide, the biocatalytic film comprising chitosan with entrapped carbonic anhydrase enzyme produced a faster decrease in the pH of the solution that was in contact with the film compared to the rate of pH decrease observed when the carbon dioxide solution was placed in contact with an equivalent amount of film comprising chitosan without carbonic anhydrase. The rate of pH decrease was monitored by observing the time for a pH indicator (Bromothymol Blue) added to the test solution to change color from blue to yellow in the vicinity of where the test solution was in contact with the film. Bromothymol Blue indicator changes color from blue to yellow as the pH of the solution decreases in the range from above or around pH 7.6 to around or below pH 6. The biocatalytic film comprising chitosan with entrapped carbonic anhydrase enzyme produced a faster color change from blue to yellow in a solution comprising dissolved $CO_2$ compared to the rate of color change observed for an equivalent chitosan film without carbonic anhydrase.

Although the presently disclosed subject matter is not limited to chitosan-entrapped carbonic anhydrase, the chitosan/carbonic anhydrase materials can be useful in many different applications, including for selectively removing carbon dioxide from an industrial gas mixture (e.g. during fertilizer production), selectively removing carbon dioxide from a combustion gas mixture (e.g. exhaust gas from coal or natural gas burning power plants), selectively removing carbon dioxide from blood (e.g. during blood dialysis, for use in an artificial lung), selectively removing carbon dioxide from air in an enclosed environment (e.g. a rebreather, an air conditioner, a submarine, a spacecraft, etc.), or selectively removing carbon dioxide for the purpose of upgrading biogas.

Example 2

Preparation of Mild pH Chitosan Solution B

Solid chitosan flakes were dissolved with mixing in 2% (v/v) aqueous acetic acid solution (pH 2.5) to make a homogeneous 4% (w/w) "chitosan solution A." Chitosan solution A was poured onto a polytetrafluoroethylene (PTFE) tray and air dried in a fume hood (1st evaporation) at ambient temperature for 24 hours. The air drying allowed excess acetic acid to evaporate, leaving behind a solid "chitosan film A." Chitosan film A obtained in this way was dissolved in sodium acetate buffer (100 mM, pH 5) to obtain 3.5% (w/w) "chitosan solution B."

Example 3

Preparation of Chitosan Film B

A portion (6 mL) of chitosan solution B, prepared according to Example 2, was poured onto a PTFE tray and air dried in a fume hood (2nd evaporation) at ambient temperature for at least 12 hours to obtain "chitosan film B."

Example 4

Preparation of Chitosan-bCAT Solution

A weighed amount (11 mg) of lyophilized catalase from bovine liver, bCAT (catalog no. 9001-05-02, Sigma-Aldrich), was mixed with chitosan solution B (10 g) and 500 μL sodium acetate buffer (100 mM, pH 5.0±0.1) to give a concentration of 24 mg bCAT per gram of chitosan polymer. This chitosan-bCAT solution was mixed for up to 30 minutes at ambient temperature before use.

Example 5

Preparation of Chitosan-bCAT Film

A portion (6 mL) of chitosan-bCAT solution was poured onto a PTFE tray and air dried in a fume hood (2nd evaporation) at ambient temperature for at least 12 hours to obtain "Chitosan-bCAT film."

Example 6

Preparation of Coagulated-Chitosan Films Using Aqueous Potassium Carbonate

Portions (0.4 mL) of chitosan solution B (from Example 2) were spread on glass slides. The slides were immersed in an aqueous 2.1 M potassium carbonate ($K_2CO_3$) coagulation bath for different periods of time (20, 40, 60 and 120 s), after which the slides were removed from the $K_2CO_3$ coagulation bath and washed in three sequential beakers containing deionized water to produce "Chitosan film PC." The water in the washing baths was changed as needed to ensure a neutral pH in the last two wash baths, which was checked using pH paper. This same procedure was repeated using portions of chitosan-bCAT solution (from Example 4) to produce "Chitosan-bCAT film PC."

Example 7

Preparation of Coagulated-Chitosan Fibers Using Aqueous Potassium Carbonate

A portion of chitosan solution B (from Example 2) was filled into a 10 mL syringe equipped with a 23 gauge needle.

The solution was injected into an aqueous 2.1 M potassium carbonate ($K_2CO_3$), pH 12, coagulation bath with the tip of the needle submerged in the bath. A fiber formed immediately when the chitosan solution encountered the coagulation bath. Coagulated fiber (Chitosan fiber PC) was removed from the coagulation bath and washed in three sequential beakers containing deionized water before air drying or further testing. The water in the washing baths was changed as needed to ensure a neutral pH in the last two wash baths, which was checked using pH paper. This same procedure was repeated using portions of chitosan-bCAT solution (from Example 4) to produce "chitosan-bCAT fiber PC."

Example 8

Preparation of Coagulated-Chitosan Fibers Using Aqueous Potassium Hydroxide

A portion of chitosan solution B (from Example 2) was filled into a 10 mL syringe equipped with a 23 gauge needle. The solution was injected into an aqueous 2 M potassium hydroxide (KOH), pH 14, coagulation bath with the tip of the needle submerged in the bath. A fiber formed immediately when the chitosan solution encountered the coagulation bath. Coagulated fiber (Chitosan fiber PH) was removed from the coagulation bath and washed in three sequential beakers containing deionized water before air drying or further testing. The water in the washing baths was changed as needed to ensure a neutral pH in the last two wash baths, which was checked using pH paper. This same procedure was repeated using portions of chitosan-bCAT solution (from Example 4) to produce "Chitosan-bCAT fiber PH."

Example 9

Peroxide Substrate

Aqueous solutions of 5 M and 40 mM $H_2O_2$ were prepared as substrates to test for catalase enzyme activity.

Example 10

Test for Presence of Hydrogen Peroxide by Test Strip

EMD MILLIPORE™ MQUANT™ Peroxide Test Strips (Fisher Scientific, Hampton, N.H., United States of America) with a detection range of (0.5 to 25 mg/L $H_2O_2$) were used according to the package instructions. Upon immersing the test strip into the test liquid, a dark blue color of the test strip corresponds to a high concentration of hydrogen peroxide (>25 mg/L), while a white color of the test strip (no color change) corresponds to a hydrogen peroxide concentration below the test strip detection limit (<0.5 mg/L). Varying shades of pale blue color correspond to a hydrogen peroxide concentration in the range between 0.5 to 25 mg/L.

Example 11

Test for Presence of Hydrogen Peroxide by Bubble Formation

The enzyme catalase catalyzes the degradation of hydrogen peroxide into molecular oxygen ($O_2$) gas and water. The reaction happens rapidly and causes the evolution of oxygen gas bubbles from the vicinity of the catalase enzyme. When catalase enzyme is dissolved in an aqueous liquid to which $H_2O_2$ is added, rapid bubble formation can be observed throughout the liquid, indicating that catalase is present throughout the liquid. When catalase is immobilized in or on a solid material that is immersed in an aqueous liquid and $H_2O_2$ is added to the liquid, evolution of gas bubbles from the vicinity of the solid immobilized catalase is a positive test for the presence of active catalase in or on that material. The test is validated by conducting the same test on a piece of the solid material, but without catalase in or on the material. If no gas bubbles form, it is determined that the material itself does not cause gas bubble formation, and the gas bubble formation observed in the presence of catalase is attributed to catalase catalytic activity.

Example 12

Test of Samples for Catalase Activity by Bubble Formation

Samples prepared in the above examples were tested for catalase activity according to the method described in Example 11. Results are shown in Table 1, below. Chitosan films and fibers prepared without bCAT showed no bubble formation (marked by an "X" in the table). Chitosan samples containing bCAT prepared as described in Examples 5, 6, and 7 all showed bubble formation (marked by a "✓" in the table), indicating the presence of active catalase in these materials.

TABLE 1

Observation of oxygen bubbles formation after immersing samples into $H_2O_2$ solutions.

|  | 5M $H_2O_2$ | 40 mM $H_2O_2$ |
| --- | --- | --- |
| Chitosan film B | X | X |
| Chitosan film PC | X | X |
| Chitosan fiber PH | X | X |
| Chitosan fiber PC | X | X |
| Chitosan-bCAT film | ✓ | ✓ |
| Chitosan-bCAT film PC | Not tested | ✓ |
| Chitosan-bCAT fiber PH | X | X |
| Chitosan-bCAT fiber PC | ✓ | ✓ |

Example 13

Test of Samples for Catalase Activity by Peroxide Test Strip

The peroxide test strip showed a dark blue color when dipping it in 40 mM $H_2O_2$ solution. A 1.5 cm×2 cm Chitosan-bCAT film from Example 5 was immersed in 7.2 mL of the 40 mM $H_2O_2$ solution. A peroxide strip test was performed on the solution after 30 minutes and the test strip showed a white color, indicating $H_2O_2$ was decomposed in the presence of Chitosan-bCAT film. The test was repeated twice by moving the same chitosan-bCAT film to a beaker with 7.2 mL of fresh $H_2O_2$ solution. The strip test was carried out after drying the tested Chitosan-bCAT film sample overnight, then immersing it in fresh $H_2O_2$ solution, as before. Results are shown in Table 2, below. For some samples, a larger volume (20 mL) of 40 mM $H_2O_2$ solutions was used in order to immerse all "Chitosan-bCAT film PC" sample on the slides into the liquid. Results show that all tested samples of Chitosan-bCAT film decreased the concentration of peroxide initially present in the solution, indicating the Chitosan-bCAT film was biocatalytically active and retained activity after drying and retesting.

TABLE 2

Peroxide strip tests of samples.

| | 7.2 mL 40 mM H$_2$O$_2$ | | 20 mL 40 mM H$_2$O$_2$ |
|---|---|---|---|
| | 30 min | | 1 hour |
| Chitosan-bCAT film | White | White | White |
| Chitosan-bCAT film PC | Not tested | Not tested | White |
| Re-dried Chitosan-bCAT film | White | White | White |
| Re-dried Chitosan-bCAT film PC | Not tested | Not tested | White |
| Chitosan-bCAT fiber PC* | Not tested | Light blue | Not tested |

*A single "chitosan-bCAT fiber PC" with 15 cm length was used in the test.

Example 14

Flexible Biocatalytic Coating—Preparation of Mild pH Chitosan Solution

Solid chitosan flakes (2.4 g) were dissolved with mixing in 60 mL 2% (v/v) aqueous acetic acid solution (pH 2.7) to make a homogeneous 4% (w/w) "chitosan solution A."

Example 15

Flexible Biocatalytic Coating—Preparation of Chitosan-TU-CAT Solution

A weighed amount (50 g) of chitosan solution A was mixed with 10 g of 100 mM sodium acetate buffer (pH 5) to obtain a "diluted chitosan solution A." Then, 20 mL of Terminox Ultra 50 L catalase, TU-CAT (Novozymes A/S, Bagsvrd, Denmark), was mixed with diluted chitosan solution A to give a concentration of 75 mg TU-CAT per gram of chitosan polymer, based on solids content of TU-CAT. This "chitosan-TU-CAT solution" was mixed for 30 minutes at ambient temperature to form a homogeneous solution before use.

Example 16

Flexible Biocatalytic Coating—Preparation of Cotton Yarn Dip-Coated with Chitosan-TU-CAT Solution An amount (2.8 meters) of 100% worsted cotton yarn was packed into a rectangular PTFE tray (13 cm×13 cm×0.5 cm) by laying a segment of yarn along one side of the tray, bending the yarn to lay a next segment alongside the initial segment but in the opposite direction, and repeating this back-and-forth laying of the yarn until the tray was full of yarn (3 layers deep). A sufficient amount (about 40 g) of chitosan-TU-CAT solution was poured into the PTFE tray packed with cotton yarn to completely submerge the yarn. After soaking in the chitosan-TU-CAT solution for 3 hours, the yarn was removed from the solution, draped across hangers and air-dried overnight at ambient conditions to obtain "chitosan-TU-CAT yarn."

Example 17

Flexible Biocatalytic Coating—Preparation of Cotton Yarn Dip-Coated with Chitosan Solution The same procedure as described in Example 15 was followed, except adding 20 mL sodium acetate instead of 20 mL TU-CAT solution into diluted chitosan solution A (from Example 15) to form "chitosan solution C," which was used to soak the 100% cotton yarn as described in Example 16 and produce "chitosan yarn."

Example 18

Flexible Biocatalytic Coating—Preparation of Multifiber Fabric Strips Dip-Coated with Chitosan-TU-CAT Solution Style #50 Multifiber fabric (Testfabrics Inc., West Pittston, Pa., United States of America) is made of yarns woven in different strips of boiled off cotton, bleached cotton, mercerized cotton, unbleached linen, bleached linen, spun silk, spun viscose and worsted wool. Each different woven strip has a width of approximately 1.2 cm. Multifiber fabric, cut to a size of 5 cm wide by 10 cm long, was coated with chitosan-TU-CAT as described in Example 16, except the time of submerging samples in the solution was 2 hours, and the samples were flipped over after 1 hour immersion. The coated multifiber fabric is called "chitosan-TU-CAT multifiber fabric."

Example 19

Flexible Biocatalytic Coating—Preparation of Multifiber Fabric Strips Dip-Coated with Chitosan Solution The same procedure as described in Example 18 was followed, except adding 20 mL sodium acetate instead of 20 mL TU-CAT solution into diluted chitosan solution A (from Example 15) to form "chitosan solution C," which was used to soak the multifiber fabric and produce "chitosan multifiber fabric."

Example 20

Flexible Biocatalytic Coating—Preparation of Chitosan-TU-CAT Fabric Using Coated Yarn A swatch of fabric with dimensions of approximately 7 cm×10 cm and weighing 3.72 grams was prepared by hand weaving chitosan-TU-CAT yarn together with untreated 100% spun cotton yarn in a plain weave pattern. A plain weave fabric has a regular over-and-under repeating pattern for each yarn segment. The chitosan-TU-CAT yarns were used for all the yarn segments in one direction of the plain weave and the 100% cotton yarn was used for all the yarn segments in the perpendicular direction to obtain "chitosan-TU-CAT fabric."

Example 21

Home Laundry Washing Procedure

The durability of the chitosan-TU-CAT coating was tested by subjecting test samples to one or more washes in a front-loading home laundry washing machine. Samples subjected to this test were placed in a nylon foot stocking with the open end tied closed. The nylon stocking with sample inside was placed in a lingerie washing bag made of netted fabric. The lingerie bag was placed in the washing machine with an average size load of household laundry. The recommended amount of laundry detergent (Tide Purclean, Procter & Gamble, Cincinnati, Ohio, United States of America) for the load size was added to the washing machine detergent dispenser. For Delicate Cycle, the machine settings were set to Delicate Cycle, normal soil level, warm wash/cold rinse and medium spin speed. For Normal Cycle, the machine settings were set to Normal Cycle, normal soil level, warm wash/cold rinse and high spin speed. The relevant washing cycle was run. After the run was complete, the lingerie bag was removed from the machine, and the sample was removed from the nylon stocking inside. A portion of the damp washed sample was cut off for testing. The remaining sample was returned to the nylon stocking and lingerie bag for the next washing cycle. Samples were not dried between washing cycles.

Example 22

Lab Washing Procedure for Multifiber Fabrics

The durability of the chitosan-TU-CAT coating was tested by subjecting multifiber strip test samples to up to three hand washes in the laboratory with tap water and with or without liquid dish washing detergent (Dawn Ultra, Procter & Gamble, Cincinnati, Ohio, United States of America), also called "soap water." In the first wash, the samples were gently washed in running tap water for about 3 minutes without soap. In the second wash, the samples were submerged and squeezed in soap water by hand about 5 minutes, followed by rinsing the samples in running tap water for 3 minutes. In the last wash procedure, a more aggressive hand wash was performed using a higher concentration soap water for 10 minutes, followed by rinsing the samples in running tap water for 3 minutes. Some yarns fell off from the fabric strip after the third wash because the fabric strip edges were raw cut edges. Securing the edges can prevent yarns from falling off.

Example 23

Peroxide Substrate

Aqueous solutions of 0.3% and 40 mM $H_2O_2$ were prepared as enzyme substrate solutions to test for catalase enzyme activity.

Example 24

Test of samples for catalase activity by bubble formation Samples prepared in the examples were tested for catalase activity according to the method described in Example 11. Results are shown in Table 3 and Table 4, below. Some samples were tested as prepared, while some samples were rinsed or washed prior to testing, as indicated in the column labeled "sample description" (Table 3) or the row with "washes" (Table 4). Some samples were pristine controls or chitosan coated yarns and fabrics prepared without TU-CAT. These showed no bubble formation or a very small amount of bubble formation that did not continue forming after shaking the bubbles off (marked by an "X" in the table). Chitosan solution added dropwise to the peroxide solution did not cause bubbles to form. Chitosan coated samples containing TU-CAT prepared as described in Examples 16, 18, and 20 all showed bubble formation emerging from the yarn or fabric (marked by a "✓" in the table), indicating the presence of active catalase in these materials.

The 15 cm chitosan-TU-CAT coated yarn generated a large quantity of oxygen bubbles at the yarn surface, which is attributed to the biocatalytic activity of the yarn due to the presence of catalase in the chitosan coating. Bubbles released from the yarn surface either collected on the submerged surface of the beaker or migrated to the liquid surface where the bubbles popped at the liquid-air interface. Lifting the yarn out of the liquid and into ambient air caused the bubbles accumulated at the surface to pop. More bubbles formed at the yarn surface when the yarn was immersed again in the liquid containing hydrogen peroxide. The yarn coated only with chitosan ("chitosan yarn") showed negligible bubble formation in the solution. The bubbles observed can be due to simple trapping of air, because the bubbles did not form again when the soaked yarn was removed to air and then replaced in the liquid.

As shown by the results in Table 3, the chitosan-TU-CAT coating on cotton yarn continued to exhibit catalase activity by bubble formation after each of three cycles of home laundry, indicating the biocatalytic coating was durable to washing in the presence of typical laundry detergent ingredients and washing conditions. Also, as shown by the results in Table 3, bubble formation was not observed when the samples were placed in water in the absence of hydrogen peroxide, confirming that $H_2O_2$ is needed for oxygen bubble evolution in the presence of catalase.

TABLE 3

Observation of bubble formation after immersing samples into water or $H_2O_2$ solutions.

| Sample Description | Water | 0.3% aq. $H_2O_2$ | 40 mM $H_2O_2$ |
| --- | --- | --- | --- |
| 100% Cotton yarn | X | X | X |
| Chitosan yarn | X | Not tested | X |
| Chitosan-TU-CAT yarn | X | ✓ | ✓ |
| Chitosan-TU-CAT fabric | X | ✓ | ✓ |
| Chitosan-TU-CAT yarn after one Delicate Cycle home laundry wash (Wash 1) | X | ✓ | Not tested |
| Chitosan-TU-CAT yarn after one Delicate Cycle and one Normal Cycle home laundry washes (Wash 2) | X | ✓ | Not tested |
| Chitosan-TU-CAT yarn after one Delicate Cycle and two Normal Cycle home laundry washes (Wash 3) | X | ✓ | Not tested |

The Chitosan-TU-CAT fabric did not generate bubbles when placed in water, without hydrogen peroxide. When the Chitosan-TU-CAT fabric was placed in 0.3% aqueous $H_2O_2$, bubbles emanated from one set of parallel yarns in the plain weave structure (the chitosan-TU-CAT yarn) and did not emanate from the perpendicular set of yarns (the uncoated 100% cotton yarns) in the plain weave fabric structure. This behavior was also observed after the fabric was rinsed in water, air dried, and subsequently soaked in 40 mM $H_2O_2$. Bubbles only emanated from the chitosan-TU-CAT coated yarns when the fabric was exposed to hydrogen peroxide. This result indicates that mixtures, blends or other combinations of coated and non-coated materials can be produced, and illustrates that the presence of biocatalyst can be limited to specific locations in a material by using coating application and fabric construction techniques known in the art.

Chitosan solution C or chitosan-TU-CAT solution B was applied to the multifiber fabric strips without causing significant changes in the appearance of the fabric strips. No bubbles were observed when immersing multifiber fabric strips and chitosan coated fabric strips from Example 19 into 40 mM $H_2O_2$ solution, indicating that neither the multifiber fabric alone nor the chitosan-coated multifiber fabric showed catalytic function in decomposing peroxide. However, bubbles were observed immediately (within 10 seconds) on the fabric surface after immersing the dry chitosan-TU-CAT multifiber fabric into 25 mL of 40 mM $H_2O_2$ solution, indicating the presence of catalase in the coating provided catalytic functionality to the material.

To test the catalytic activity and durability of chitosan-TU-CAT coatings on specific different fibers, the chitosan-TU-CAT coated multifiber fabric strip was partially disassembled by cutting the multifiber fabric into 5 cm×1.2 cm strips of each different fiber type. The test described in Example 11 was performed in separate beakers using 10 mL of 40 mM $H_2O_2$ solution together with unwashed samples and samples washed using procedures described in Example 22. Tests results with unwashed and washed samples are listed in Table 4 with fiber name in the first column. All samples showed bubble formation (marked by a "✓" in the table), indicating the presence of active catalase in these materials. Bubble formation was observed on each strip after one wash and after three washes immediately (<10 second) after being placed in the enzyme substrate solution. Gas bubbles continued to form after previously formed gas bubbles were shaken off. Gas bubbles continued to form at the fabric and loosened yarn surfaces rather than in the bulk liquid surrounding the sample, indicating the biocatalyst binds tightly to the yarn and resists being washed away. This was also observed with intact chitosan-TU-CAT coated multifiber fabrics.

TABLE 4

Observation of bubble formation on different yarns from a multifiber fabric after immersing individual strips of the chitosan-TU-CAT coated yarns in 40 mM $H_2O_2$ solutions.

| Sample Description | No wash | One wash | Two washes | Three washes |
|---|---|---|---|---|
| Spun viscose | ✓ | ✓ | ✓ | ✓ |
| Boiled off cotton | ✓ | ✓ | ✓ | ✓ |
| Bleach cotton | ✓ | ✓ | ✓ | ✓ |
| Mercerized cotton | ✓ | ✓ | ✓ | ✓ |
| Unbleached linen | ✓ | ✓ | ✓ | ✓ |
| Bleach linen | ✓ | ✓ | ✓ | ✓ |
| Spun silk | ✓ | ✓ | ✓ | ✓ |
| Worsted wool | ✓ | ✓ | ✓ | ✓ |

Example 25

Test of Chitosan-TU-CAT Fabric for Catalase Activity by Peroxide Test Strip

The performance of the chitosan-TU-CAT fabric in decomposing hydrogen peroxide was tested under conditions of limited agitation and under conditions of constant agitation. The limited agitation test was conducted first (Example 25a), followed by the constant agitation test (Example 25b). As indicated by a comparison of the results of Example 25a and 25b agitation of the materials and/or liquids in the test system lead to more rapid decomposition of $H_2O_2$. The chitosan-TU-CAT fabric was capable and durable in performing both procedures. Because the constant agitation observation was made after the fabric had already been washed and dried in prior treatment steps, the results also indicate the chitosan-TU-CAT coating is durable to multiple steps of handling and washing.

Example 25a: Fabric Soaking in Aqueous Peroxide with Occasional Agitation

The Chitosan-TU-CAT fabric, made in Example 18 and tested for bubble formation, according to Example 11, when exposed to 0.3% aqueous $H_2O_2$ (made in Example 23), was thoroughly soaked and rinsed in three changes of clean filtered water (200 mL each change), squeezed of excess water and air dried for 12 hours. The dry fabric was placed in 200 mL deionized water and soaked for about 5 minutes. No bubble formation was observed. The fabric was removed from the water, squeezed of excess water, and placed in 150 mL of 40 mM $H_2O_2$ solution. Bubble formation emanating from the fabric was observed. After 90 minutes soaking with occasional hand-stirring, the test solution showed a peroxide level of 2 mg/L $H_2O_2$ using a peroxide test strip, tested and visually compared to the color scale on the package according to the test strip package instructions, according to Example 10. Peroxide test strips immersed in the initial 40 mM $H_2O_2$ solution showed a dark blue color, indicating the presence of >25 mg/L $H_2O_2$. After 160 minutes of total soaking time with occasional hand-stirring, a peroxide test strip immersed in the solution was white, indicating that peroxide was decomposed to a level that is reported as <0.5 mg/L $H_2O_2$. Once the hydrogen peroxide concentration in the liquid was <0.5 mg/L, as indicated by the peroxide test strip, bubble formation at the fabric surface was no longer observed. Thus, bubble formation can be used as an indicator that $H_2O_2$ substrate is diminished or absent. Further, the Chitosan-TU-CAT fabric was effective at completely decomposing hydrogen peroxide in the solution from a concentration of >25 mg/L to <0.5 mg/L. The fabric was thoroughly rinsed in three changes of 200 mL fresh deionized water and air dried for 15 hours.

Example 25b: Fabric Soaking in Aqueous Peroxide with Continuous Mixing

The Chitosan-TU-CAT fabric from the final air drying step was securely affixed around the bottom of the propeller of an overhead mixer. The fabric and propeller were submerged in 150 mL of 40 µM aqueous $H_2O_2$. The mixer was set to a rotation speed of 150 rpm. A peroxide test strip immersed in the stirring liquid after 10 minutes mixing was a medium blue color, indicating a peroxide concentration between 5-10 mg/L $H_2O_2$. A peroxide test strip immersed in the stirring liquid after 20 minutes mixing was white, indicating complete decomposition of peroxide to a <0.5 mg/L level.

Example 26

Wicking and flow tests of peroxide decomposition A wicking test was used to assess the capability of the yarn to decompose $H_2O_2$ while a liquid containing $H_2O_2$ flows through the yarn, assisted by moisture wicking and gravity. A schematic of the wicking test is shown in FIG. 1. Originating container (1) holds test liquid (e.g., solution comprising $H_2O_2$) (2) and one end of coated yarn (3) which conveys liquid by a combination of wicking and gravity-assisted flow in an overall downward direction (4) to a receiving container (5), positioned below the originating container (1), where the transported liquid (6) is collected. The flow of liquid through the yarn is assisted by gravity. The bottom of originating container (1) was positioned at a height of approximately 8 cm above the bottom of receiving container (5). The height from the bottom to the top of each container was 6 cm.

A flow test was used to assess the capability of the yarn to decompose $H_2O_2$ as a result of a liquid containing $H_2O_2$ flowing through the yarn. A schematic of the flow test is shown in FIG. 2. Originating container (1) holds test liquid (2). One end (7) of yarn (3) is held above receiving container (5). Test liquid (2) is contacted with the top end (8) of end (7) of yarn (3), and the liquid flows through the yarn in an overall downward direction (4) which conveys the liquid by gravity-assisted flow to a receiving container (5), positioned below top end (8) of end (7), where the transported liquid (6) is collected. The flow of liquid through the yarn is assisted by gravity.

Example 26a: Wicking Tests with Cotton Yarn, Chitosan Coated Yarn and Chitosan-TU-CAT Yarn Yarn with a length of 30 cm was used in the wicking test with 5 mL of 40 mM aqueous $H_2O_2$ in the upper beaker (originating container (1) according to FIG. 1). The solutions in both upper and lower beakers (receiving container (5) according to FIG. 1) were tested by the peroxide test strip (Example 10) after 50 minutes and after 2 hours. All 5 mL of the original test liquid (2) in the upper container (1) were absorbed by the yarn and transferred to the lower container (5) within 2 hours by wicking through the yarn. Greater than 25 mg/L $H_2O_2$ was detected (dark blue test strips) in the lower containers for cotton yarn and chitosan coated cotton yarn after 50 minutes and after 2 hours, indicating that $H_2O_2$ was not significantly decomposed by wicking though these yarns. The results also show that the concentration of the original $H_2O_2$ liquid in the top beakers remained >25 mg/L $H_2O_2$ during the test, indicating that the original liquid was stable during the test, and required the presence of biocatalyst to decompose. However, no peroxide (<0.5 mg/L $H_2O_2$) was detected (white test strips) in the lower containers for chitosan-TU-CAT coated cotton yarn after 50 minutes and after 2 hours, indicating the biocatalytic effectiveness of chitosan-TU-CAT in decomposing $H_2O_2$ as the $H_2O_2$-containing liquid passed through the chitosan-TU-CAT coated yarn.

Example 26b Flow Tests with Cotton Yarn, Chitosan Coated Yarn and Chitosan-TU-CAT Yarn Each flow test used 60 drops of 40 mM aqueous $H_2O_2$ applied to the top of the yarn at a rate of 1 drop per second. The flow test for a yarn sample was conducted followed the wicking test (Example 26a) without drying or rinsing the yarn. The peroxide levels (Example 10) of liquids collected from cotton yarn and chitosan yarn were >25 mg/mL (dark blue), indicating that $H_2O_2$ was not significantly decomposed by flowing though these yarns. The peroxide level of liquid collected from chitosan-TU-CAT yarn was about 0.5 mg/mL, indicating the biocatalytic effectiveness of chitosan-TU-CAT in decomposing $H_2O_2$ as the $H_2O_2$-containing liquid flowed through the chitosan-TU-CAT coated yarn.

Results of wicking and flow test results for unwashed cotton yarn, chitosan coated yarn and chitosan-TU-CAT coated yarn are shown in Table 5, below.

TABLE 5

Peroxide test strip results from wicking and flow tests on unwashed and initially dry cotton yarn, chitosan yarn and chitosan-TU-CAT yarn.

| Sample | Wicking test results | Flow test results |
| --- | --- | --- |
| Non-coated 100% cotton yarn | With reference to FIG. 1, after 50 minutes, the peroxide level of original 40 mM $H_2O_2$ liquid (2) was >25 mg/L and of liquid (6) was >25 mg/L, indicating that the cotton yarn was not effective in lowering the concentration of $H_2O_2$ in original liquid (2) or collected/transported liquid (6). After 2 hours, all liquid from container (1) was absorbed and transferred to container (5), and the peroxide level of liquid (6) was >25 mg/mL. | With reference to FIG. 2, after applying 60 drops of fresh 40 mM $H_2O_2$ to the top end (8) of the yarn, the peroxide level of liquid (6) was >25 mg/L, indicating that cotton yarn (3) was not effective in lowering the concentration of $H_2O_2$ in the applied test liquid. |
| Chitosan yarn | With reference to FIG. 1, after 50 minutes, the peroxide level of liquid (2) was >25 mg/L and of liquid (6) was >25 mg/L, indicating that the chitosan coated yarn was not effective in lowering the concentration of $H_2O_2$ in original liquid (2) or collected liquid (6). After 2 hours, all liquid from container (1) was absorbed and transferred to container (5), and the peroxide level of liquid (6) was >25 mg/mL. | With reference to FIG. 2, after applying 60 drops of fresh 40 mM $H_2O_2$ to the top end (8) of the yarn, the peroxide level of liquid (6) was >25 mg/L, indicating that chitosan coated cotton yarn (3) was not effective in lowering the concentration of $H_2O_2$ in the applied test liquid. |
| Chitosan-TU-CAT yarn | With reference to FIG. 1, after 50 minutes, the peroxide level of liquid (2) was >25 mg/L, and of liquid (6) was <0.5 mg/L, indicating that the chitosan-TU-CAT coated yarn was effective | With reference to FIG. 2, after applying 60 drops of fresh 40 mM $H_2O_2$ to the top end (8) of the yarn, the peroxide level of liquid (6) was 0.5 mg/L, indicating |

TABLE 5-continued

Peroxide test strip results from wicking and flow tests on unwashed and initially dry cotton yarn, chitosan yarn and chitosan-TU-CAT yarn.

| Sample | Wicking test results | Flow test results |
|---|---|---|
|  | in lowering the concentration of $H_2O_2$ in collected liquid (6). After 2 hours, all liquid from container (1) was absorbed and transferred to container (5), and the peroxide level of liquid (6) was <0.5 mg/mL. | that chitosan-TU-CAT coated cotton yarn (3) was effective in lowering the concentration of $H_2O_2$ in the applied test liquid. |

Example 26c: Wicking and Flow Tests with Chitosan-TU-CAT Coated Yarn after Washes Wicking and flow tests were conducted with chitosan-TU-CAT yarn samples washed in Example 21. With reference to FIGS. 1 and 2 and to the sample names used in Table 6, below, Wash 1, Wash 2 and Wash 3 samples of yarn (approx. 30 cm from each wash cycle) were tested for their ability to degrade $H_2O_2$ (Example 10). For the wicking test, a segment (approx. 5-8 cm) of each yarn was immersed in 0.3% aqueous $H_2O_2$ test liquid (2). For each yarn sample, bubble formation emanating from the immersed yarn segment was observed (Example 11), indicating that at least a portion of the chitosan-TU-CAT coating remained biocatalytically active and remained attached to the cotton yarn after up to three home laundry wash cycles. Additional descriptions of each yarn wicking test are shown in Table 6, along with the test results. After 1 hour of wicking for Wash 1, the liquid in the top container had an $H_2O_2$ concentration of 2-5 mg/L (light blue test strip) and the liquid in the bottom container had an $H_2O_2$ concentration of <0.5 mg/L (white test strip).

In the flow test, the test liquid (2, in FIG. 2) was applied dropwise to the top end (8) of the yarn (3) at a rate of 1-3 seconds per drop, and the top of the yarn was held approximately 15-30 cm above the bottom of receiving container (5). Additional descriptions of each yarn flow test and results are shown in Table 6. A Wash 2 sample after the flow test provided liquid in the bottom container that had an $H_2O_2$ concentration of <0.5 mg/L (white test strip).

TABLE 6

Peroxide test strip results from wicking and flow tests on home laundry washed chitosan-TU-CAT yarns.

| Sample | Additional Test Description | Results |
|---|---|---|
| Chitosan-TU-CAT yarn (Wash 1) | Wicking test using 5 mL of 0.3% aq. $H_2O_2$ as the test liquid (2) | With reference to FIG. 1, within 1 hour, the peroxide level of liquid (2) was 2-5 mg/L and of liquid (6) was <0.5 mg/L, indicating that the top end (8) of yarn (3) was effective in lowering the concentration of $H_2O_2$ in liquid (2) compared to the original concentration (>25 mg/L $H_2O_2$) and indicating that $H_2O_2$ was completely decomposed by the time the final liquid (6) reached receiving container (5). |
| Chitosan-TU-CAT yarn (Wash 2) | Wicking test using 10 mL of 0.3% aq. $H_2O_2$ as the test liquid (2); and, flow test using the 5 mL aliquot of test liquid (2) remaining in container (1) after the wicking test. | With reference to FIG. 1, movement of the initial liquid front for wicking along the yarn (3) from originating container (1) to receiving container (5) required approximately 1 hour. Note that the initial amount of 0.3% $H_2O_2$ used in this test was twice the amount used in the Wash 1 test. After this initial 1 hour of the wicking test, the $H_2O_2$ concentration of the liquid (2) in container (1) was >25 mg/L and the final liquid (6) in receiving container (5) had a $H_2O_2$ concentration of <0.5 mg/L. Bubbles were observed emanating from the yarn segment immersed in liquid (2), however a detectable change in $H_2O_2$ concentration was not immediately measurable. Nevertheless, liquid transported through the yarn by wicking was completely decomposed by the time the final liquid (6) reached receiving container (5). The wicking test was allowed to continue for 3.5 hours, after which time the concentration of $H_2O_2$ in the original liquid (2) was 2-5 mg/L, indicating the segment of yarn immersed in the originating liquid continued functioning over time, and was able to lower the concentration of $H_2O_2$ in the liquid. |

TABLE 6-continued

Peroxide test strip results from wicking and flow
tests on home laundry washed chitosan-TU-CAT yarns.

| Sample | Additional Test Description | Results |
|---|---|---|
| | | With reference to FIG. 2, the flow test used approximately 100 drops (5 mL) of liquid (2) remaining in container (1) after the end of the wicking test ($H_2O_2$ concentration of 2-5 mg/L). The remaining liquid (2) from container (1) was applied dropwise to the end (8) of end (7), which was held by tweezers. The pool of liquid (6) at the bottom end of the yarn in receiving container (5) tested negative (<0.5 mg/L) for $H_2O_2$. The results indicate that any remaining $H_2O_2$ in liquid (2) was completely decomposed by flowing through the Chitosan-TU-CAT yarn. |
| Chitosan-TU-CAT yarn (Wash 3) | Wicking test using 5 mL of 0.3% aq. $H_2O_2$ | With reference to FIG. 2, movement of the initial liquid front for wicking along the yarn (3) from container (1) to container (5) required approximately 1.5 hours. Note that the initial amount of 0.3% $H_2O_2$ used in this test was the same as the amount used for the Wash 1 test. After the 1.5 hours elapsed, the $H_2O_2$ concentration of the liquid (2) in container (1) was 2-5 mg/L and the final liquid (6) in receiving container (5) had a $H_2O_2$ concentration of <0.5 mg/L. The results indicate that the top end of yarn (3) was effective in lowering the concentration of $H_2O_2$ in liquid (2) compared to the original concentration (>25 mg/L $H_2O_2$) and indicate that $H_2O_2$ was completely decomposed by the time the final liquid (6) reached the receiving container (5). |

Example 26d: $H_2O_2$ Decomposition by Immersion and Flow Tests with a Chitosan-TU-CAT Coated Yarn Chitosan-TU-CAT coated yarns, prepared as described in Example 16, and where the weight ratio of coating solution to cotton yarn was 12:1, were cut to a length of 20 cm. One 20 cm length of chitosan-TU-CAT yarn was immersed in 15 mL of 40 mM aq. $H_2O_2$ at room temperature without agitation. After 15 minutes, the concentration of peroxide in the liquid was 10-25 mg/L according to the medium blue color of the peroxide test strip (Example 10). This test showed that placing a chitosan-TU-CAT coated yarn in an unmixed peroxide solution for a period of time resulted in a decrease in the peroxide concentration of the liquid. Another 20 cm length of chitosan-TU-CAT yarn was used to perform the flow test as illustrated in FIG. 2. An amount (15 mL) of 40 mM aq. $H_2O_2$ was forced to flow through the chitosan-TU-CAT yarn by applying the solution dropwise to the top of the yarn at a rate that applied the entire 15 mL amount to the yarn within a timeframe of 15 minutes. A peroxide test strip immersed in the solution (6) collected from the bottom of the flow test (FIG. 2) remained white, indicating no detectable $H_2O_2$ (<0.5 mg/L peroxide). The results indicate that more efficient peroxide decomposition occurred when the 15 mL of liquid comprising peroxide travelled through the chitosan-TU-CAT yarn compared to when an equivalent yarn was immersed in 15 mL of the peroxide-liquid without stirring.

Example 27

Rotisserie Washing Test for Longevity Evaluation of Entrapped or Absorbed Enzyme Chitosan coated cotton yarn (Chi-Cot), catalase entrapped chitosan coated yarns (Chi-CAT-Cot) and cotton yarns with adsorbed catalase (CAT-Cot) were washed in 10 mL deionized water in sealed tubes mounted in a rotisserie washing apparatus operating with an end-over-end rotation speed of 25 rpm at 37° C. for 2 hours, 24 hours and 25 days. Yarns washed for the indicated time intervals were removed from the washing liquid, air dried, and tested for catalytic activity as described in Example 11 (bubble formation test) and Example 26b (flow test). Results of the flow test (Table 8, below) show that the biocatalytic function of the Chi-CAT-Cot yarn remained after 25 days of washing. Liquid from the washing tubes was collected at the indicated time intervals. The protein concentration in the collected liquids was measured using the BCA assay (PIERCE™ Rapid Gold BCA Protein Assay Kit, Thermo Fisher Scientific, Waltham, Mass., United States of America). The BCA assay results showed that less enzyme protein was washed off the yarn in the presence of the chitosan coating.

The presence of active catalase in the collected liquids was evaluated using a visual "Foaming Test" assessment. In the Foaming Test, an aliquot (5 mL) of liquid collected from each tube of the rotisserie washing test was added to a glass tube. Then, in sequence, to each glass tube were added 100 µL of 1% (v/v) Triton X-100 solution and 5 mL 40 mM $H_2O_2$ solution, the tube was gently tapped five times, and the height of foam formation was measured after one minute. A large amount of foam formation in the Foaming Test indicates the evolution of oxygen gas, which indicates the presence of a high amount of active catalase in the test liquid. A high amount of catalase in the test liquid indicates that catalase washed off the yarn during the rotisserie washing test. The peroxide strip test, as described in Example 10 was performed with Foaming Test solutions that were held at room temperature for 15 minutes. The results of the bubble formation test for the washed and dried yarns and the Foaming Test and the peroxide strip test for the corresponding washing solutions are summarized in Table 7, below. The bubble formation test showed a higher longevity of catalytic activity of the yarn coated with chitosan/enzyme compared to yarn coated with enzyme only. The Foaming Test and peroxide strip test showed that less active enzyme was washed off the yarn in the presence of the chitosan coating. The presence of chitosan also prevented the yarn from fraying during the washing test, preserving the yarn physical structure.

TABLE 7

Results of the bubble formation test for washed yarns, and the Foaming Test and the peroxide strip test for washing solutions from the rotisserie washing test.

| Sample | Bubble formation test on yarns | Foaming Test on washing solutions | Peroxide strip test on Foaming Test solutions |
|---|---|---|---|
| Chi | No bubbles at the yarn surface | No white foam | Dark blue |
| Chi-CAT | For the 25 day washed yarn, a high amount of bubble formation was observed all along the yarn surface (similar level of bubble formation compared to the equivalent unwashed yarn) | No white foam from 2 hrs washed yarns and less than 0.2 cm white foam from 25 day washed yarns; vigorous shaking of 25 day washed yarns formed <0.3 cm white foam | Dark blue |
| CAT | For the 25 day washed yarn, very little bubble formation was observed, and only in some places at the yarn surface (much lower level of bubble formation compared to the equivalent unwashed yarn) | About 1.1 cm height white foam from 2 hrs washed yarns and about 1.5-1.9 cm height white foam formed; vigorous shaking of 25 day washed yarns formed about >3.5 cm height foam | White or very light blue |

TABLE 8

Peroxide test strip results from immersion, wicking and flow tests on rotisserie washed Chi and Chi-CAT yarns with 40 mM aq. $H_2O_2$ (with 2 cm yarns immersed in solution in in upper beakers).

| Sample | Upper beaker | Lower beaker |
|---|---|---|
| Chi (No wash, 2 hours washed, 24 hours washed, 25 days washed) | >25 mg/mL | >25 mg/mL |
| Chitosan- CAT yarn (2 hours rotisserie washed) | >25 mg/mL | <0.5 mg/mL |
| Chitosan- CAT yarn (24 hours rotisserie washed) | >25 mg/mL | <0.5 mg/mL |
| Chitosan- CAT yarn (25 days rotisserie washed) | >25 mg/mL | <0.5 mg/mL |

Example 28

Entrapment of Carbonic Anhydrase in Chitosan Film from a Mild Solution

Carbonic anhydrase from bovine erythrocytes (lyophilized powder, Product No. C3934, Sigma-Aldrich, St. Louis, Mo., United States of America) was dissolved in 100 mM sodium acetate buffer, pH 5, and combined with a portion of the "solution B" in Example 2 to produce a "chitosan-CA solution" with a mass ratio of chitosan to enzyme of 14:1. About 5 mL of the "chitosan-CA solution" was spread on a glass plate to form a thin film and dried at room temperature for about 24 hours under a ventilated hood. After the "chitosan-CA film" was prepared, the dry film was stored in a sealed container at room temperature for at least one week prior to testing.

Example 29

Preparation of a Chitosan Film from a Mild Solution

About 5 mL of the "Solution B" in Example 2 was spread on a glass plate to form a thin film and dried at room temperature for about 24 hours under a ventilated hood. After the "chitosan film" was prepared, the dry film was stored in a sealed container at room temperature for at least one week prior to testing.

Example 30 pH Indicator Test for Entrapped Carbonic Anhydrase Activity

Equal amounts of chitosan-CA film from Example 28 and "chitosan film" from Example 29 were placed in separate plastic petri dishes. An indicator solution comprising 6 mL of Tris buffer (pH 8.3) and 300 μL of 1 g/L bromothymol blue solution was added to each petri dish to submerge the films. $CO_2$ water was prepared by bubbling $CO_2$ gas through 40 mL of deionized water for 15 minutes. Prepared $CO_2$ water (6 mL) was added to each petri dish and the color change was closely observed. Test solution comprising pH indicator that was in direct contact with the "chitosan-CA film" changed color from blue to yellow immediately after adding $CO_2$ water to the petri dish, indicating a rapid pH drop at the surface of the film comprising the enzyme. The surrounding solution remained blue in color for a few seconds, and then slowly changed to a yellow color after 20-40 seconds. When the same test was conducted using the "chitosan film" prepared in Example 29, both the solution directly in contact with the surface of the film and surrounding the film remained blue in color for a few seconds, then slowly changed to a yellow color after 20-40 seconds.

Example 31

Preparation of a Fungal Chitosan-Enzyme Film at Mild Conditions

Fungal chitosan extracted from *Rhizopus oryzae* cell wall was dissolved in 2% (v/v) acetic acid solution to form a uniform, transparent, pale yellow, viscous solution. The solution was air-dried for 24 hours. Sodium acetate solution (100 mM, pH 5.0) was added to form a 4 wt. % fungal chitosan salt solution. About 8 mg catalase from bovine liver (lyophilized powder, 2,000-5,000 units/mg, Sigma-Aldrich, St. Louis, Mo., United States of America) was added to the solution to form a fungal chitosan-catalase solution. A portion of the solution was poured on a PTFE tray and dried at room temperature for about 2 days under a ventilated hood, forming a pale yellow, transparent film. Another portion of the solution was placed on a glass plate and dried overnight under a ventilated hood, forming a pale yellow, transparent film.

Example 32

Test of Fungal Chitosan-Entrapped Catalase Activity

Aqueous solutions of 10 mM $H_2O_2$ were prepared as substrates to test for Catalase Enzyme Activity.

Peroxide solution (10 mM $H_2O_2$) was applied with a pipette to cover the entire surface of the fungal chitosan-catalase film solidified on the glass plate prepared in Example 31 and sufficient peroxide solution was applied to extend beyond the edges of the film onto the uncoated glass surface. After 20-30 seconds, bubbles formed at the surface coated with fungal chitosan-catalase film, whereas no bubble formation was observed on the uncoated glass surface, and no bubble formation was observed in the bulk liquid. Bubble formation is attributed to the generation of oxygen gas when peroxide decomposition is catalyzed by catalase. This test shows that active catalase enzyme is present in the non-animal-derived fungal chitosan-catalase film.

A portion of fungal chitosan-catalase film prepared in the PTFE tray in Example 31 was submerged in 10 mL of 10 mM $H_2O_2$. After about 1 minute, gas bubbles were observed at the surface of the film, and no bubble formation was observed in the surrounding liquid. Bubble formation is attributed to the generation of oxygen gas when peroxide decomposition is catalyzed by catalase. This shows that active catalase enzyme is present in the fungal chitosan-catalase film.

Example 33

Peroxide Decomposition after Extended Storage of Biocatalytic Textile

Yarn segments (20 cm) prepared as described in Example 16 and stored at ambient conditions for more than 12 months were observed to decompose all the peroxide in a 40 mM peroxide solution through the wicking process as described in Example 28. Yarn segments (20 cm) prepared as described in Example 16 and washed for 25 days as described in Example 27, then stored at ambient conditions for more than 12 months, were observed to decompose all the peroxide in a 40 mM peroxide solution through the wicking process as described in Example 26. After use in the wicking test, each of the yarns also decomposed all the peroxide in 20 mL of 10 mM peroxide within 1 hour with gentle mixing. Therefore, the yarns retained catalytic activity after more than one year of storage at ambient conditions.

Example 34

Preparation of Chi-TU-CAT Coated Fabric by Padding and Peroxide Decomposition Tests TU-CAT was combined with a portion of "solution B" (described in Example 2) to produce a "chitosan-TU-CAT solution" with a mass ratio of chitosan to enzyme of 333:1.

About 17 g rayon fabric (Style #266, TestFabric Inc., West Pittston, Pa., United States of America) was padded with chitosan solution (without enzyme) or padded with chitosan-TU-CAT solution to a wet pick up of 84% using a laboratory padder (Werner Mathis AG, Zurich, Switzerland) and then air dried. About 14 g bleached cotton fabric (Style #400, TestFabric Inc., West Pittston, Pa., United States of America) was padded with chitosan solution (without enzyme) or padded with chitosan-TU-CAT solution to a wet pick up of 74% and then air dried.

Dried fabrics were cut into 1 cm×5 cm strips and submerged in 20 mL of 10 mM $H_2O_2$. The extent of peroxide decomposition was tested using peroxide strips, as described in Example 10. Oxygen bubbles were observed on the Cotton-chi-TU-CAT and Rayon-chi-TU-CAT fabrics after immersing the fabrics into 10 mM $H_2O_2$ solution. Bubbles were not observed on Cotton-chi or Rayon-chi fabrics immersed in the peroxide solution. Test results are shown in Table 9, below.

Therefore, preparation of biocatalytic textile fabrics is possible using conventional, efficient textile wet processing equipment and different types of fabric. This type of equipment can be used to scale-up the preparation of biocatalytic textiles to large quantities.

TABLE 9

Results of peroxide decomposition tests.

| | Cotton | Cotton-chi | Cotton-chi-TU-CAT | Rayon | Rayon-chi | Rayon-chi-TU-CAT |
|---|---|---|---|---|---|---|
| Bubble formation | No | No | Yes | No | No | Yes |
| Peroxide test after 1 hour with gentle mixing | Dark blue | Dark blue | White | Dark blue | Dark blue | White |

Example 35

Confined Liquid Wicking in Chitosan-Coated Yarn

The movement of water through cotton yarn and Cotton-chi-TU-CAT yarn was observed using neutron tomography and neutron imaging. In these techniques, a dark area in the displayed images corresponds to the presence of water. The dark areas in FIG. 3A show the wicking movement of water upwards through an initially dry cotton yarn. Initially (left image in FIG. 3A) the water wicks through the individual strands of this 4-ply yarn. Within 6 seconds (right image in FIG. 3A), water is present throughout the cotton yarn as well as in the spaces between the individual strands of the 4-ply yarn. FIG. 3B shows that water (dark line at bottom of images) moves into the dry cotton-chi-TU-CAT more slowly, with only the very bottom end of the yarn wetted with water after 6 seconds of contact with the water reservoir. Therefore, a different wicking behavior was observed for pristine cotton yarn compared to cotton-chi-TU-CAT yarn.

Neutron tomography imaging of the cotton and cotton-chi-TU-CAT yarns performed after 1 hour of yarn exposure to the wicking test showed that water (dark areas in the images) was located within and between the individual strands of the 4-ply cotton yarn, whereas in the cotton-chi-TU-CAT yarn, the water was confined within the each individual strand of the yarn without filling the space between the strands. See FIG. 3C.

These results indicate that water wicking was slowed down by the presence of the chitosan coating and that once absorbed, the water was confined inside the individual yarn strands, without filling up the air gap between the strands. This behavior can result in a higher interfacial area between the surrounding gas phase and the liquid in the cotton-chi-TU-CAT yarn compared to the liquid in the cotton yarn. A higher gas-liquid interfacial area can lead to efficient molecular mass transfer, and improved reaction efficiency for gas-liquid reactions. This result also illustrates the controlled transport of liquid from one location to another.

Example 36

Entrapment of Proteinase K in Chitosan Film from a Mild Solution

Proteinase K (40 mg, lyophilized powder, product number PB0451, Bio Basic Inc., Markham, Canada) was added into either "Solution A" or "Solution B" from Example 2 and then mixed at room temperature for 20 minutes to form "chitosan-Proteinase K solutions" with a chitosan to enzyme mass ratio of 10.

"Chitosan-Proteinase K solution" (10 g) was poured onto a PTFE tray and dried at room temperature for about 2 days under a ventilated hood. After the "chitosan-Proteinase K films" were prepared, the dry film was covered by aluminum foil and stored in a sealed bag at room temperature for a week before conducting tests. The film cast with "Solution A" was named chitosan-ProK(HAc) and the film cast with "Solution B" was named chitosan-ProK(NaAc).

Example 37

Degradation of Casein with Entrapped Proteinase K in Chitosan Film

Film samples including Proteinase K entrapped samples (chitosan-ProK(HAc), chitosan-ProK(NaAc)) and controls (chitosan films from "Solution A" and "Solution B") were cut into 0.1 g pieces with 2 cm×1.8 cm dimensions for the casein degradation test.

Casein substrate (50 mM) was prepared in phosphate buffered saline (phosphate buffered saline (PBS), pH 8.3) and 10 mL aliquots of the substrate were used in the degradation assay. A liquid sample was taken out from each test vial after 24 hours incubation at 37° C. and stored at room temperature for three days before running gel electrophoresis. The results of gel electrophoresis are shown in FIG. 4. The pattern of bands on the electrophoresis gel shows the presence of different proteins with different molecular weight. Larger proteins appear as bands towards the top of the gel and smaller proteins appear as bands towards the bottom of the gel. Lane 8 shows the electrophoresis pattern of casein substrate only. This shows that the casein substrate comprises many different proteins with different molecular weight. Lanes 1 and 2, corresponding to casein in the presence of chitosan films without Proteinase K, have a similar electrophoresis pattern to lane 8. Lane 5 shows the electrophoresis pattern of casein degraded by dissolved Proteinase K. This shows that the proteins in casein are significantly degraded by the presence of Proteinase K. Lanes 6 and 7 show the electrophoresis pattern of casein degraded by dissolved Proteinase K when chitosan films are present. Therefore, a comparison of lanes 6 and 7 to lanes 1 and 2 shows that the presence of dissolved Proteinase K in vials containing chitosan films caused casein to degrade. Lane 3 and 4, corresponding to chitosan films with Proteinase K entrapped, have a similar electrophoresis pattern to lane 5. Therefore, Proteinase K was active and able to degrade casein substrate after being entrapped in chitosan films.

Example 38

Esterase Assay of Entrapped Proteinase K in Chitosan Film

Film samples including Proteinase K entrapped samples (chitosan-ProK(HAc), chitosan-ProK(NaAc) and controls (chitosan films from "Solution A" and "Solution B") were cut into 0.1 g pieces with 2 cm×1.8 cm dimensions.

4-Nitrophenol (pNP) solutions (0 to 0.4 nmol/μL, 100 μL per well) were prepared in PBS buffer (pH 8.3), and a calibration curve was generated with absorbance measured at 405 nm. This calibration curve was used to convert the absorbance of each assay sample (100 μL per well) at 405 nm to the concentration of pNP (the reaction product) at predetermined time intervals.

4-Nitrophenyl Acetate (8 mM, pNPA) substrate was prepared by diluting 100 mM pNPA-ethanol solution with deionized water. Samples were placed in vials with 9.5 mL PBS, followed by adding 0.5 mL 8 mM pNPA substrate to each vial. The vials were shaken at 80 rpm at room temperature for 15 minutes, and the absorbance of 100 μL of liquid was measured at 405 nm wavelength right after being taken out from the vial. As shown in Table 10, below, the pNP concentrations with chitosan films present are similar to the blank, while the films with Proteinase K entrapped show higher pNP concentrations, which are similar to the pNP concentration observed with dissolved Proteinase K. Therefore, Proteinase K was active and able to hydrolyze pNPA substrate after being entrapped in chitosan films.

TABLE 10

Concentrations of pNP in the esterase assay.

| Sample | pNP concentration (nmol/μL) |
|---|---|
| blank | 0.03 |
| Positive control (~8 mg ProK) | 0.11 |
| Chi(HAc) | 0.02 |
| Chi(NaAc) | 0.02 |
| Chi-ProK(HAc) | 0.11 |
| Chi-ProK(NaAc) | 0.16 |

Example 39

Preparation of Chi-CAs Coated Fabric by Padding and Esterase Assay of Immobilized Carbonic Anhydrases Bovine carbonic anhydrase (bCA) was combined with either a portion of "solution A" or a portion of "solution B" (Example 2) to produce chitosan-bCA solutions. A microbial carbonic anhydrase (Novozymes A/S, Bagsvrd, Denmark), called "mCA," was combined with either a portion of "solution A" or a portion of "solution B" to produce chitosan-mCA solutions.

About 0.48 g cotton cheese cloth (Style # CHEESE 90, TestFabric Inc., West Pittston, Pa., United States of America) was padded with chitosan solution A or B (without enzyme) or padded with chitosan-bCA solutions or chitosan-mCA solutions to an average wet pick up of 58% using a laboratory padder (Werner Mathis AG, Zurich, Switzerland) and then air dried.

About 1.5 g cotton woven fabric (Style #400M, TestFabric Inc., West Pittston, Pa., United States of America) was padded with chitosan solution (without enzyme) or padded with chitosan-bCA solutions or chitosan-mCA solutions to an average wet pick up of 56% using a laboratory padder (Werner Mathis AG, Zurich, Switzerland) and then air dried.

Dried fabrics were cut into 1 cm×3.5 cm strips for the esterase assay as described in Example 38. The concentration of product 4-Nitrophenol (pNP) was plotted against time and the slopes (nmol per hour) of the linear plots are shown in Table 11. The slopes of the pNP concentration change when the chitosan padded fabrics without enzyme are present are similar to the slope of the blank (negative control). Therefore, the presence of chitosan-coated cotton does not change the rate of substrate hydrolysis. The slopes of the pNP concentration change for chitosan padded fabrics comprising entrapped CAs are about 30% higher than the corresponding blank and control fabrics, indicating that the entrapped CA enzymes are active in the biocatalytic textiles.

TABLE 11

Slopes of 4-Nitrophenol (pNP) concentrations in esterase assay.

| Sample | bCA | mCA |
|---|---|---|
| Chi (Ac) cotton | 0.21 | 1.4 |
| Chi (Ac) cheese cloth | 0.31 | 1.4 |
| Chi (NaAc) cotton | 0.19 | 1.4 |
| Chi (NaAc) cheese cloth | 0.22 | 1.5 |
| Chi (Ac) cotton with enzyme | 0.36 | 2.0 |
| Chi (Ac) cheese cloth with enzyme | 0.35 | 2.0 |
| Chi (NaAc) cotton with enzyme | 0.35 | 1.9 |
| Chi (NaAc) cheese cloth with enzyme | 0.44 | 2.0 |
| Blank (no textile and no enzyme) | 0.27 | 1.4 |

Example 40

Preparation of pH 5.3 Chitosan Solution

Solid chitosan powder (2.5 g, 100 mesh, 95% degree of deacetylation, ChitoClear 44020-fg95LV, Primex ehf, 580 Siglufjordur, Iceland), derived from shrimp shell, was dissolved with mixing in 50 mL of 5% (w/v) aqueous acetic acid solution (pH 2.5) to make a homogeneous 5% (w/v) "chitosan solution D." Chitosan solution D was poured onto a polytetrafluoroethylene (PTFE) tray and air dried in a fume hood at ambient temperature for at least 24 hours. The air drying allowed excess acetic acid to evaporate, leaving behind a solid "chitosan film C." Chitosan film C obtained in this way was dissolved in deionized water to obtain 5% (w/v) "chitosan solution E" (pH 5.3).

Example 41

Preparation of Chitosan Films with Entrapped Carbonic Anhydrase Enzyme Adsorbed in Chitosan Particles Mixtures of chitosan powder and test liquid were prepared by combining solid chitosan powder (100 mg, 100 mesh, 95% degree of deacetylation, ChitoClear 44020-fg95LV, Primex ehf, 580 Siglufjordur, Iceland), derived from shrimp shell, with 300 µL of test liquid in a weigh boat and thoroughly mixing to form a damp solid. Test liquids were (1) 100 mM aqueous sodium chloride ("control") and (2) 100 mM aq. NaCl containing 8 mg/mL carbonic anhydrase ("mCA"). The carbonic anhydrase was a carbonic anhydrase of microbial origin (Novozymes A/S, Bagsværd, Denmark). An amount (800 mg) of chitosan solution E was added to the weigh boat and mixed together with the damp solid to form "chitosan mixture A," comprising dissolved chitosan and solid chitosan particles. Chitosan mixture A was spread uniformly onto a glass slide and air dried in a fume hood for at least 12 hours to form "chitosan film C."

A 13 mm hole punch was used to cut three circular samples from each chitosan film C. The sample masses were 11+/−1 mg. The triplicate samples from each film were soaked with gentle agitation at room temperature for 5 minutes sequentially in three 5 mL changes of 50 mM sodium methoxide in methanol, followed by three 5 mL changes of fresh methanol, followed by three 5 mL changes of 25 mM Tris buffer (pH 7.2).

Samples were removed from the final soak and each sample was placed flat in the bottom of a 24-well microtiter plate. An amount (950 µL) of 25 mM Tris buffer (pH 7.2) was added to each well, followed by 50 µL of 4-Nitrophenyl Acetate (8 mM, pNPA) substrate. The samples were incubated for 60 minutes at 25° C. and the absorbance change in each well was measured at 405 nm. As shown by the results in Table 12, the presence of carbonic anhydrase enzyme (mCA), delivered into the film by adsorption in chitosan powder, caused a faster conversion of the pNPA substrate to pNP product.

TABLE 12

Rates of pNP release in the esterase assay.

| Sample | O.D. change/min | nmol of pNP released/min |
|---|---|---|
| Control (no enzyme) | −0.00063 | −0.149 |
| mCA | 0.0094 | 2.23 |

Example 42

Esterase Assay of Biocatalytic Textiles Comprising Chitosan and Carbonic Anhydrase Cotton textiles prepared as described in Example 41 were cut in donut shapes that fit in the bottom of the wells of a 24-well plate. The donut shape leaves an empty hole in the middle of the well that allows the light from the spectrophotometer to pass freely through the liquid. Four replicates of each cut textile sample were soaked with gentle agitation at room temperature for 5 minutes sequentially in three 10 mL changes of 50 mM sodium methoxide in methanol, followed by three 10 mL changes of fresh methanol, followed by three 10 mL changes of 25 mM Tris buffer (pH 7.2), and soaked overnight in Tris buffer. An amount (950 µL) of 25 mM Tris buffer (pH 7.2) was added to each well, followed by 50 µL of 4-Nitrophenyl Acetate (8 mM, pNPA) substrate. The samples were incubated for 60 minutes at 25° C. and the absorbance change in each well was continuously measured at 405 nm. As shown by the results in Table 13, the textiles comprising chitosan and carbonic anhydrase enzyme caused faster conversion of the pNPA substrate to pNP product for both mCA and bCA.

TABLE 13

Rates of pNP release in the esterase assay.

| Sample | O.D. change/min | nmol of pNP released/min |
|---|---|---|
| Control (no enzyme) | 0.00034 | 0.081 |
| mCA | 0.00095 | 0.225 |
| bCA | 0.0015 | 0.346 |

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A method of preparing a chitosan matrix material comprising an entrapped enzyme, the method comprising:
   providing an aqueous solution comprising dissolved chitosan, said aqueous solution having a pH of between about 2.5 and about 5.5;
   adding at least one enzyme to the aqueous solution to provide a chitosan/enzyme solution, wherein the chitosan/enzyme solution comprises a mass ratio of chitosan to enzyme (on a dry basis) of greater than about 0.5; and
   solidifying the chitosan to provide a solid chitosan matrix by one of:
   (a) applying the chitosan/enzyme solution onto a solid support or substrate,
   (b) applying the chitosan/enzyme solution to at least one portion of a surface of a textile substrate, or
   (c) contacting the chitosan/enzyme solution with a coagulation solution;
   wherein the at least one enzyme is stably entrapped within the chitosan matrix, thereby forming the chitosan matrix material.

2. The method of claim 1, wherein providing the aqueous solution comprising dissolved chitosan further comprises:
   (i) dissolving a protonated chitosan salt in a solution having a pH of between about 2.5 and 5.5; or
   (ii) dissolving a solid chitosan in an aqueous solution comprising an organic acid and having a pH of between about 2.0 and about 4.5; and
      (ii-a) adjusting the pH of the solution to between about 2.5 and about 5.5; or
      (ii-b) drying the solution comprising the organic acid to provide a dry protonated chitosan and redissolving the dry protonated chitosan in a solution having a pH of between about 2.5 and about 5.5.

3. The method of claim 1, wherein solidifying the chitosan comprises applying the chitosan/enzyme solution onto a solid support or substrate, wherein the applying comprises pouring, spreading, dipping, painting, rolling, padding, pressing, squeezing, extruding, spraying or printing; and drying the chitosan/enzyme solution to form a film or coating comprising a solid chitosan matrix.

4. The method of claim 1, wherein solidifying the chitosan comprises applying the chitosan/enzyme solution to at least one portion of a surface of a textile substrate, and drying the chitosan/enzyme solution to form a film or coating comprising a solid chitosan matrix on the at least one portion of the surface of the substrate.

5. The method of claim 1, wherein solidifying the chitosan comprises contacting the chitosan/enzyme solution with a coagulation solution thereby forming a solid chitosan matrix, wherein the at least one enzyme is stably entrapped within the solid chitosan matrix.

6. The method of claim 5, wherein the method is free of: (i) the use of a covalent cross-linking agent reacted with the chitosan prior to, during, or both prior to and during the formation of the solid chitosan/enzyme matrix; and (ii) the addition of an additional polyanion to the chitosan/enzyme mixture; optionally wherein the method is further free of the use of collagen and/or wherein the at least one enzyme is an acid-sensitive and/or a heat sensitive enzyme.

7. The method of claim 1, wherein the at least one enzyme remains active and stably entrapped within the chitosan matrix after repeated washings with water or a solution comprising water.

8. The method of claim 1, wherein the at least one enzyme is selected from the group consisting of an oxidoreductase, a transferase, a hydrolase, a lyase, an isomerase, and a ligase.

* * * * *